(12) United States Patent
Schwarz et al.

(10) Patent No.: US 6,572,867 B1
(45) Date of Patent: Jun. 3, 2003

(54) INHIBITION OF XENOREACTIVE ANTIBODIES

(75) Inventors: Alexander Schwarz, Plainsboro, NJ (US); Guerard W. Byrne, Allentown, NJ (US); Thomas A. Davis, Newtown, PA (US); Lisa E. Diamond, Princeton, NJ (US); John S. Logan, Robbinsville, NJ (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/292,153

(22) Filed: Apr. 15, 1999

Related U.S. Application Data

(63) Continuation-in-part of application No. 09/060,525, filed on Apr. 15, 1998, now abandoned.

(51) Int. Cl.[7] .................... A61K 47/26; A61K 39/385; A61K 31/70
(52) U.S. Cl. ................ 424/278.1; 424/184.1; 424/193.1; 424/194.1; 424/279.1; 424/280.1; 514/23
(58) Field of Search ............... 424/279.1, 278.1, 424/194.1, 193.1, 184.1, 280.1; 514/23

(56) References Cited

FOREIGN PATENT DOCUMENTS

| WO | WO 93/03735 | 3/1993 |
| WO | WO 97/23637 | 7/1997 |
| WO | WO 98/33528 | 9/1998 |
| WO | WO 98/47915 | 10/1998 |
| WO | WO 99/01140 | 1/1999 |

OTHER PUBLICATIONS

PCT International Search Report, International Application No. PCT/US 99/08326.

Chen, Xi et al., "Carbohydrates In Transplantation", Current Opinion in Chemical Biology 3: 650–658 (1999).

Li, Jun et al.; "Bacteria Targeted By Human Natural Antibodies Using α–Gal Conjugated Receptor–Specific Glycopolymers", Bioorganic & Medicinal Chemistry 7: 1549–1558 (1999).

Renkonen, O. et al.; "Synthesis of a New Nanomolar Saccharide Inhibitor of Lymphocyte Adhesion: Different Polylactosamine Backbones Present Multiple Sialyl Lewis X Determinants to L–selectin in High–affinity Mode", Glycobiology 7(4): 453–461 (1997).

Seppo, A. et al.; "Synthesis of a Tetravalent Sialyl Lewis X Glycan, a High–affinity Inhibitor of L–Selectin–mediated Lymphocyte Binding to Endothelium", Glycobiology, 6(1): 65–71 (1996).

Nagasaka et al., "α–Galactosyl Oligosaccharides Conjugated with Polyethylene Glycol as Potential Inhibitors of Hyperacute Rejection Upon Xenotranspantation", Biochemical and Biophysical Research Communications 232: 731–736 (1997).

*Primary Examiner*—Bennett Celsa
(74) *Attorney, Agent, or Firm*—Dana M. Gordon; Foley Hoag LLP

(57) ABSTRACT

One aspect of the present invention relates to methods and compositions for attenuating xenograft rejection by administering, to an animal receiving the xenograft, an amount of a polymer-derivatized xenoantigen (hereinafter "xenopolymer") effective for inhibiting or lessening the severity of hyperacute rejection response (HAR), or other immunological response to the graft, that is dependent on the presence of the xenoantigen on the grafted tissues or cells. In certain embodiments, the xenopolymer is administered in an amount sufficient to neutralize host antibodies ("xenoreactive antibodies" or "XNA") immunoreactive with the xenoantigen. The xenopolymer may additionally, or alternatively, be used as a tolerogen (or anergen) for the xenoantigen, e.g., able to suppress, to some degree, the production/secretion of XNAs by the immune system of the host.

7 Claims, 35 Drawing Sheets

CHEMICAL STRUCTURES arm, 10,000 MW $$\text{R-NH-CH}_2\text{CH}_2\text{(OCH}_2\text{CH}_2\text{)}_n\text{OCH}_2 - \overset{\overset{\displaystyle \text{CH}_2\text{O(CH}_2\text{CH}_2\text{O)}_n\text{CH}_2\text{CH}_2\text{NH-R}}{|}}{\underset{\underset{\displaystyle \text{CH}_2\text{O(CH}_2\text{CH}_2\text{O)}_n\text{CH}_2\text{CH}_2\text{NH-R}}{|}}{C}} - \text{CH}_2\text{O(CH}_2\text{CH}_2\text{O)}_n\text{CH}_2\text{CH}_2\text{NH-R}$$

n ~ 56

$$R = H;\ NH_2(CH_2)_4\text{-}\underset{\underset{NH_2}{|}}{CH}\text{-}\overset{\overset{O}{\|}}{C}\text{-}\ ;\ SO_3\text{-}S\text{-}(CH_2)_2\text{-}\underset{\underset{NH_2}{|}}{CH}\text{-}\overset{\overset{O}{\|}}{C}\text{-}$$

arm, 10,000 MW
20,000 MW $$NH_2CH_2CH_2(OCH_2CH_2)_n\text{-}O\text{-}(CH_2CHCH_2O)_6\text{-}(CH_2CH_2O)_n\text{-}CH_2CH_2\text{-}NH_2$$
$$|$$
$$O\text{-}(CH_2CH_2O)_n\text{-}CH_2CH_2NH_2$$

n for 10,000 MW ~28 n for 20,000 MW ~56

Fig. 1

IC$_{50}$ VALUES FOR VARIOUS MOLECULES

| MOLECULE | IC$_{50}$(M) |
|---|---|
| GalGalGlcNAc | 50 |
| 410S | 0.001 |
| 410E | 1 |
| 410LS | 0.001 |
| 410L | 0.5 |
| 410SS | 1 |
| 410ES | 1 |
| 410N | 1 |
| 810E | 0.1 |
| 810S | 0.00001 |
| 820E | 0.1 |
| 820S | 0.00001 |

Fig. 24

INHIBITION OF XENOREACTIVE ANTIBODIES

RELATED APPLICATIONS

This application is a continuation-in-part and claims the benefit of the filing date of U.S. patent application Ser. No. 09/060,525, filed Apr. 15, 1998 (abandoned).

TECHNICAL FIELD OF THE INVENTION

This invention is in the general field of pharmaceuticals for treatment of conditions caused by xenoreactive antibodies.

BACKGROUND

Organ Transplantation

Organ transplantation is now widely viewed as the preferred treatment for end stage organ failure, based on both a quality of life and cost basis. One year graft survival for kidney and heart transplantation at the major transplant centers is now greater than 90% with acute rejection rates less than 30%. There are approximately 2500 heart transplants and 12,500 kidney transplants performed every year in the USA. The major limitation to more widespread utilization of this procedure is a shortage of available organs. This can be seen by looking at the transplant waiting list, which shows that more than twice the number of people are waiting for an organ than could ever receive one. Additionally, 10 people per day die while waiting for a transplant. The demand for organs, however, is much greater than the number of people on the transplant waiting list. There are 125,000 patients in end stage renal failure who theoretically could benefit from a transplant. It is also been estimated that 25,000 to 40,000 people could benefit from a heart transplant if a donor organ were available.

The availability of human organs is not likely to increase in any significant way over the next few years and even if all of the potential human donor organs could be utilized this would only increase the number of organs transplanted by about 2 fold, far less than the actual demand. Possible mechanical solutions to this problem such as left ventricular assist devices for cardiac failure while adequate at least for temporary support appear unlikely to provide for a long-term solution and as yet no implantable device exists for a kidney. Indeed, renal transplantation is viewed as superior and preferred in terms of the quality of life compared to dialysis. Given these alternatives the medical and scientific communities have turned to animals to provide for a solution to the organ shortage problem.

Animals as Donors

The preferred animal species for transplantation to humans is the pig. Although the closely related non-human primate species are immunologically more similar to humans, and therefore the rejection process which is seen upon transplantation could likely be more easily controlled by current immunosuppressive drugs, a number of reasons make this possibility remote. First, a non-human primate of appropriate size for a heart transplant into an adult human would be a chimpanzee or equivalent large animal. These animals are on the endangered species list and thus would raise significant ethical questions even if it were possible to breed large numbers in captivity. The most abundant non-human primate, which is the baboon, is small and could not provide hearts for transplantation into adult humans although conceivably kidneys or livers would be possible. However, the baboon contains a number of potentially pathogenic organisms which could present a problem if transmitted to a human, and the generation of large numbers of specific pathogen free animals would be extremely costly and time consuming. The pig, a domesticated farm animal, on the other hand is of an appropriate size, can be raised to obtain specific pathogen free animals and is available in large numbers. Clearly, if the immunological problems could be overcome the pig would be the ideal donor to solve the organ shortage problem.

The Immunological Problem

The initial barrier to transplantation of a pig organ to primates is a process of hyperacute rejection which results in the loss of the graft within a few minutes to hours of transplantation and is characterized histologically by thrombosis, hemorrhage, edema and a lack of a cellular infiltrate (Platt, J. L., et al., *Immunology Today* 11:450–456, 1990). This process is initiated by the binding of antibody, which is already present in the recipient, to the graft endothelium, and the resulting activation of the complement cascade. A similar process can be seen in allografts when antibody is present in the recipient prior to transplantation. In thinking about the pig as a donor, it is useful to review the effect of pre-existing antibodies on allograft survival and what strategies are important in obtaining prolonged graft survival.

The presence of antibody in the serum of an allograft recipient, which recognizes antigen present on the donor endothelium, can be an indicator of a poor prognosis for long-term graft survival. Indeed, in a percentage of these allografts a rapid process of rejection, as described above for pig to primate xenografts, in which the graft is lost within a few minutes to hours after reperfusion, can occur. An example of this situation is seen when the donor and recipient are incompatible with regard to the blood group ABO system. The blood group antigen, which is a carbohydrate, is present on the donor endothelium. When a graft from a blood group A donor is transplanted into a blood group O recipient, in which antibody against the blood group A antigen is present, antibody is deposited in the graft. In the case of these grafts in which hyperacute rejection occurs the binding of antibody to the graft endothelium causes complement to be fully activated which results in damage to the endothelium and subsequent loss of the endothelial barrier function resulting in thrombosis, hemorrhage, edema and irreversible graft failure. If hyperacute rejection does not occur many, though clearly not all, of the grafts are lost due to vascular rejection in the subsequent weeks to months. These transplants were initially performed in the pre-cyclosporin era and led to the suggestion that matching for ABO compatibility should be performed prior to transplantation.

As the success of allografts improved, dramatic shortages in the availability of organs led a number of groups to reassess the possibility of transplanting across the ABO barrier particularly in the case of living related kidney donors. These investigators found that in order to routinely prevent hyperacute rejection and achieve optimal long term graft survival, comparable to that obtained with ABO matched grafts, the antibody present at the time of transplant has to be temporarily removed usually by physical means such as immunoapheresis. A standard or in some cases an enhanced immunosuppression protocol is then applied. Under these circumstances the long-term outcome for these grafts is as good as would be obtained with ABO compatible grafts. In a percentage of these ABO incompatible grafts antibody apparently returns to the circulation but the graft is not rejected and this phenomenon has been termed "accommodation". However, it is still far from clear that this antibody as detected in standard haemagglutination reactions is actually capable of binding to the graft. In many circumstances the antibody does not return in a detectable form to the circulation, although it is certainly conceivable that antibody is bound to the graft.

In a pig to primate xenograft, the xenoreactive antibody which is found in the recipient prior to transplant predominantly if not exclusively recognizes the unique carbohydrate structure, αGal(1,3)Gal. This structure is found as the terminal sugar on glycolipids and glycoproteins present on the donor pig endothelium. The pig and many other mammals but not humans or Old World monkeys synthesize this epitope. This scenario is in many ways reminiscent of the ABO blood group mismatched allografts described above. In a similar fashion to the mammalian blood group antigens such as the human blood group A, the lack of the antigen in an animal results in the synthesis of antibodies which recognize it. This antibody is probably induced and stimulated on an ongoing basis by gut bacteria, which possess a related structure. Indeed, Galili et. el (1988) showed that anti-Gal antibodies bound to a variety of enterobacteria such as $E.coli$, klebsiella and salmonella. The Gal reactive structure varied between the bacteria and was either the lipopolysaccharide or the capsular polysaccharide (Hamadeh et. el. 1992). Both of these classes of antigens are well known as T-cell independent antigens. Additionally, the isotype of the ABO and α-Gal antibodies are similar, the levels of antibody in the serum are similar and the density of the carbohydrate antigens on the donor endothelium are also within the same range. However, when a pig to primate organ transplant is performed the graft is almost always rejected within a few minutes to hours with the very occasional graft lasting at most several days. This is in direct contrast with what happens in the allograft where the occasional graft is hyperacutely rejected and the majority survive for prolonged periods of time (weeks to months). A significant difference between the survival of allografts and xenografts under these conditions is most likely due to the incompatibility of the complement regulatory proteins. In the xenografts, antibody binds to the graft endothelium and results in the activation of the complement cascade. In the case of the allograft there are a series of proteins present on the donor endothelium which regulate the activity of complement and can be thought of as a primitive self/non-self-recognition process whereby if complement is inadvertently activated on the endothelium it can be inactivated before damage occurs. These proteins include Decay Accelerating Factor (DAF: CD55), Membrane Cofactor Protein (MCP: CD46) and CD59. In the case of the pig, the pig equivalent of the human CRP's does not function effectively to limit the action of human complement. Therefore, when complement is activated in the xenograft due to the functional lack of the CRP's the endothelium is severely damaged resulting in thrombosis, hemorrhage, edema and graft loss. This hypothesis has been confirmed by the generation of transgenic pigs, which express human CRP's and routinely overcome hyperacute rejection.

If this were the only difference between an allograft and a xenograft then one might assume that with the addition of immunosuppression or antibody removal plus immunosuppression and the use of transgenic animals that one would observe xenograft survival with a similar time course as in an allograft. However, the simple addition of immmunosuppression does not substantially prolong graft survival and the organ invariably succumbs to vascular rejection. Antibody removal at the time of transplant combined with immunosuppression can prolong survival but not reach survival levels comparable with an allograft and again vascular rejection inevitably ensues. This vascular rejection is characterized histologically like hyperacute rejection by hemorrhage, thrombosis, and a lack of a cellular infiltrate; however, unlike hyperacute rejection there are significant regions of ischaemia. Immunopathological analysis reveals that antibody is bound to the graft but very little complement components are deposited.

There are exceptions to this course of events and these are found when exceptionally high doses of immunosuppressive agents, whose mechanism of action is related to their antiproliferate effect, are utilized or the physical removal of antibody by immunoapheresis in the post transplant period is aggressively continued. Taken together with the lack of a cellular infiltrate these results suggest that the organs are being lost due to a vascular rejection process which is most likely an antibody mediated event although the mechanism whereby antibody causes this rejection process are not yet clear.

When the graft is present in the recipient, it is difficult to determine the level and specificity of xenoreactive antibody because the graft can act as a sink and bind up the antibody. We sought to circumvent this problem by following the antibodies in the animal after the removal of a rejected non life supporting heterotopic heart transplant and at the same time maintain the immunosuppressive regime after the graft is removed. Under these circumstances soon after the graft removal and in the following few days we observe a rapid rise in xenoreactive antibody levels in the animal. This is characterized by a 4–10 fold increase in IgM and a 100–200-fold increase in IgG. These antibodies almost exclusively recognize the αGal(1,3)Gal structure. A similar rise in αGal(1,3)Gal antibodies is seen in humans who are the recipients of cellular pig xenografts such as pancreatic islets or who have been exposed to a pig liver in an ex vivo perfusion circuit. These data suggest that the grafts are lost due to the enhanced production of αGal(1,3)Gal antibodies.

The observation that the antibodies which we hypothesize mediate graft rejection in the pig to primate species combination predominantly recognize a single chemically defined epitope raises the possibility to control this antibody production in a specific manner. Specificity in the control of the immune response would be advantageous because it would reduce the risk of infectious complications associated with generalized immunosuppression. As discussed above, these responses are not easily controlled by current immunosuppression at clinically relevant levels making the rationale for a greater specificity even more important.

In vivo neutralization of antibody by the administration of soluble ligand has been proposed for both ABO incompatible allografts and pig to primate xenografts. In both systems the infusion of large amounts of sugar are required due to a combination of low affinity of the ligand for antibody and short half life in the serum. In experimental ABO incompatible baboon to baboon heart allografts, if sugar infusion is maintained for a number of days in the presence of immunosuppressive agents the infusion can be stopped and long term graft survival can be achieved. In many ways this is reminiscent of the observation that the temporary removal of antibody by physical means, for example plasma exchange or specific immunoapheresis in combination with immunosuppression, can result in long-term graft survival.

In the case of the pig to primate xenograft the administration of soluble forms of the αGal(1,3)Gal carbohydrate has prevented hyperacute rejection, however, as soon as the sugar infusion is stopped the graft is rejected. To date the infusion has not been maintained for a prolonged enough period of time to assess when, if at all, the infusion can be stopped, as was the case with the allograft. It is conceivable that there is a substantial difference between allograft and xenograft rejection such that infusion cannot be stopped in the vast majority of cases. This experiment could be at least conceptually improved if it were possible to either dramatically improve the half-life of the sugar or, increase the affinity or both such that much less was required or dosing was less frequent.

SUMMARY OF THE INVENTION

One aspect of the present invention provides a polymer, synthesized by a cross-coupling reaction of
  (i) polymer scaffold units, comprising a plurality of nucleophilic or electrophilic functional groups, and
  (ii) xenoantigens comprising a functional group capable of reacting with the functional groups presented on the polymer scaffold unit,
wherein the reaction is carried out in the presence of a crosslinking reagent under conditions wherein polymer scaffold units are coupled with xenoantigens, and separate polymer scaffold units are cross-linked to one another.

In certain embodiments, the functional groups for the polymer scaffold units and xenoantigens are selected from the group consisting of amine and carboxylic acid, alcohol and alkyl halide or sulfonate, thiol and alkyl halide or sulfonate, phosphine and alkyl halide or sulfonate, phosphite and alkyl halide or sulfonate, and aldehyde or ketone and amine. In preferred embodiments, the functional groups produce an amide, ether, thioether, or phosphate linkage between the polymer scaffold unit and xenoantigen upon cross-coupling.

The cross-coupling may be carried out, e.g., in the presence of an activating agent that activates the functional groups of the polymer scaffold units and xenoantigens for forming a covalent bond there between. For instance, the activating group may be a dehydrating agents, Bronsted acid, Bronsted base, Lewis acid, Lewis base, acyl halide, or a phosphoryl halide. In certain preferred embodiments, the activating agent is a diimide, e.g., dicyclohexyldiimide [DCC] or ethyl-3-(dimethylamino)propyldiimide [EDC].

In certain embodiments, the polymer scaffold units are pharmacologically-acceptable, non-immunogenic molecules. For instance, the polymer scaffold units can be polyethylene glycol, an oligopeptide, or oligosaccharide (e.g., qextran, dextrin or a cyclodextrin) bearing nucleophilic or electrophilic functional groups. Suitable nucleophilic or electrophilic functional groups include amines, alcohols, thiols, selenols, phosphines, aldehydes, ketones, acid chlorides, acids, esters, alkyl halides, and alkyl sulfonates. In particular embodiments, the functional group on the polymer scaffold unit is an amino or carboxylate moiety, and the functional group of the xenoantigen reacts therewith to form an amide linkage.

In certain preferred embodiments, the polymer scaffold unit is as multiply-aminated polyethylene glycol, e.g., octa (amino)polyethylene glycol. In additional embodiments, the polymer scaffold unit is aminated dextran or an aminated cyclodextrin. In further embodiments, the polymer scaffold is a dendridic polyamine.

The xenoantigen can be, to illustrate, a carbohydrate, a peptide, a glycopeptide or a lipid. In certain preferred embodiments, xenoantigen includes an epitope which is cross-reactive with an xenoreactive antibody against α-galactosyl moieties, and more preferably the xenoantigen is an oligosaccharide, e.g., having an αGal(1,3)Gal moiety represented by the general formula:

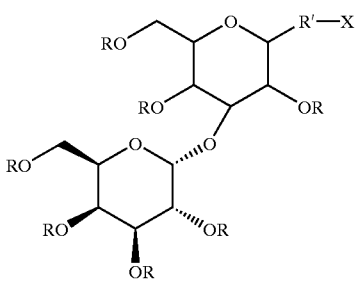

wherein:

R, independently for each occurrence, represents H or a $C_1$–$C_6$ alkyl or other hydroxyl protecting group;

R' is absent or represents an oligosacchride consisting of 1–8 saccharide residues; and X represents a bond or linker moiety linking the oligosacchride moiety to the polymer backbone, e.g., preferably being a cyclic, branched or straight chain aliphatic group of 2–10 bonds in length, cycloalkyl, alkenyls, cycloalkenyl, alkynyl, aryl, heteroalkyl, or heteroaryl moiety.

For example, the xenoantigen can include an oligosacchride having represented by one of the general formula:

(III)

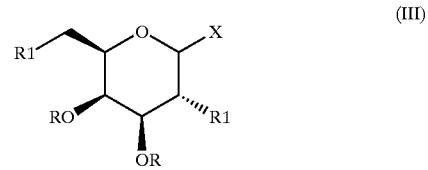

(IV)

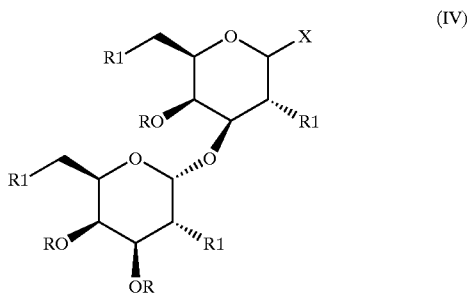

(V)

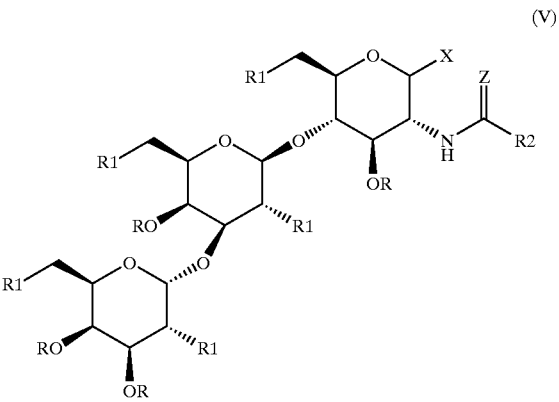

-continued

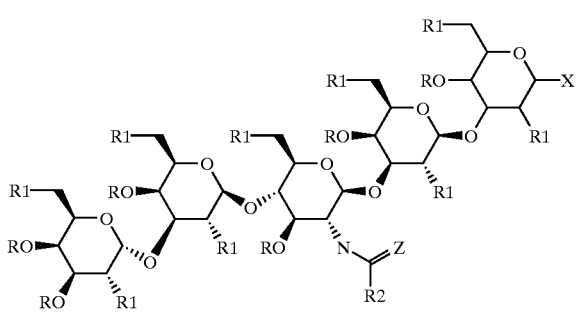

(VI)

wherein,
R1, independently for each ocurrence, is H, —OR, —SR or —N(H)—Y—R;
R, independently for each occurrence, represents H or a $C_1$-$C_6$ alkyl or other hydroxyl protecting group;
R2 is a $C_1$-$C_6$ alkyl;
Y, independently for each occurrence, is absent, or —C(S)—, —S(O)$_2$—, —C(O)—A—;
X represents a bond or linker moiety linking the oligosacchride moiety to the polymer backbone;
Z is O or S; and
A is —NH—, —NH—($C_1$-$C_6$ alkyl)-, —NH—($C_1$-$C_6$ alkenyl)-, —O—, —O—($C_1$-$C_6$ alkyl)-, —O—($C_1$-$C_6$ alkenyl)-, —S—, —S—($C_1$-$C_6$ alkyl)-, —S—($C_1$-$C_6$ alkenyl)-.

In certain preferred embodiments, the xenoantigen includes one or more of: αGal(1,3) βGal; αGal(1,3)βGal(1,4)βGlcNAc; or αGal(1,3)βGal(1,4)βGlc moieties. In other embodiments, the xenoantigen may include one or more of: αGal(1,2)Gal, αGal(1,4)Gal, βGal(1,3)GalNAc or 3-O-sulphated galactose ($SO_4$-3Gal).

The xenoantigen can be a di-, tri-, tetra- and penta-oligosaccharides.

In certain embodiments, the polymer is homogenous with respect to the xenoantigen displayed thereon. In other embodiments, the polymer includes two or more different xenoantigens, e.g., on the same molecule.

In particular preferred embodiments, the crosslinking agent has at least two functional groups capable of reacting with the polymer scaffold units, the xenoantigen, the covalent linkage of the scaffold with the xenoantigen, or a combination thereof. For instance, the crosslinking agent can be derived from N-hydroxysulfosuccinimide.

In certain preferred embodiments, the cross-coupling reaction is carried out in the pH range of 4 to 7.

In certain preferred embodiments, the cross-coupling reaction is carried out in the temperature range of 0° C. and 40° C.

In certain preferred embodiments, the cross-coupling reaction is carried out a temperature, pH, reactant concentration and for a time sufficient to yield a polymer having a nominal molecular weight of 100,000–500,000 daltons. In certain embodiments, e.g., for tolerogenic forms of the, xenopolymer, the cross-coupling reaction is carried out a temperature, pH, reactant concentration and for a time sufficient to yield a polymer having a nominal molecular weight less than 100,000 daltons.

In certain preferred embodiments, the xenopolymer of the instant invention induces B cell anergy for the xenoantigen.

For many applications, the subject xenopolymer is formulated with a pharmaceutical excipient, and is preferably formulated as a sterile formulation.

Another aspect of the present invention is a method for manufacture of a medicament using the subject xenopolymer, the medicament being administered to a patient which is to receive, or has received, a discordant tissue graft, and in an amount sufficient to reduce the severity of rejection of the graft.

In preferred embodiments, the medicament is formulated with a xenopolymer having a therapeutic index for preventing discordant graft rejection of at least 10.

Another aspect of the present invention provides a kit, including two or more of the subject xenopolymers, each polymer isolated from the other and homogenous with respect to the xenoantigen displayed thereon but different from at least one other polymer of the kit.

Another aspect of the present invention provides a polymer comprising a plurality of subunits interconnected by crosslinking moieties. See generally, FIG. 25. Each crosslinking moiety is covalently bound to at least two subunits, although the individual bonds between a crosslinker and a subunit need not be of the same type or comprise the same atom(s) of the subunits. The individual subunits comprise a backbone or scaffold, and a plurality of xenoantigens. The xenoantigens are covalently tethered to the backbone or scaffold, typically via a tether consisting of between 10 and 20 non-hydrogen atoms. The backbone or scaffold may itself be a polymer, e.g., an oligoethylene glycol, oligosaccharide, or oligopeptide. The synthesis of a polymer of this embodiment of the present invention may be achieved in a single reaction or in a series of reactions. When the synthesis of the polymer occurs in a single reaction, the process comprises combining the backbone or scaffold with the crosslinking agent and the xenoantigens to give a product comprising subunits, i.e., individual backbone or scaffold groups to which xenoantigens have been tethered, that are covalently interconnected via crosslinking moieties. See FIG. 25. When the synthesis of the polymer occurs in a series of reactions, the overall process comprises: combining the backbone or scaffold with the xenoantigens under conditions where the two react to generate subunits bearing a plurality of tethered xenoantigens; and combining the subunits bearing a plurality of tethered xenoantigens with the crosslinking agent to form crosslinks between the individual subunits.

Certain embodiments of this aspect of the present invention provide a polymer, comprising a polymer backbone of polyethylene glycol subunits, at least a portion of which have attached thereto a saccharide moiety represented in the following general formula:

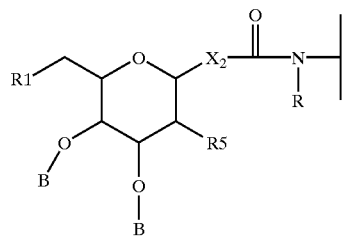

wherein
R1, independently for each ocurrence, is H, —OR, —SR or —N(H)—Y—R;
R5 is H, —OR, NH—Y—R2, or —L—E;
Y independently for each occurrence is absent, —C(O)—, —C(S)—, —C(NR)—, O, S, or Se;
B, for one occurrence is —R, and for the other occurrence is —R or from 1–9 saccharide residues;

R, independently for each occurrence, represents H or a $C_1$–$C_6$ alkyl, a protecting group, or —L—E;

R2 is a $C_1$–$C_6$ alkyl;

X2 represents a linker of 1–10 atoms in the length;

L represents a linker of 1–20 atoms in length, e.g., preferably being a cyclic, branched or straight chain aliphatic group of 2–15 bonds in length, cycloalkyl, alkenyls, cycloalkenyl, alkynyl, aryl, heteroalkyl, or heteroaryl moiety; and E represents a second PEG subunit of the polymer, wherein, independently for each occurrence of E, the linker group L is covalently attached via R5 or B of a saccharide moiety of the second PEG subunit, or via an amine of the second PEG subunit or via an amide moiety in the tether between the saccharide and the corresponding polyethylene glycol subunit.

Certain embodiments of this aspect of the present invention provide a polymer, comprising a polymer backbone of polyethylene glycol subunits, at least a portion of which have attached thereto a saccharide moiety represented in the general formula (VII):

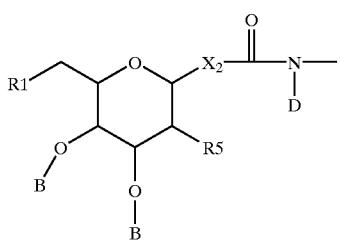

(VII)

wherein,

R1, independently for each ocurrence, is H, —OR, —SR or —N(H)—Y—R;

R5 is H, —OR, NH—Y—R2, or —L—E;

Y independently for each occurrence is absent, —C(O)—, —C(S)—, —C(NR)—, O, S, or Se;

B, for one occurrence is —R, and for the other occurrence is —R or from 1–9 saccharide residues;

R, independently for each occurrence, represents H or a $C_1$–$C_6$ alkyl or other hydroxyl protecting group;

R2 is a $C_1$–$C_6$ alkyl;

X2 represents a linker of 1–10 atoms in the length;

D represents H, or —L—E;

L represents a linker of 1–20 atoms in length; and

E represents a second PEG subunit of the polymer, wherein, independently for each occurrence of E, the linker group L is covalently attached via R5 or B of a saccharide moiety of the second PEG subunit, or via an amine of the second PEG subunit.

Still another aspect of the present invention is directed to a polymer, represented by the general formula

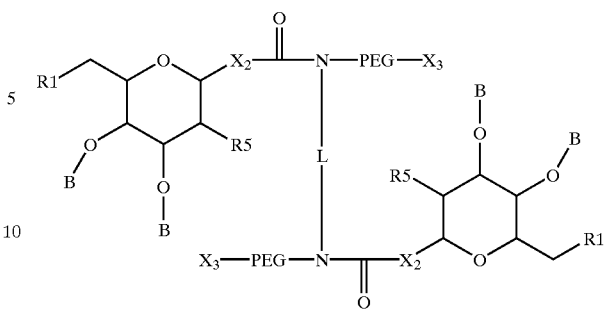

wherein

R1, independently for each ocurrence, is H, —OR, —SR or —N(H)—Y—R;

R5 is H, —OR, NH—Y—R2, or —L—E;

Y independently for each occurrence is absent, —C(O)—, —C(S)—, —C(NR)—, O, S, or Se;

B, for one occurrence is —R, and for the other occurrence is —R or from 1–9 saccharide residues;

R, independently for each occurrence, represents H or a $C_1$–$C_6$ alkyl or other hydroxyl protecting group;

R2 is a $C_1$–$C_6$ alkyl;

X2 represents a linker of 1–10 atoms in the length

D represents H, or —L—E;

L represents a linker a linker of 1–20 atoms in length;

E represents another polyethylene glycol subunit of the polymer having a saccharide moiety VII attached thereto, wherein, independently for each occurrence of E, the linker group L is covalently attached via R5 or B in the saccharide moiety.

PEG represents a polyethylene glycol subunit; and

X3 represents one or more additional polyethylene glycol subunit which may be derivatived with a a saccharide moiety of formula VII, wherein the polymer has an average molecular weight in the range of 10,000 daltons to 1,000,000 daltons.

Still another aspect of the invention relates to a composition including: a non-immunogenic pharmacologically acceptable carrier; and multiple αGal(1,3)Gal moieties covalently linked to said carrier.

The invention is also directed to a composition useful for reducing plasma levels of anti-(αGal(1,3)Gal) antibodies in a primate subject in need of a pig organ transplant. Herein, the term "primate" is understood to include humans. Reduction of levels of circulating anti-(αGal(1,3)Gal) antibodies is expected to prevent or ameliorate hyperacute rejection of the donated pig organ, thereby allowing long-term function of the transplanted organ.

The composition of the invention comprises a non-immunogenic pharmacologically acceptable carrier covalently linked to multiple αGal(1,3)Gal moieties.

The invention is also directed to methods for synthesizing the composition.

A preferred method is to react in a solution at a pH of 4–7 the following reagents:

a branched polymer, exemplified by polyethylene glycol, which has at least three arms and a minimum of 6 active groups such as amino groups or hydrazino group at its free ends, αGal(1,3)Gal having a covalently linked carboxy group, and N-(3-dimethylaminopropyl)-N'-ethylcarbodiimide (EDC).

A second preferred method is conducted as above, except the branched polymer has covalently linked carboxy groups, and the αGal(1,3)Gal has a covalently linked active group such as an amino or hydrazino group.

A third preferred method is to react in a solution at a pH range of 4 to 7 the following reagents:
a branched polymer having at least three arms, and at least six active groups such as amino or hydrazino groups covalently linked to the free ends of the arms, and
αGal(1,3)Gal having a covalently linked aldehyde.

A fourth preferred method is conducted as the third method above, except that the branched polymer has at least six aldehydes covalently linked to its arms, and the αGal(1,3)Gal has a covalently linked amino group or hydrazino group.

A fifth preferred method is to react in a solution at a pH range of 4 to 7 the following reagents:
a branched polymer having at least three arms and at least three covalently linked active groups such as amino or hydrazino groups,
αGal(1,3)Gal having a covalently linked carboxy group,
EDC, and
N-hydroxysulfosuccinimide (NHSS).

A sixth preferred method is conducted as the fifth method above, except that the branched polymer has covalently linked carboxy groups and the αGal(1,3)Gal has covalently linked amino or hydrazino groups.

The invention also provides methods for reducing plasma levels of anti-(αGal(1,3)Gal) antibodies in primate subjects, including human subjects, by administering the composition of the invention.

The invention is also directed to a kit and methods for detecting and quantifying anti-(αGal(1,3)Gal) antibody secreting cells in the blood of a subject.

Yet another aspect of the invention provides a method for attenuating rejection of tissues from a donor animal of one species transplanted to a recipient animal of another species, comprising administering to the recipient animal an amount of a polymer reactive with xenoreactive antibodies of the recipient animal effective for delaying or lessening the severity of a graft rejection response, wherein the polymer has epitopes cross-reactive with an xenoantigen of the graft, and rejection of the tissue is mediated at least in part by the expression of the xenoantigen on the tissue.

The subject method can be used as part of a pre-treatment program for a patient who is to be transplanted with tissue or cells from a discordant species, and/or for treatment of a patient who has been transplanted with tissue or cells from a discordant species. In preferred embodiments, the method reduces or otherwise attenuates the severity of hyperacute rejection of the transplanted tissues. In certain embodiments, the polymer is administered in an amount sufficient to neutralize host antibodies immunoreactive with the xenoantigen.

In preferred embodiments, the receipient does not possess an endogenous UDP galactose:β-D-galactosyl-1,4-N-acetyl-D-glucosminide α(1,3) galactosyltransferase (α1,3-GT) activity or does not otherwise produce or display the αGal(1,3)Gal xenoantigen on its cells, tissues or organs. For instance, the recipient can be a human or old world primate.

In certain preferred embodiments, the xenograft is of pig origin, more preferably minature swine.

The xenotransplanted tissue can be an organ, e.g., a vascularized organ, such as a kidney, heart, lung or liver. The xenotransplant tissue may also be in the form of parts of organs, cell clusters and glands, such as pancreatic islet cells, skin, corneal tissue and bone marrow or other preparations of hematopoietic cells.

In one embodiment, there is provided a method for reducing plasma levels of anti-(αGal(1,3)Gal) antibodies in a primate subject, said method comprising administering to said subject a composition comprising:
a non-immunogenic pharmacologically acceptable carrier; and
multiple αGal(1,3)Gal moieties covalently linked to said carrier.

Still another aspect of the present invention provides a complex comprising one or more B-cells associated with a composition comprising:
a non-immunogenic pharmacologically acceptable carrier; and
multiple αGal(1,3)Gal moieties covalently linked to the carrier.

Yet another aspect of the present invention provides a complex comprising one or more antibodies associated with a composition comprising:
a non-immunogenic pharmacologically acceptable carrier; and
multiple αGal(1,3)Gal moieties covalently linked to said carrier.

Another feature of the instant invention provides a kit for detecting and quantifying anti-(αGal(1,3)Gal) antibody-secreting cells in the blood of a subject comprising:
a multi-well plate to which αGal(1,3)Gal is covalently coupled;
blocking solution comprising a buffer and human serum albumin;
serum-free complete culture medium;
anti-human immunoglobulin antibodies; and
means for labeling said anti-human immunoglobulin antibodies bound to the plate.

Still another feature to the instant invention is a method for detecting and quantifying anti-(αGal(1,3)Gal) antibody-secreting cells in the blood of a subject comprising:
providing peripheral blood mononuclear cells isolated from a blood sample of said subject;
providing a multi-well plate to which αGal(1,3)Gal is covalently coupled;
incubating said peripheral blood mononuclear cells on said plate for a sufficient time and under appropriate conditions to allow
anti-(αGal(1,3)Gal) antibody-secreting cells and their antibodies to bind specifically to said αGal(1,3)Gal coated on said plate;
washing said plate to remove non-binding cells;
incubating said anti-(αGal(1,3)Gal) antibody-secreting cells and their antibodies bound to said αGal(1,3)Gal coated on said plate with anti-human immunoglobulin antibodies;
washing said plate to remove non-binding anti-human immunoglobulin antibodies;
applying a means to label anti-human immunoglobulin antibodies bound to said plate; and,
quantifying single anti-(αGal(1,3)Gal) antibody-secreting, spot forming cells indicated by spots formed on said plate by the binding of said labelled anti-human immunoglobulin antibodies.

BRIEF DESCRIPTION OF THE DRAWINGS

FIG. 1 depicts the chemical structures of 4-arm and 8-arm polyethylene glycol with active groups at the end of each arm. In synthesizing an exemplary composition of the invention (TPC), αGal(1,3)Gal β1–4 GlcNAc is covalently bound at amino sites on the ends of the arms.

FIG. 24 presents the IC$_{50}$ values of various molecules in the inhibition assay.

DETAILED DESCRIPTION

(i) Overview

Figure 2:
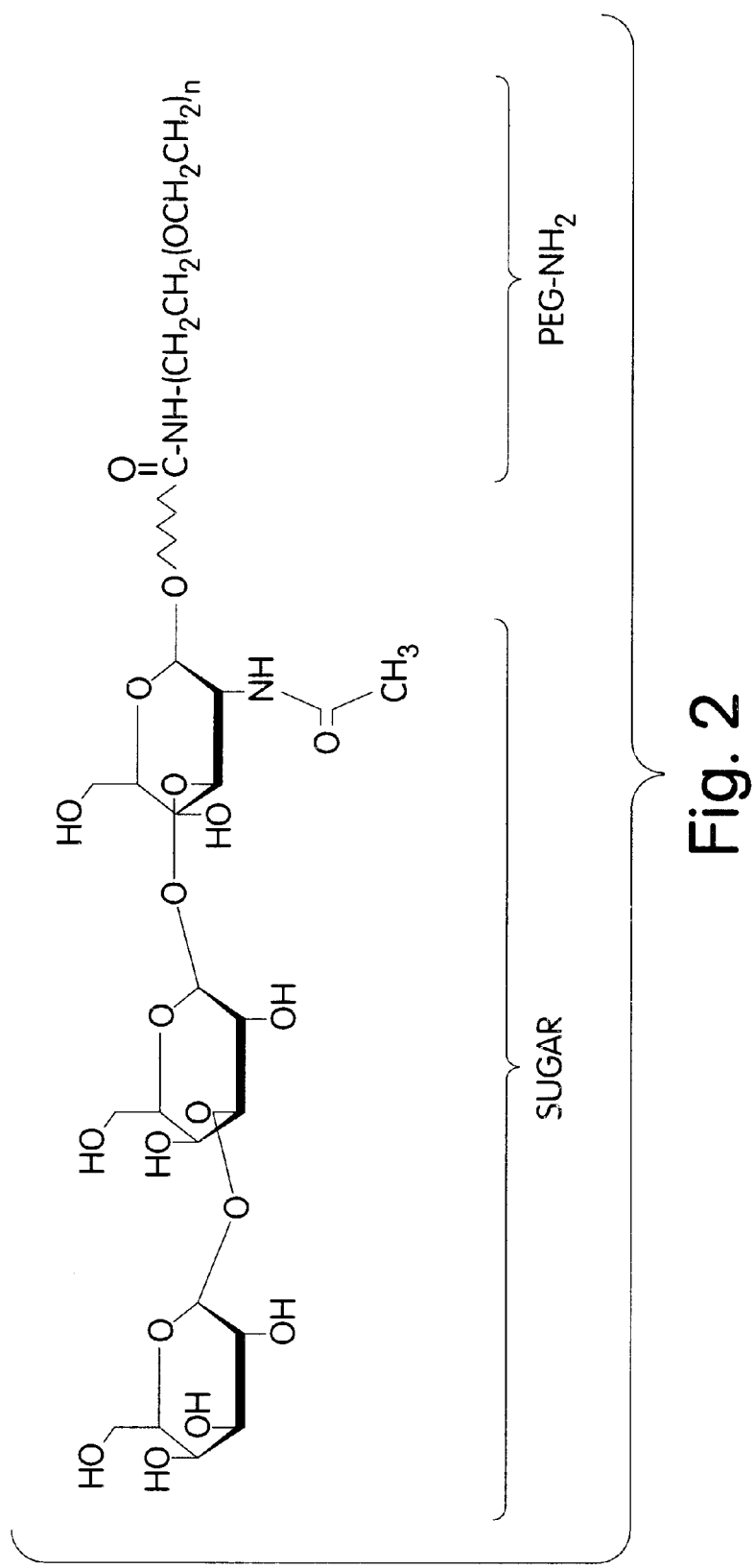
FIG. 2 depicts the chemical structure of αGal(1,3)Gal β1–4 GlcNAc (sugar) covalently bound to one arm of a multi-armed polyethylene glycol (PEG-NH$_2$).

The primary obstacle to all forms of organ transplantation is the rejection of the transplant by the recipient's immune system. The more closely related the donor and recipient are, the less likely the transplanted organ will be rejected. In allotransplantation, the transplantation of organs between the same species, the problem of immune rejection Can be largely overcome by immunosuppressive drugs. The current shortage of human tissues for human transplantation, however, has led to use of xenografts as a source of organs. A problem which arises when tissues from non human-species are grafted to humans is one of hyperacute rejection, which occurs due to the existence of natural antibodies in human serum which react with antigens present in these species. This phenomenon depends, in general, on the presence of some or all of antibody, complement, neutrophils, platelets and other mediators of inflammation.

Pigs are top candidates for xenotransplant donors because their physiology and anatomy parallel that of humans, and because they are plentiful and can be raised under clean conditions to minimize risk of infection. In the context of transplantation of pig tissue into humans, hyperacute rejection is associated at least in part with host antibodies reactive with galactosyl antigens present on the pig tissue, such as αgalactosyl (1,3) galactose moieties (the "αGal(1,3)Gal" or "αGal" epitope). Inhibiting the interaction between host antibodies reactive with the αGal(1,3)Gal epitopes of xenotransplant tissue can be used to prevent rejection.

One aspect of the present invention relates to methods and compositions for attenuating xenograft rejection by administering, to an animal receiving the xenograft, an amount of a polymer-derivatized xenoantigen (hereinafter "xenopolymer") effective for inhibiting or lessening the severity of hyperacute rejection response (HAR), or other immunological response to the graft, that is dependent on the presence of the xenoantigen on the grafted tissues or cells. In certain embodiments, the xenopolymer is administered in an amount sufficient to neutralize host antibodies ("xenoreactive antibodies" or "XNA") immunoreactive with the xenoantigen. The xenopolymer may additionally, or alternatively, be used as a tolerogen (or anergen) for the xenoantigen, e.g., able to suppress, to some degree, the production/secretion of XNAs by the immune system of the host.

As described in further detail below, the xenoantigen can be, to illustrate, a carbohydrate, a protein (or peptidyl portion thereof), a lipid or other fatty acid moitey, or a nucleic acid. In certain preferred embodiments, the xenoantigen(s) that is disposed on the polymer is immunoreactive with host XNAs against carbohydrate epitopes of the xenograft, and more preferably is immunoreactive with host antibodies against α-galactosyl epitopes, such as an αGal(1,3)Gal epitope.

The polymer component, e.g., the backbone of the subject xenoploymers, is preferably derived from a polymer that is water-soluble, and substantially non-toxic and non-immunogenic. Illustrative polymers of this type include polyethyleneglycols, polyvinylpyrrolidones, polyacrylamides, dextrans, and polyglycomers. In preferred embodiments, however, the xenopolymer is formed from a polyamine, such as aminated polyethyleneglycols, polyalkylamines, polypeptides (such as polylysine, polyornithine, polyarginine, polyasparagine, polyglutamine), polyallylamines, poly[N(2-aminoethyl)] methacrylamides, and polyaminocarbohydrates such as aminodextran or chitosan. The polymer may be homopolymeric or copolymeric, and if the latter, may be a block or statistical copolymer.

In certain embodiments, the subject method can be used to promote tolerance to the αGal(1,3)Gal antigen in a recipient mammal which does not possess an endogenous UDP galactose:β-D-galactosyl-1,4-N-acetyl-D-glucosminide α(1,3) galactosyltransferase (α1,3-GT) activity or which otherwise does not produce or display the αGal(1,3)Gal antigen on its cells, tissues or organs. Thus, in preferred embodiments, the recipient animal is a human or old world primate, e.g., a baboon (such as *Papio anubis*) or cynomolgus monkey (such as *Macaca fascicularis*).

Xenografted tissue is preferably of pig origin, though tissues from other non-human mammals are also contemplated for use in this invention. Preferably the xenotransplanted tissue is in the form of an organ, and more preferably a vascularized organ, as for example, kidney, heart, lung or liver. Xenotransplant tissue may also be in the form of parts of organs, cell clusters, glands and the like. Examples include lenses, pancreatic islet cells, skin, corneal tissue and bone marrow or other preparations of hematopoietic cells.

The xenopolymers of the present invention have interesting properties. In particular, they have affinity for human polyclonal XNAs present in body fluids, e.g., blood, and are useful as depleting agents. In certain embodiments, the subject xenopolymers can be used for intracorporal depletion of XNAs, e.g., by injection, infusion or perfusion of the polymer into a xenograft recipient prior to and/or after transplantation. The xenopolymers of the present invention, in certain embodiments, may also be used as a pharmaceutical for inducing tolerance or anergy towards xenoantigenic epitopes or to specifically target B cells with xenoantigen receptors. The administration may be repeated as required to achieve tolerance.

Thus, in one embodiment the method of the present invention includes a step of pre-treating a patient, who is to be transplanted with tissue or cells from a discordant species, with an effective amount of the subject xenopolymer so as to reduce the risk of hyperacute rejection or other adverse immunological reaction to the xenograft, upon transplantation.

In another embodiment, the subject method includes a step of treating a patient, who has been transplanted with tissue or cells from a discordant species, with an effective amount of the subject xeno-polymer so as to reduce the risk of hyperacute rejection or other adverse immunological reaction to the xenograft.

Treatment according to the method of this invention will not necessarily prevent all aspects of rejection, but it will be effective to suppress the antibody-dependent component of transplant rejection. Even partial suppression of rejection is beneficial, because mitigation of the rejection phenomena will allow rescue of some of the tissue in the graft in a viable state. For example, even a partially functioning kidney may permit the recipient to avoid dialysis or prolong the periods between dialysis, even if some cell lysis has occurred. Similarly, a fully functional heart graft is preferable, but mitigation of rejection sufficient to permit some increase in exertion by the recipient, relative to the recipient's state before transplant, is valuable. Partial rescue of liver tissue in a liver graft undergoing rejection is also valuable because the remaining viable liver tissue can recover and regenerate while the patient is supported with coagulation proteins and other substances normally produced by the liver.

As described in further detail below, the subject method can be combined with other transplantation therapies, including immunoaphoresis and other treatment protocols for inducing accommodation, immunosuppressive therapy and the use of genetically engineered donor tissue.

Still another aspect of the invention relates to compositions including the subject xenopolymers, especially polymers displaying xenoantigens immunoreactive with host antibodies against α-galactosyl epitopes such as αGal(1–3)Gal. In preferred embodiments, the polymer preparations are formulated with a pharmaceutically acceptable excipient, are sterile, and are substantially non-pyrogenic.

For certain of the subject xenopolymers, it is the combined properties of activity at a very low molar concentration plus long-term stability that make the compositions of the invention practical and useful as pharmaceuticals. These properties allow for effectiveness at low doses, which are expected to be well tolerated by patients in need of chronic reduction of circulating anti-Gal antibodies. The stability of the compositions allows for long-term storage at temperatures achievable in a household setting, thus opening the possibility that patients may self-administer the pharmaceuticals over the long term, perhaps even over their entire lifetime after receiving a pig organ transplant.

Another aspect of the present invention relates to the use of the subject xenopolymers in the manufacture of a medicament for the treatment of a discordant graft rejection, wherein the medicament is administered to a patient either as a pre-transplant conditioning or for maintenance after transplantation, or both, and in an amount sufficient to reduce the severity of rejection of the graft.

(ii) Definitions

For convenience, certain terms employed in the specification and appended claims are collected here.

The term "Gal" refers to galactose; "Glc" refers to glucose and "GlcNAc" refers to N-acetylglucosamine.

The terms "sugar monomers" or "saccharide subunits", which are used interchangeably herein, refer to naturally occurring sugars, such as galactose, glucose and the like, as well as sugar monomers which are modifications thereof. For example, the term includes protected, partially protected or unprotected deoxysugars of the D- and L-configurations, preferably 2-, 3-, 4-, 5- and 6-deoxyaldoses, such as fucose, rhamnose and digitoxose, 1,2-dideoxyaldoses, such as glucal, galactal and fucal, and 1-, 3-, 4-, 5- and 6-deoxyketoses, 2-, 3-, 4-, 5- and 6-deoxyaminosugars of the D and L configurations, such as glucosamine, mannosamine, galactosamine and fucosamine, and deoxyacylaminosugars, such as N-acylglucosamine, N-acylmannosamine, N-acylgalactosamine and N-acyl-fucosamine, preferably their $C_1$–$C_4$ alkyl esters. In addition, these modifications are understood to mean aldonic, aldaric and uronic acids, such as gluconic acid or glucuronic acid, and also ascorbic acid and amino acid-carrying sugar monomers. Modified sugar monomers are also understood to mean those having a carbon chain which is longer than 6 C atoms, such as heptoses, octoses, nonoses, heptuloses, octuloses and nonuloses, and also their representatives which are substituted in accordance with the above-listed criteria, such as ketodeoxyoctanic acid, ketodeoxynonanic acid, N-acylneuraminic acids and N-acylmuraminic acids.

Oligosaccharides are considered to have a reducing end and a non-reducing end, whether or not the saccharide at the reducing end is in fact a reducing sugar. In accordance with accepted nomenclature, oligosacchrides are depicted herein with the non-reducing end on the left and the reducing end on the right.

All oligosacchrides described herein with the name or abbreviation for the non-reducing sacchride (e.g., Gal), followed by the configuration of the glycosidic bond (α or β), the ring bond, the ring position of the reducing sacchride involved in the bond, and the name or abbreviation of the reducing sacchride (e.g., GlcNAc). The linkage is preferably α-O-glycosidic or β-O-glycosidic, e.g., (1→2)-, (1→3)-, (1→4)-, (1→5)-, (1→6)-, (2→3)- and (2→6)-glycosidic linkages. Examples of disaccharides are e.g. trehalose, sophorose, kojibiose, laminaribiose, maltose, cellobiose, isomaltose, gentibiose, sucrose and lactose, and their derivatives. Examples of trisaccharides are raffinose and melezitose. Furthermore, the oligosaccharides may be linked via S—, N—and C-glycosidic linkages, e.g. —S—, —$NR^{12}$—, —$NR^{12}C(O)$— or —$CR^{13}R^{14}$—, wherein $R^{12}$, $R^{13}$ and $R^{14}$ independently of each other are H,$C_1$–$C_{12}$alkyl, $C_5$- or $C_6$cycloalkyl, $C_5$- or $C_6$cycloalkylmethyl or -ethyl, phenyl, benzyl or phenethyl. Generally, each saccharide subunit is a pyranose.

An "αGal(1,3)Gal moiety", or αGal moiety, refers to two galactosyl residues, the Gal residue at the reducing end being an α-galactosyl moiety, that are covalently joined by a 1–3 glycosidic linkage.

The term "αGal oligosaccharide" refers to oligosaccharides (e.g., containing two or more saccharide moieties) including the αGal(1,3)Gal moiety.

The term "XNA" refers to xenoreactive natural antibodies, such as human antibodies which are immunoreactive with the carbohydrate αGal(1,3)Gal epitope on pig tissues.

As used herein, "hyperacute rejection" refers to rapid graft rejection, beginning minutes after implantation, and which is mediated by pre-existing antibodies to the graft.

As defined herein, a "xenograft" may be an organ, tissue, aggregates of cells, or cells, collectively referred to herein as "tissue". The graft may be selected from any appropriate tissue of the body of the tissue donor. These tissues include, but are not limited to, heart, kidney, lung, islet cells, liver, bowel, skin and hematopoietic cells.

The phrases "reduce xenograft rejection" and "attenuate xenograft rejection", which are used interchangeably herein, mean to inhibit, interfere with or otherwise reduce the severity of processes resulting in hyperacute rejection, such as, but not limited to, ischemia, thrombosis, myocardial congestion and tissue necrosis.

The terms "xenogeneic" and "xenograft" refer to cells or tissue which originates with or is derived from a species other than that of the recipient.

The term "autologous" refers to tissue or cells which originate with or are derived from the recipient, whereas the terms "allogeneic" and "allograft" refer to cells and tissue which originate with or are derived from a donor of the same species as the recipient.

An "immunosuppressive agent", as used herein, is an agent, e.g., a chemical agent, e.g., a drug, which, when administered at an appropriate dosage, results in the inhibition of T cells. Examples of such agents are cyclosporine, FK-506, and rapamycin.

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Tolerance", as used herein, refers to an inhibition of a graft recipient's immune response which would otherwise occur, e.g., in response to the introduction of a nonself antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Moreover, tolerance, as used herein, refers to a donor antigen-specific inhibition of the immune system as opposed to the broad spectrum inhibition of the immune system seen with immunosuppressants.

"Inhibiting immune cell activity" refers to reducing the number of active immune cells, e.g., thymocytes, T cells, B cells, or NK cells, preferably donor reactive cells, or precursor donor reactive cells, in a subject. Inhibition can include partial inhibition, or partial reduction (as opposed to total elimination) of the number of active immune cells, e.g., T cells.

"Discordant species combination", as used herein, refers to two species in which hyperacute rejection occurs when a graft is grafted from one to the other. Generally, discordant species are from different orders, while non-discordant species are from the same order. For example, rats and mice are non-discordant concordant species. Concordant species combinations do not exhibit hyperacute rejection. In xenogeneic method of the invention, the donor and recipient (subject) can be a discordant species combination.

"Miniature swine", as used herein, refers to a miniature pig which is preferably wholly or partially inbred at at least one MHC locus. The coefficient of inbreeding of the herd which supplies the miniature swine should be at least , 0.70 and more preferably at least 0.82. The herd from which donor animals are drawn should be homozygous at the SLA genes.

As used herein, "myeloablative" refers to a treatment in which death, due to marrow failure, in a significant number of recipients, will occur if hematopoietic stem cell transplantation is not given.

As used herein, "non-myeloablative" refers to a treatment which kills marrow cells but will not, in a significant number of recipients, lead to death from marrow failure.

The term "subject", as used herein, refers to a mammal, e.g., a human.

The term "$ED_{50}$" means the dose of a drug, e.g., a subject polymer, which produces 50% of its maximum response or effect. Alternatively, the dose which produces a predetermined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

(iii) Illustrative Embodiments

In one aspect, this invention provides pharmaceutical compositions capable of reducing plasma levels of anti-($\alpha$Gal(1,3)Gal ("anti-($\alpha$Gal")) antibodies in primate subjects, including human patients. While the instant invention contemplates methods and compositions for reducing xenoreactive antibodies to other antigens, for clarity, most of the discussion to follow focuses on oligosaccharide xenoantigens. The compositions are intended for administration to patients being prepared for transplant of a tissue or cells from a discordant donor, such as a pig organ, a kidney or heart, or patients who have already received such transplants and are in need of reduction of anti-($\alpha$Gal antibodies in order to prevent or reduce rejection or other antibody-dependent degradation in performance of the pig organ, e.g., to reduce hyperacute rejection of the organ.

A. Illustrative Xenopolymers

Figure 25:
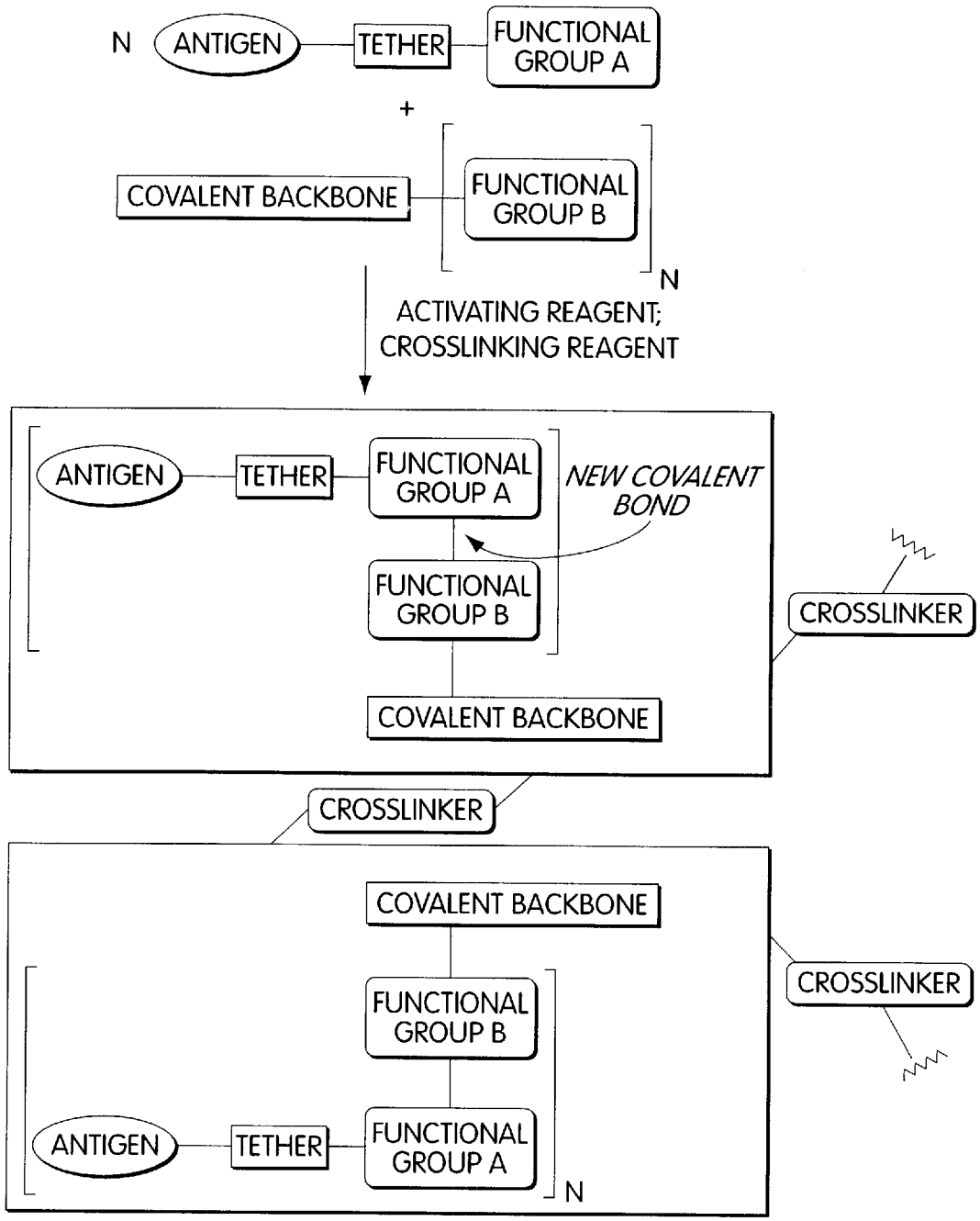
FIG. 25 depicts a schematic representation of one possible structure for the products produced by the instant processes.
Figure 26:
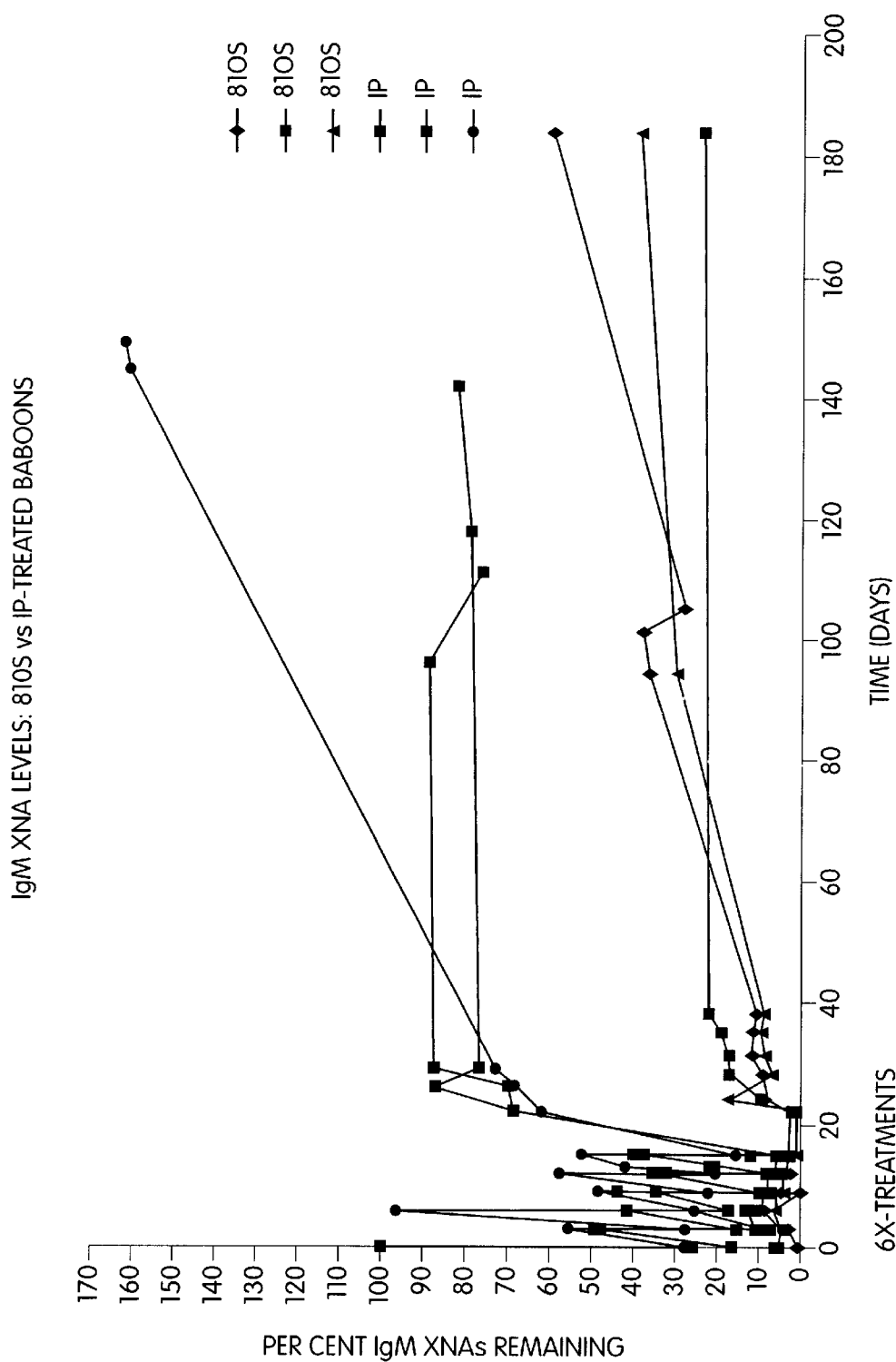
FIG. 26 is a graph of IgM XNA Levels: 810S vs IP-treated baboons. Baboons were either treated with 810S (50 mg/kg) every 3 days for a total of 6 treatments, or underwent a total of 6 immunoapheresis treatments using α-gal columns every 3 days. Serum from each baboon was analyzed by ELISA for IgM antibodies directed against the α-gal epitope. The per cent IgM XNAs remaining were calculated using baseline values from each animal as 100%.
Figure 27:
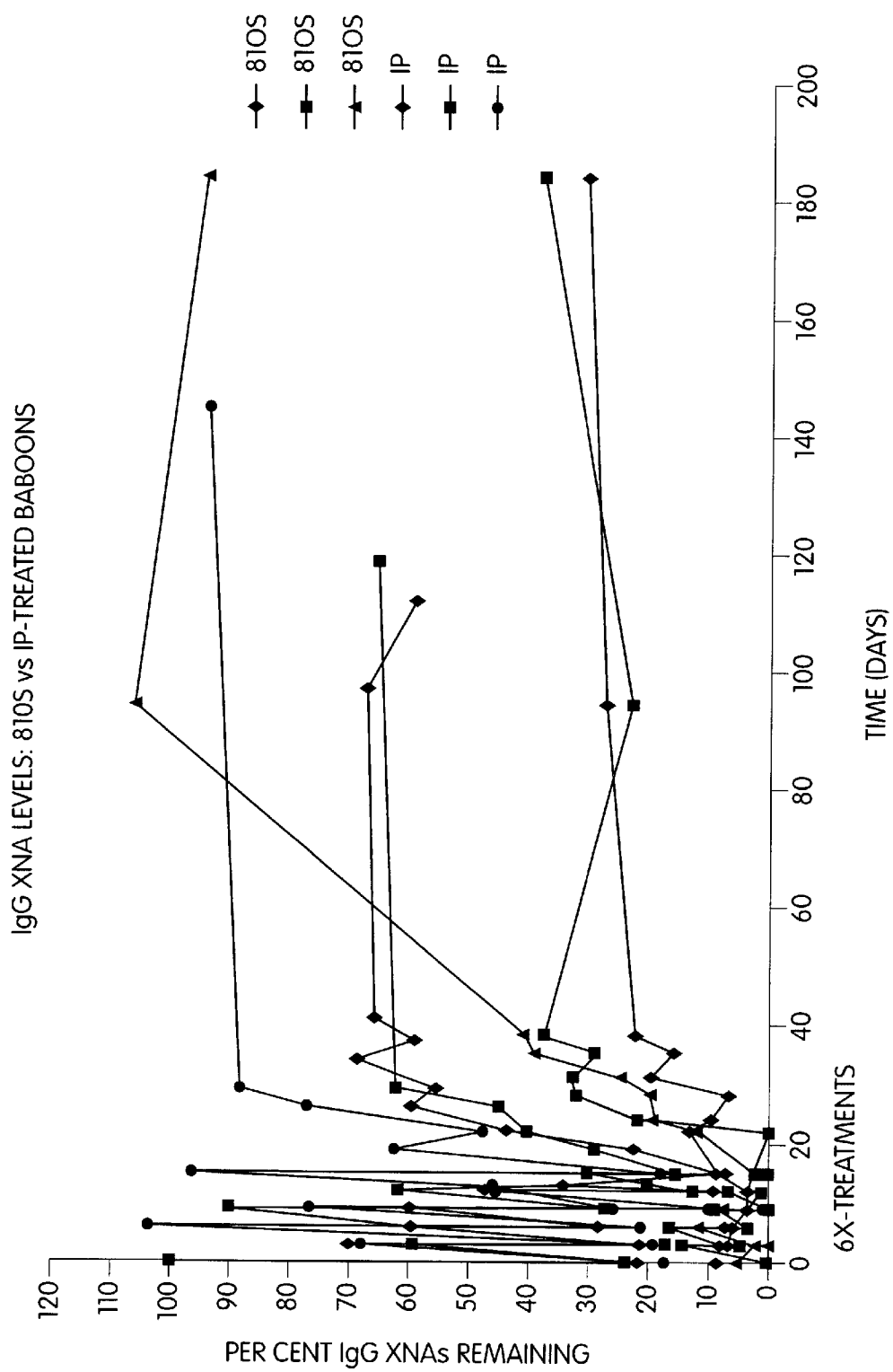
FIG. 27 is a graph of IgG XNA Levels: 810S vs IP-treated baboons. Baboons were either treated with 810S (50 mg/kg) every 3 days for a total of 6 treatments, or underwent a total of 6 immunoapheresis treatments using α-gal columns every 3 days. Serum from each baboon was analyzed by ELISA for IgG antibodies directed against the α-gal epitope. The per cent IgM XNAs remaining were calculated using baseline values from each animal as 100%.
Figure 28:
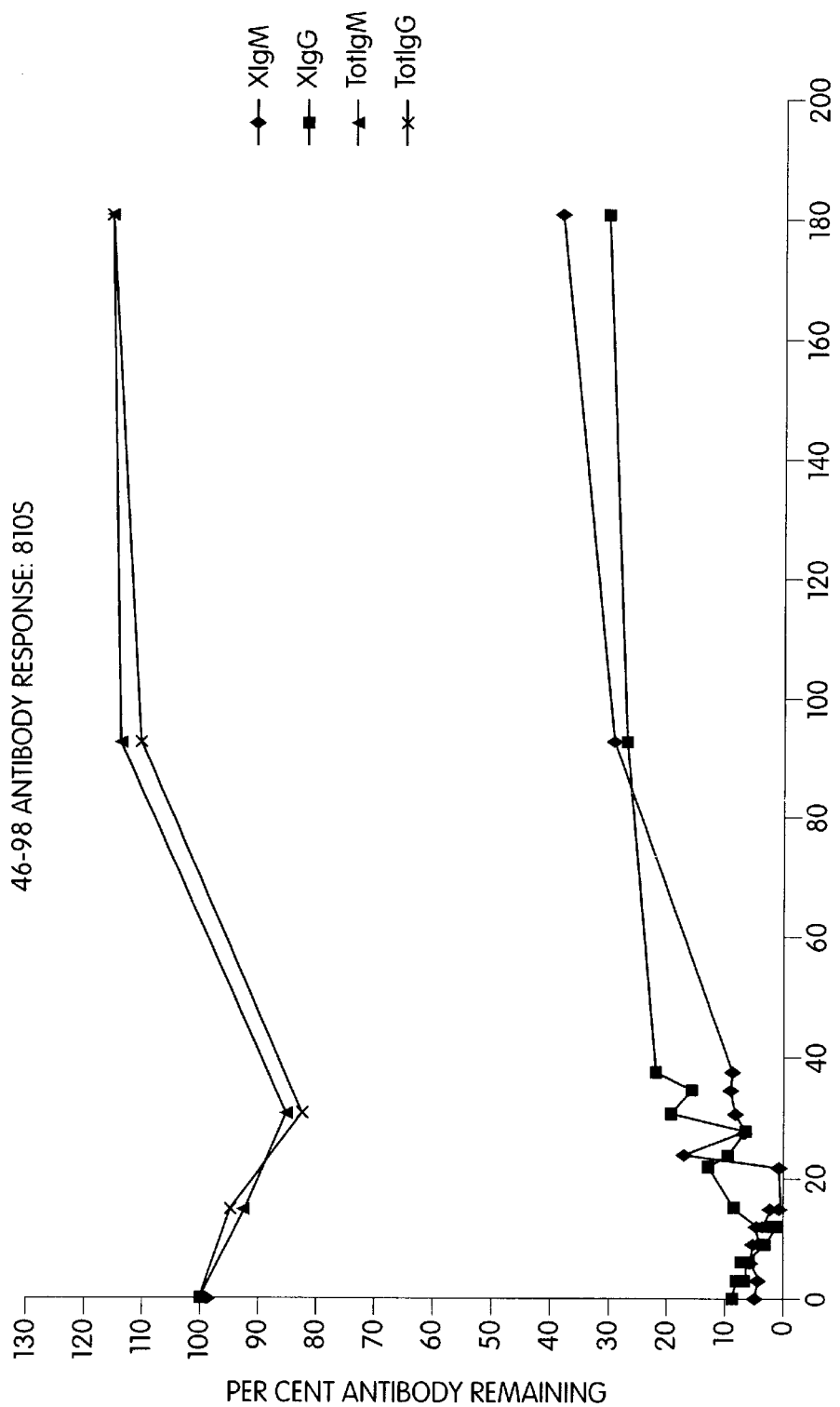
FIG. 28 is a graph of baboon 46–98 antibody response to 810S. Baboon 46–98 was treated with 810S (50 mg/kg) every 3 days for a total of 6 treatments. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.
Figure 29:
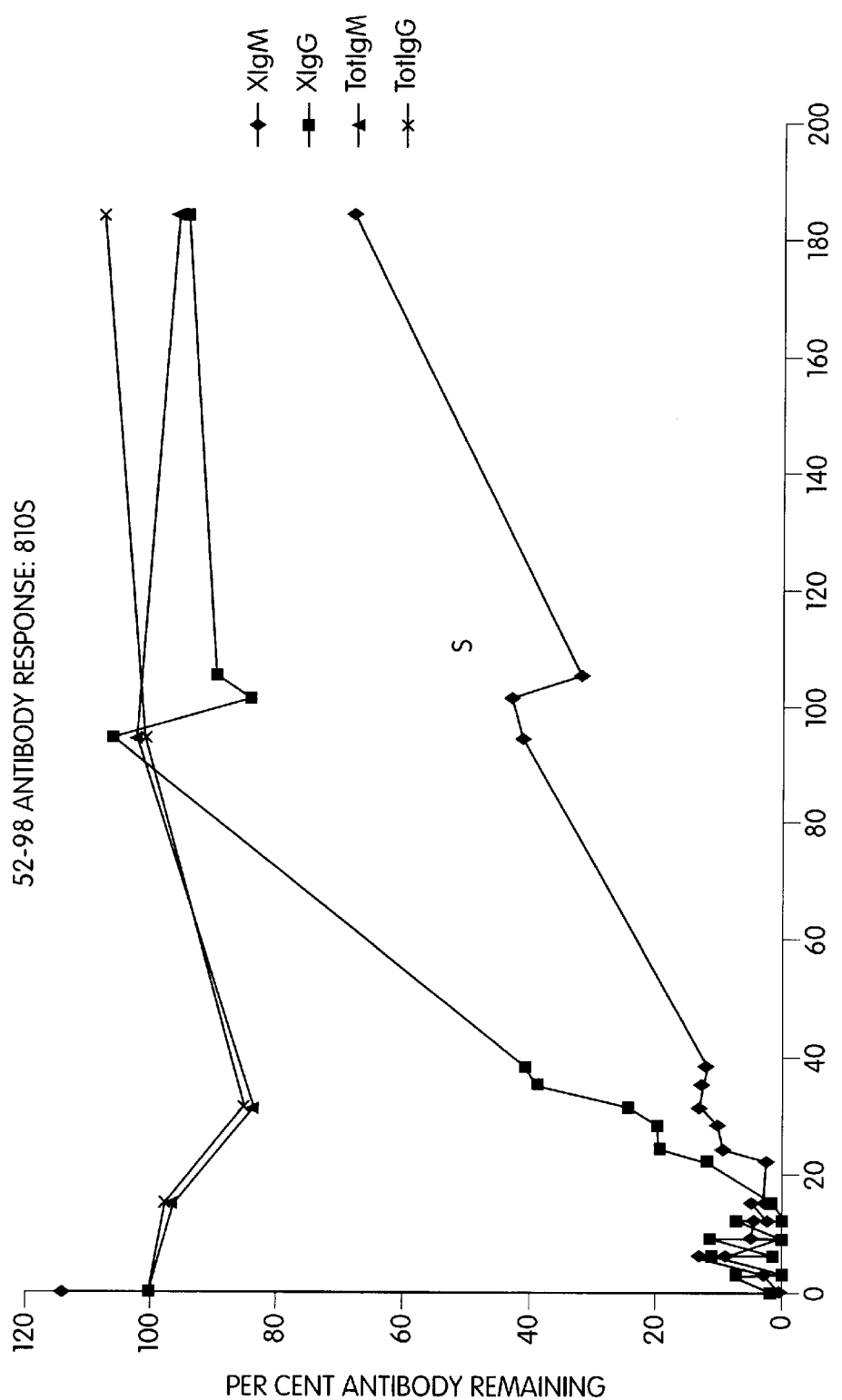
FIG. 29 is a graph of baboon 52–98 antibody response to 810S. Baboon 52–98 was treated with 810S (50 mg/kg) every 3 days for a total of 6 treatments. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.
Figure 30:
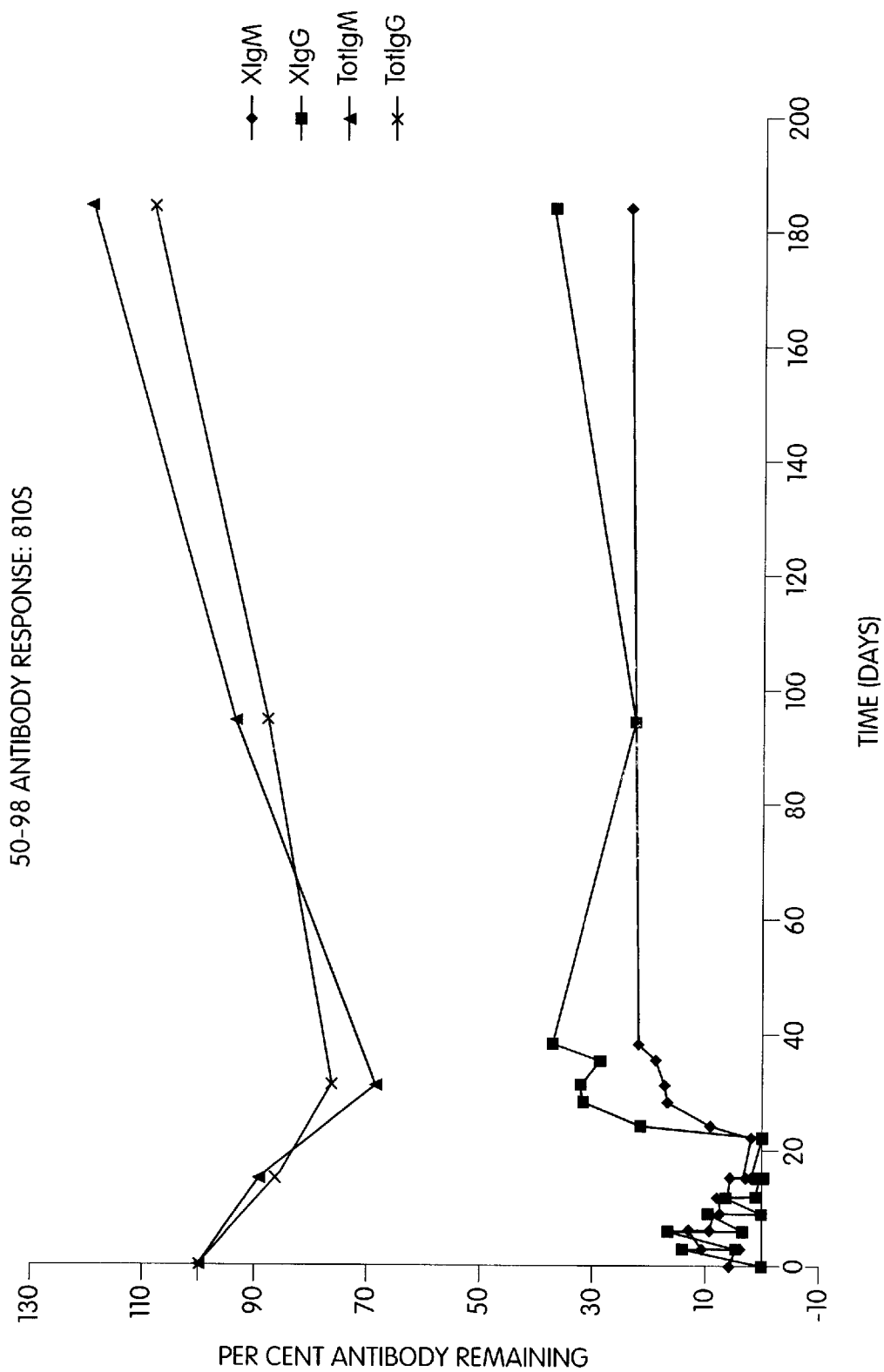
FIG. 30 is a graph of baboon 50–98 antibody response to 810S. Baboon 50–98 was treated with 810S (50 mg/kg) every 3 days for a total of 6 treatments. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.

A preferred composition of the invention is a polymer derived from the reaction of a polymer backbone comprising a plurality of nucleophilic or electrophilic functional groups with a xenoantigen comprising a functional group capable of reacting with the functional groups presented on the structural backbone in the presence of a reagent capable of activating one set of the aforementioned functional groups for reaction with the other set of functional groups, all in the presence of a crosslinking reagent (see FIG. 25). In certain embodiments, the complementary pairs of functional groups are selected from the group consisting of amine/carboxylic acid, alcohol/alkyl halide or sulfonate, thiol/alkyl halide or sulfonate, phosphine/alkyl halide or sulfonate, phosphite/alkyl halide or sulfonate, and aldehyde or ketone/amine. Suitable complementary pairs of functional groups are those that produce a linkage between the antigen and the scaffold that is robust under physiological conditions, e.g., an amide, ether, thioether, or phosphate. In certain embodiments, the linkage between the scaffold and the antigen comprises an amide moiety.

The activating reagent, i.e., the reagent that facilitates the formation of the covalent bond between the scaffold and the xenoantigen, is any reagent capable of activating a nucleophilic or electrophilic functional group for reaction with a complementary electrophilic or nucleophilic functional group to form a new covalent bond. In certain embodiments, the activating reagent is a dehydrating agent, diimide, Bronsted acid or base, Lewis acid or base, acyl halide, or phosphoryl halide. In certain embodiments, the activating reagent is a diimide, e.g., dicyclohexyldiimide [DCC] or ethyl-3-(dimethylamino)propyldiimide [EDC]. In certain embodiments, the activating agent is EDC.

In preferred embodiments the composition has a structural backbone comprising a non-immunogenic, pharmacologically-acceptable scaffold, e.g., polyethylene glycol bearing multiple nucleophilic or electrophilic functional groups. The scaffold is preferrably in the molecular weight range of 1,000 Da to 100,000 Da, more preferably in the range of 3,000 to 70,000 Da, most preferably in the range of 5,000 to 30,000 Da. However, as described in the appended examples, the molecular weight of the final polymeric product can be much larger, primarily due to cross-linking of the scaffold units.

The nucleophilic or electrophilic functional groups on the scaffold are selected from the group comprising amines, alcohols, thiols, selenols, phosphines, aldehydes, ketones, acid chlorides, acids, esters, alkyl halides, and alkyl sulfonates. In certain embodiments, the functional group on the scaffold is an amino or carboxylate moiety, and the functional group comprised by the antigen reacts therewith to form an amide linkage.

The antigen of the present invention may comprise a carbohydrate, peptide, glycopeptide, lipid, or any small organic or inorganic moiety known to be xenoantigenic, i.e., presented by the xenograft and antigenic to the subject's immune system. Xenoantigenic groups can be readily identified by methods well known in the art. For instance, XNAs from human blood can be isolated by perfusing the blood over xenograft material, isolating from the graft those XNAs which specifically bound to it, and using those antibodies to screen candidate epitopes, e.g., by immunoassay. In certain embodiments, the antigen is an oligosaccharide, oligopeptide or glycopeptide.

It has been observed that human xenoreactive antibodies can be polymorphic with respect to binding specificity for oligosacchrides including the αGal(1,3)Gal epitope, e.g., including species which bind to di-, tri-, tetra-, penta- and high order oligosacchrides including the αGal(1,3)Gal moiety. Thus, in certain embodiments, the invention contemplates xenoantigen-polymers derived with αGal(1,3)Gal terminated oligosaccharides, e.g., including from 1–10 saccharide residues, more preferably 1–5 saccharide residues.

αGal oligosaccharides of the invention include those saccharide compositions comprising two or more saccharide moieties in which a galactose moiety is joined by an α(1,3) glycosidic linkage to another galactose moiety. In preferred embodiments the αGal motif (Galα1–3Gal) is located within 15, 10, 5, 4, 3, 2, or 1 saccharide unit(s) from the non-reducing end of the oligosaccharide. In a most preferred embodiment, the αGal motif represents the terminus (i.e., the non-reducing end) of the oligosaccharide. The αGal oligosaccharides may comprise one, or a plurality of αGal motifs. For example, the αGal oligosaccharide may be a branched carbohydrate having multiple terminal Galα1–3Gal residues or a linear oligosaccharide containing both terminal and internal Galα1–3Gal residues. To further illustrate, the subject polymers can include xenoantigens represented by the general formula (I):

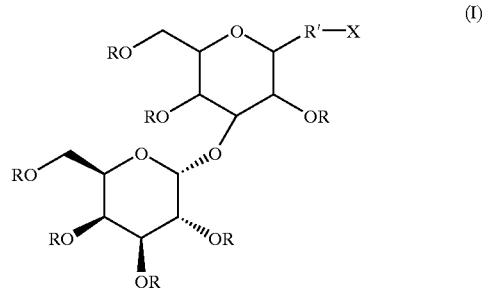

(I)

wherein: R, independently for each occurrence, represents H or a $C_1$–$C_6$ alkyl or other hydroxyl protecting group, and more preferably represents H for each occurrence; R' is absent or represents an oligosacchride, e.g., having from 1–8 saccharide residues; and X represents a bond or linker moiety linking the oligosacchride moiety to the polymer backbone.

Certain experiments have indicated the strongest binding of human xenoreactive antibodies to oligosaccharides with an α-galactosyl terminal residue included the oligosaccharides αGal(1,3)Galβ, αGal(1,3)Galβ(1,4)GlcNAcβ and αGal(1,3)Galβ(1,4)Glcβ. See, for example, Cooper et al. (1994) *Immunol Rev* 141:31. Thus, in certain embodiments, the xenoantigen is represented by the general formula (II):

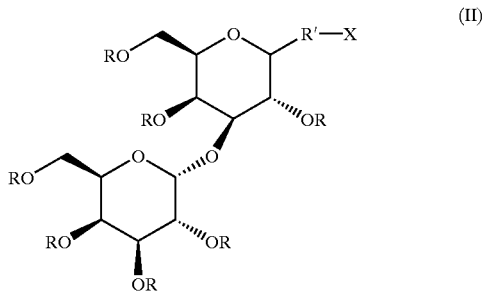

(II)

wherein R and R' are as defined above.

In other embodiments, the xenoantigen and an αGal terminating saccharide or oligosaccharide, e.g., represented in one of the general formulas (III–VI):

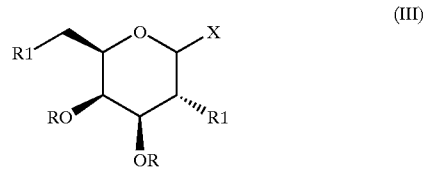

(III)

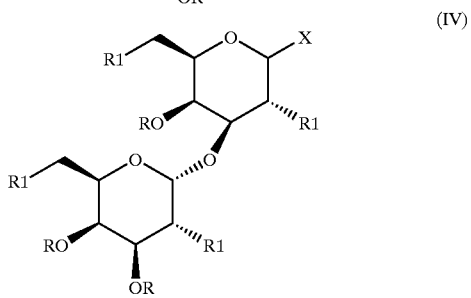

(IV)

-continued

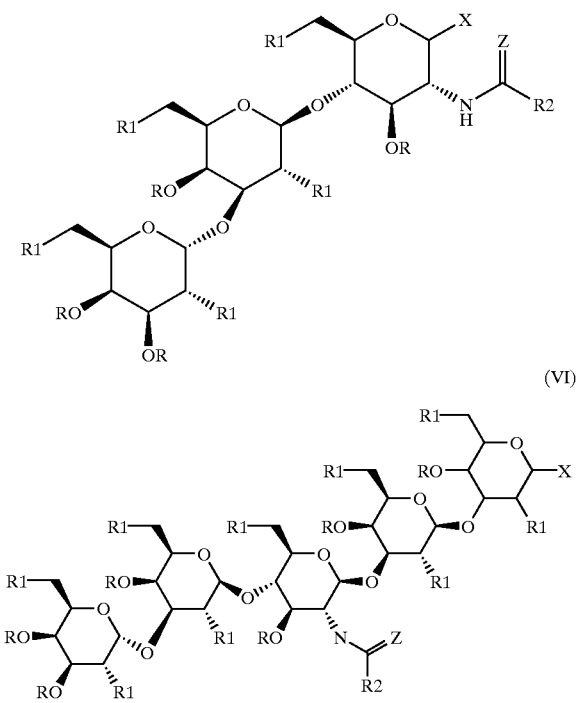

wherein,
R1, independently for each ocurrence, is H, —OR, —SR or —N(H)—Y—R;
R, independently for each occurrence, represents H or a $C_1$–$C_6$ alkyl or other hydroxyl protecting group, and more preferably represents H for each occurrence;
R2 is a $C_1$–$C_6$ alkyl, and more preferably represents $CH_3$;
Y, independently for each ocurrence, is absent, or —C(S)—, —S(O)$_2$—, —C(O)—A—;
X represents a bond or linker moiety linking the oligosacchride moiety to the polymer backbone;
Z is O or S; and
A is —NH—, —NH—($C_1$–$C_6$ alkyl)-, —NH—($C_1$–$C_6$ alkenyl)-, —O—, —O—($C_1$–$C_6$ alkyl)-, —O—($C_1$–$C_6$ alkenyl)-, —S—, —S—($C_1$–$C_6$ alkyl)-, —S—($C_1$–$C_6$ alkenyl)-.

In preferred embodiments, the αGal oligosaccharides of the invention comprise a saccharide sequence corresponding to the antigenic glycolipid expressed on pig endothelial cell membrances, e.g., vascular endothelial or other endothelial tissue of heart, kidney, liver or lung tissue. Such αGal oligosaccharides include, but are not limited to Galα1–3Gal; Galα1–3Galβ1–4GlcNAc; Galα1–3Galβ1–4GlcNAcβ1–3Gal; and Galα1–3Galβ1–4GlcNAcβ1–3Galβ1–4Glc.

Other exemplary oligosacchrides for incorporation in the subject xenoantigen-polymers are shown in FIGS. 14–23.

Moreover, while findings in the art indicate that most human xenoreactive IgM and some human xenoreactive IgG is specific for the αGal(1,3)Gal epitope, some human xenoreactive antibodies directed against other determinants may also be responsible for hyperacute rejection. See, for example, Parker et al. (1995) Transplant Immunol 3:181; Ye et al. (1994) Transplantation 58:330; and Collins et al. (1994) Xenotransplantation 1:36. Thus far, in addition to the αGal(1,3)Gal epitope, several other pig carbohydrate epitopes have been identified as immunoreactive with natural antibodies in human serum, including αGal(1,2)Gal, αGal(1,4)Gal, βGal(1,3)GalNAc and 3-O-sulphated galactose (SO4-3Gal), each of which can be used as a xenoantigen for incorporation into the subject polymers. See, e.g., Holgersson et al. (1990) J Biochem 108:766; Holgersson et al. (1991) Glycoconj J 8:172; and Good et al. (1:992) Transplant Proc 24:559. Others report oligosaccharide epitopes for human xenoreactive antibodies as including A or A-like carbohydrates (namely A disaccharide, A trisacchride, A tetrasacchrides and linear A type 6), Forssman disaccharide and trisaccharide, α-L-rhamnose and rhamnose-containing oligosaccharides, and βGlcNac-containing oligosacchrides. See, Cooper et al. (1993) Transplan Immunol 1:198; and Good et al. (1992) Transplan Proc 24:559. The possibility of other carbohydrate xenoantigens is also suggested by the fact that other species such as the pig, goat, dog, rat, etc—which do not produce anti-(αGal (1,3)Gal antibodies—have xenoreactive natural antibodies which presumably recognize other epitopes. Cameron et al. (1983) J Surg Oncol 22:157. Accordingly, the subject xenoantigen-polymers can be generated using xenoantigenic oligosaccharides other than αGal, e.g., which are cross-reactive with natural human xenoreactive antibodies.

Examples of modified αGal oligosaccharides (i.e., derivatives) also encompassed by the invention include, but are not limited to, salts and sulfate substitutes of αGal oligosaccharides, as well as αGal oligosaccharides in which one or more or the pyran rings has been substituted with a piperidine ring system and/or a tetrahydrothiopyran ring system.

αGal oligosaccharide aza sugars in which the oxygen of one or more of the pyran rings of the oligosaccharide is replaced with nitrogen to form a piperidine ring system may be prepared by enzymatic methods known in the art using the appropriate aza saccharide as the acceptor substrate. Alternatively, aza sugar donor moieties may be transferred by the corresponding glycosyltransferase for the natural sugar. Aza glucose can be isolated from natural sources and converted to the aza lactose by the action of a galactosyltransferase in the presence of a galactose donor such as for example, UDP-galactose.

The polymeric composition of the invention may also include αGal oligosaccharide thio sugars, e.g., in which the is oxygen of one or more of the pyran rings of the oligosaccharide is replaced with sulfur to form a tetrahydrothiopyran ring system. The monothiosaccharide may be prepared by known organic chemical techniques from the corresponding monosaccharide and the αGal oligosaccharide derivative thio sugar may be prepared applying enzymatic methods and using the appropriate thio saccharide as the acceptor substrate.

Those skilled in the art will readily appreciate that libraries of oligosaccharides can be readily generated, and the ability of individual members of the library, alone or displayed on a polymer, to bind to human xenoreactive antibodies can be readily assessed. Moreover, such libraries can be used to identify oligosaccharides which selectively bind xenoreactive antibodies, but which are not substantially immunoreactive with human (or other host) antibodies for, e.g., bacterial carbohydrate epitopes. In such a manner, the xenoantigen(s) of subject polymers can be optimized.

In certain embodiments, the subject polymers can be derived such that single molecules of polymer simultaneously display two or more different xenoantigens. In other embodiments, the polymeric compositions can be a mixture of different, discrete xenoantigen-polymers to provide a broader spectrum of XNA-neutralizing activity.

In this regard, McKane et al. (1998) *Transplantation* 66:626 describe a neoglycoprotein enzyme-linked immunosorbent assay to probe the precise antigenic requirements for the binding of anti-(αGal(1,3)Gal epitopes in human sera. Their study revealed antibody heterogeneity amongst the population. In that study, nearly two-thirds of the individuals had IgG that recognized αGal(1,3Gal) di-, tri-, and pentasaccharides (D, T, and P, respectively), termed "DTP phenotype". The frequency of other phenotypes was ——-P, 13%; -TP, 12%; D-P, 8%; and DT-, 1%. In light of the polymorphism in the anti-(αGal(1,3) Gal repertoire, the subject method can include a step of determining the anti-(αGal phenotype of the patient, and administering a xenoantigen-polymer of the present invention which includes αGal oligosaccharides, e.g., di-, tri-, tetra and pentasaccharides, in a ratio which is determined by the phenotype of the individual to be treated, e.g., wherein the ratio approximates the phenotypic ration of anti-(αGal antibodies.

In other embodiments, the xenoantigen is a protein, or peptidyl portion thereof, which competes with a xenograft for human xenoreactive antibodies. Anti-pig antibodies, for example, have been identified to bind to protein components on the surface of the graft. For instance, HLA-specific antibodies in highly sensitized patients can cause a positive crossmatch against pig lymphocytes. Taylor et al. (1998) *Transplantation* 65:1634.

The crosslinking agent used to generate the subject polymers will preferably include at least two functional groups capable of reacting with the scaffold, the antigen, the functional group formed by the covalent linkage of the scaffold with the antigen, or any or all of them. In certain embodiments, the crosslinking agent is sterically or electronically predisposed, or both, to crosslinking as opposed to reacting with two sites within the same molecule (actually not a crosslinking reaction, but rather a cyclization reaction). In certain embodiments, the crosslinking agent is generated in situ from a precursor. In preferred embodiments, the crosslinking agent (48; wherein X represents a leaving group) is generated in situ from N-hydroxysulfosuccinimide (47).

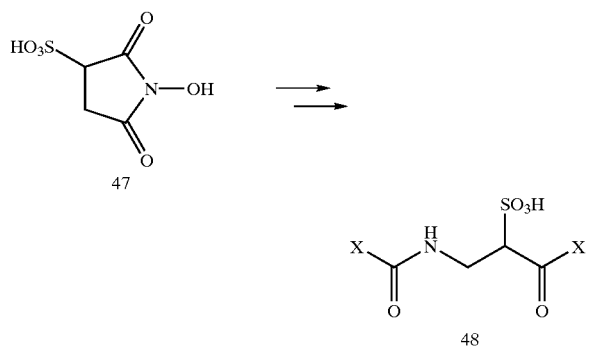

While not wishing to be bound by any particular theory, in certain embodiments, Applicants believe that the crosslinking agent reacts with the amide linkages formed by the reaction of amines on the scaffold with carboxylates on the antigens; crosslinking agents represented by 48 are particularly effective in these embodiments. In certain embodiments, the average molecular weight of the oligomers is proportional to the reaction time even though all of the functional groups on the scaffolds react with functional groups on the antigens within the first fifteen minutes of the reaction time. The significance of molecular weight is discussed infra. In these embodiments, crosslinking continues after formation of the covalent bonds between the scaffolds and antigens is complete.

The polymers of the present invention may be synthesized in a single chemical reaction, i.e., by including all necessary reagents in a single reaction vessel, or they may be synthesized in two or more chemical reactions conducted in series. When the polymers of the present invention are synthesized via a series of reactions the intermediate compounds may be purified before being subjected to the next reaction in the series, or they may be used without purification. In certain embodiments, chemical reactions conducted in series may be completed in a single reaction vessel, e.g., by allowing a certain group of reagents to react in the vessel for a desired period, followed by introduction into the vessel of the reagents required for the next reaction in the series. In certain embodiments, the products obtained via these various approaches will comprise the same molecular components, but will differ in their properties or activity in a subject or assay due to differences in their microscopic structures, e.g., the degree of crosslinking, or the identities, locations or ratios of the functional groups involved in the crosslinks. One of ordinary skill in the art will be able to ascertain using no more than ordinary experimentation the reaction protocol and conditions necessary to produce a product of the present invention with properties optimized for a specific assay or subject.

Thus, the polymer may include a polymer backbone comprised of polyethylene glycol (PEG) subunits, some of which have attached thereto a saccharide moiety represented in the general formula (VII):

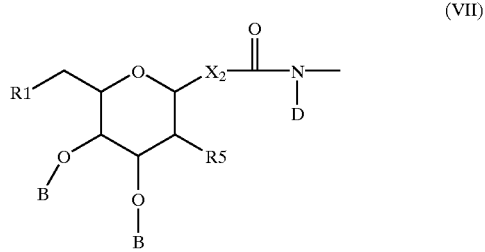

wherein,

R1, independently for each ocurrence, is H, —OR, —SR or —N(H)—Y—R;

R5 is H, —OR, NH—Y—R2, or —L—E;
  Y independently for each occurrence is absent, —C(O)—, —C(S)—, —C(NR)—, O, S, or Se;

B, for one occurrence is —R, and for the other occurrence is —R or from 1–9 saccharide residues;
  R, independently for each occurrence, represents H or a $C_1$–$C_6$ alkyl or other hydroxyl protecting group, and more preferably represents H for each occurrence;

R2 is a $C_1$–$C_6$ alkyl, and more preferably represents $CH_3$;

X2 represents a linker of 1–10 atoms in length, preferably —O-alkyl, more preferably —O—$(CH_2)_5$—;

D represents H, or —L—E;
  L represents a linker a linker of 1–20 atoms in length, preferably

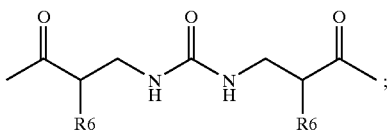

R6 is H or SO$_3$;

E represents a second PEG subunit of the polymer, wherein, independently for each occurrence of E, the linker group L is covalently attached via R5 or B of a saccharide moiety of the second PEG subunit, or via an amine of the second PEG subunit.

For example, the polymer may be represented by the general formula

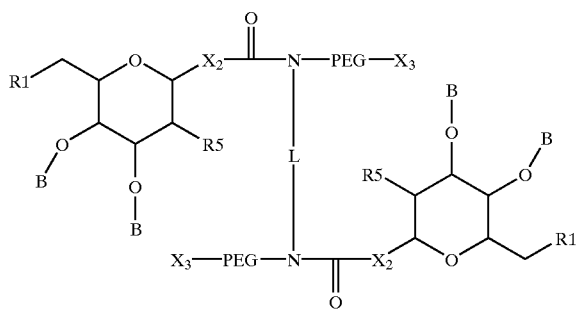

wherein R1, R5, X2 and L are as described above, and

PEG represents a polyethylene glycol (PEG) subunit of the polymer; and

X3 represents one or more additional PEG subunits of the polymer, each of which may be derivatived with a saccharide moiety of formula VII, wherein the polymer has an average molecular weight in the range of 10,000 daltons to 1,000,000 daltons.

An exemplary composition of the invention is derived from an octa(amino)polyethylene glycol scaffold to which several αGal(1,3)Gal moieties are linked via a covalent tether, wherein the individual molecules of the scaffold bearing the disaccharide moieties are crosslinked to yield an oligomeric material comprising two or more scaffold-disaccharide molecules.

In general, the reactions of the polyamino-PEG scaffold with oligosaccharides will be carried out in the pH range of 4 to 7, and most preferably in the pH range of 5–6. The preferred temperature range for the reactions is between 0° C. and 40° C., and more preferably is in the range of 4° C. to 27° C. Examples 23 and 26 highlight the relationship between the pH and reaction temperature and the activity of the composition produced.

A polar, protic or aprotic solvent may be used. As described in the examples, the reactions can be run in aqueous solutions. Alternatively polar, aprotic solvents such as αnitrogen-dialkyluted carboxymide, lactum, sulfoxide or sulfore, as for example dimethyl formamide, may be used. In those instances, the reactions may be effected without or with the additions of water, for example, up to quantities at which the polymer remains in solution. Non-limiting examples of preparations are discussed in the examples.

As described in the examples, the molecular weight of the resulting polymer can depend on such factors as reaction time, pH, temperature and reactant concentrations. In those instances wherein the resulting xenopolymer is to be used for depletion of xenoreactive antibodies, larger molecular weight polymers may be used, e.g. polymer compositions having an average molecular weight of 100,000–1,000,000 daltons, though more preferable in the range of 100,000–500,000 daltons, and even more preferably 300,000–500,000 daltons.

However, when the resulting xenopolymer is to be used at least in part as a tolerogen, e.g. to induce tolerance or anergy to the xenoantigens, it will be preferable to employ polymer formulations at lower molecular weight, e.g. having an average molecular weight of 10,000–300,000 daltons, more preferably having an average molecular weight less than 100,000 daltons, e.g., 25,000–100,000 daltons. Such lower molecular weight polymers, even if not tolerogenic, will have reduced immunogenic activity.

Moreover, suitable tolerogenic compositions according to this aspect of the invention can be identified according to the following criteria. First, they are preferably non-immunogenic when administered to a primate, including a human. As a practical matter, this can be evaluated by comparing the level of antibodies specific for a candidate polymer in peripheral blood of a primate, including a human, prior to and after administration of the candidate polymer.

Tolerogenic compositions according to this aspect of the invention may also include pharmaceutically acceptable carriers, diluents, and/or controlled release agents. Certain non-limiting examples of such carriers, diluents and/or controlled release agents include buffered saline, oils, implantable pumps and encapsulated beads.

Moreover, in certain instances, such as for formulations of the polymer for human therapeutic use, it will be desirable for the composition to be relatively homogenous with respect to polymer size. That is, the polymers can be formulated to have narrow molecular distributions or polydispersity, as defined by the ratio Mw:Mn, where Mw is the weight average molecular weight of the polymer and Mn is the number average molecular weight of the polymer. Thus, in certain preferred embodiments, the subject polymer compositions will have a polydispersity, for the xenopolymer, of 20 or less, more preferably 10 or less, and even more preferably 5 or less.

In certain embodiments, the subject method for generating the xenopolymers of the present invention is part of an overall method for manufacturing a medicament. Thus, the xenopolymer is formulated with one or more pharmaceutically acceptable excipients, such as described below, in an amount and concentrations to provide at least the efffective dose (ED$_{50}$) for depleting xenoreactive antibodies in the patient, inducing tolerance or anergy to the xenoantigen. For instance, the polymer can be formulated such that, for its mode of delivery, a dose of at least the ED$_{50}$ for inhibitions of HAR can be administered to the patient.

In preferred embodiments, the factor VIII-polymers have a therapeutic index of at least 10, and more preferably at least 100, 1000, or even 10,000, for the particular mode of administration.

As part of a process for preparations of a medicament of the present inventions, the polymer can be synthesized and handled under sterile conditions, or can be sterilized prior to formulation. Likewise, contaminants can be removed, including the unreacted reactants and synthesis by-products. The resulting medicament should be sterile, and substantially free of pyrogenic or other toxic contaminants.

In a first preferred synthetic method, a branched polymer having at least three arms and at least six covalently linked active groups such as amino or hydrazino groups is reacted in the presence of N-(3-dimethlyaminopropyl)-N'-ethylcarbodiimide (EDC) with Gal α 1–3 Gal having a covalently linked carboxy group. In a second preferred method, the converse of the first method, the branched polymer has covalently linked carboxy groups while the Gal α 1–3 Gal has a covalently linked amino or hyrazino group.

In a third preferred method, the branched polymer has at least three arms and at least six active groups such as amino or hydrazino groups, and the αGal(1,3)Gal has a covalently linked aldehyde group. In a fourth preferred method, the converse of the third method, the branched polymer has at least six aldehyde groups while the αGal(1,3)Gal has a covalently linked amino or hydrazino group. In the third and fourth methods, EDC is not required for the reaction to take place.

In a fifth preferred synthetic method, the branched polymer has at least three arms, with at least three active groups such as amino or hydrazino groups covalently linked to the free ends of the arms, and the αGal(1,3)Gal has a covalently linked carboxy group. In a sixth preferred method, the converse of the fifth method, the branched polymer has at least three covalently linked carboxy groups while the αGal(1,3)Gal has a covalently linked amino or hydrazino group. The fifth and sixth methods are conducted in the presence of EDC and N-hydroxysulfosuccinimide (NHSS). The compositions resulting from the fifth and sixth methods have a covalently linked activation group which is N-hydroxysulfosuccinimide.

"Mixed arm" syntheses can also be conducted with all sorts of combinations of groups on the ends of the arms, for instance 7 amino/1 carboxy, or 5/3, or 4/4. Given the guidance of the experimental examples below, one of ordinary skill in the art of chemical synthesis will be able to devise various combinations of reagents that will yield functional compositions within the scope of the present invention.

Figure 3:
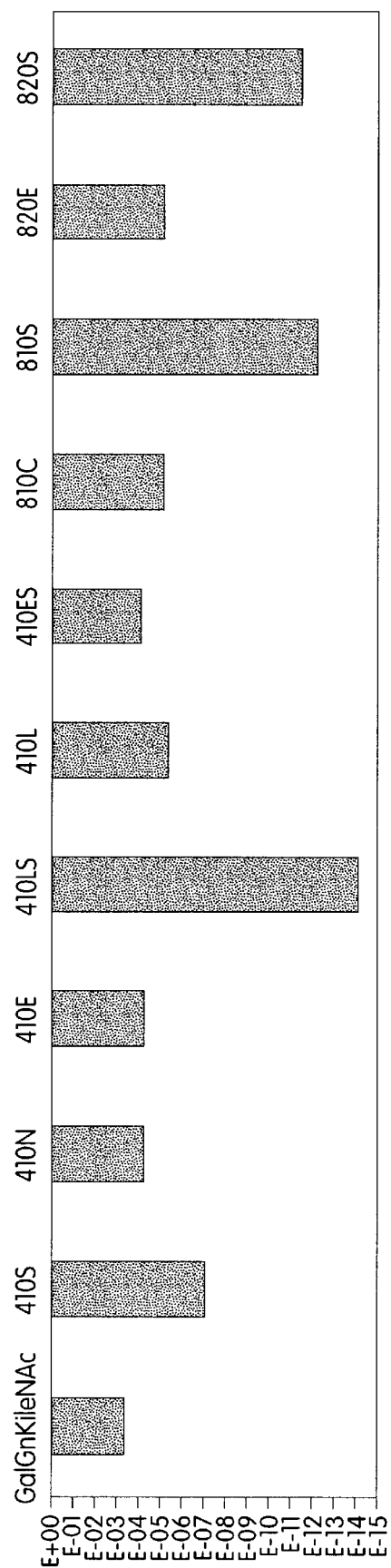
FIG. 3 shows the concentration of various compositions required for 50% inhibition of xenoreactive antibody activity.

Various compositions of the invention are designated in FIG. 3 and throughout according to the following nomenclature:

The letter E denominates a synthesis that used only EDC for coupling.

The letter N denominates a synthesis that used both EDC and N-hydroxysuccinimide (NHS).

The letter S denominates a synthesis that used both EDC and N-hydroxysulfosuccinimide (NHSS).

The letter L denominates a lysine coupled to the ends of branched PEG-amino, and EDC for coupling.

The letters LS denominate a synthesis that used lysine and NHSS.

The letters ES denominate a synthesis that used EDC for coupling and a sulfo group coupled to the PEG starting material.

The first number in the numbering system denominates the number of branches on the PEG, and the second number (10 or 20) denominates the molecular weight of the starting PEG-amine (10,000 or 20,000 Da).

The product of the synthesis 410L proved to be 100 times more effective per coupled sugar than the free sugar ($IC_{50}$= 0.5 mg/mL for 410L versus 50 mg/mL for the free sugar). Surprisingly, the compositions which were synthesized using N-hydroxysulfosuccinimide (NHSS; NHS with a sulfo group) achieved 50% inhibition of anti-Gal antibody reactivity at very low concentrations of approximately $10^{-5}$ mg/mL to $10^{-7}$ mg/mL. Moreover, these compositions were stable for 12 months when stored at a pH in the range of 4 to 7 at temperatures ranging from 1–10° C.

In other exemplary embodiments, the subject xenopolymer is formed by derivatizing an aminodextran with the xenoantigen. In an illustrative process for preparing a xenoantigen-conjugate with an aminodextran, one can begin with a dextran polymer. The dextran is reacted with an oxidizing agent to effect a controlled oxidation of a portion of its carbohydrate rings to generate aldehyde groups. The oxidation is conveniently effected with glycolytic chemical reagents, e.g., $NaIO_4$, according to conventional procedures. The oxidized dextran is then reacted with a polyamine, such as a diamine. Suitable amines include, e.g., ethylene diamine, propylene diamine or similar polymethylene diamines, diethylene triamine or like polyamines, 1,3-diamino-2-hydroxypropane or other like hydroxylated diamines or polyamines, and the like. Reductive stabilization of the resultant intermediate is effected by reacting the Schiff base intermediate with a reducing agent, e.g., $NaBH_4$, $NaBH_3CN$, or the like. The resultant adduct can be further purified by passage through a conventional sizing column to remove cross-linked dextrans. An estimate of the number of available primary amino groups on the aminodextran can be effected by reaction of a weighed sample with trinitrobenzenesulfonic acid and correlation of the optical density at 420 nm with a standard. Alternatively, the dextran can be derivatized by conventional methods for introducing amine functions, e.g., by reaction with cyanogen bromide, followed by reaction with a diamine.

Other polyamines which can be utilized in the xenopolymers of the present invention include the non-antigenic amine derived polymers of the Greenwald et al. U.S. Pat No. 5,730,990, and the non-antigenic branched polymer conjugates of the Martinez et al. U.S. Pat. No. 5,643,575.

B. Assays For Competitive Inhibition of αGal XNA

Quantification of circulating anti-(αGal antibodies in the serum of an individual and the ability of polymers to remove, bind, and/or neutralize anti-(αGal antibodies can be routinely determined applying immunoassays known in the art which may be routinely adapted for such determination. Such immunoassays, include, but are not limited to, competitive and noncompetitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays (e.g., hemagglutination), complement-fixation assays, immunoradiometric assays, fluorescent immunoassays and protein A immunoassays. These assays may further be applied to determine the dosage of the αGal oligosaccharide polymers of the invention to be administered, as well as to monitor the neutralization and/or removal of anti-(αGal antibodies by the αGal oligosaccharide polymers of the invention.

While assays for measuring circulating anti-(αGal antibodies can be accomplished by various immunological methods, ELISA assays have the advantage in that they can be standardized for the immobilized ligand, are reproducibly quantitative, and can be scored for different immunoglobulin isotypes by the use of appropriate secondary detection reagents. ELISA capture ligands for testing human or old world monkey serum antibodies can employ fixed cells, glycolipids, glycoproteins, or oligosaccharides. Such capture ligands include but are not limited to mouse laminin, PK-15 pig kidney cells, immobilized BSA-αGal neoglycoconjugates, and immobilized αGal oligosaccharides. Covalent immobilization of a specific αGal oligosaccharide(s) onto the ELISA immobilized surface, using techniques known in the art, permits the predetermined deposition of known antigenic ligands by covalent chemistry. In addition to determining the ability of the αGal oligosaccharides polymers to bind to and/or neutralize anti- (αGal antibodies, such an ELISA is also useful in clinical monitoring of anti-(αGal antibodies in blood of patients in advance of, and following xenotransplantation of organs from animals that express the αGal epitope.

The addition of serial dilutions of sera in the ELISA assays permits the determination of reactive antibody titers, which can serve to quantitate the circulating anti-(αGal activity. Specific immunoglobulin isotypes can be monitored by using appropriate reagents, e.g., anti-human IgG or IgM.

In another embodiment, quantification of anti-(αGal antibodies and/or the extent of xenoreactive antibody neutralization or removal upon treatment with the αGal oligosaccharide polymers of the invention is measured using a cell cytotoxicity assay. Such an assay may comprise contacting serum, isolated from a patient using techniques known in the art, with αGal expressing cell monolayers (e.g., pig kidney cells (PK-15), pig aortic endothelial cells, or mouse aortic endothelial cells (MAE). Preferably, these cells are from the same species as the donor of the xenograft, and most preferably from the same tissue-type as the tissue to be transplanted). According to this assay, cytotoxicity is mediated by either endogenous complement, or the sera are heat inactivated (e.g., through heating the sera at 56° C. for 30 minutes) and exogenous complement (e.g., from rabbit or guinea pig) is added. After washing away excess serum, the cells are treated with viable dye mix "live-dead" (calcein AM/ethidium homodimer) which is commercially available in the form of a Live/Dead cytotoxicity kit (Molecular Probes Inc., Eugene, Oreg.) and scored for viability using fluorescence microscopy. Staining with,the "live/dead" dye mix allows for clear distinction between live cells, which show cytoplasmic green fluorescence and dead cells, which show dark cytoplasm land red fluorescent nuclei. The extent of cell lysis that is complement-mediated may be determined by comparing the results observed in the control for which there has been no inactivation of complement, with the lysis observed with complement that has been inactivated through heat treatment.

The invention also encompasses animal-based model systems, which may include baboon, other old world monkeys, or other animals having serum that contains anti-(αGal antibodies. Such animal models may assess the ability of compositions containing an αGal oligosaccharide polymer as an active ingredient to bind to and/or neutralize anti-(αGal antibodies, attenuate the rejection of a xenotransplant expressing the αGal epitope and/or to suppress B lymphocytes expressing anti-(αGal idiotypes. Generally, this assay may involve exposing animal models to the αGal oligosaccharide polymer, or pharmaceutically acceptable derivative as an active ingredient, at a sufficient concentration and for a time sufficient to elicit the desired effect in the exposed animals. The response of the animals to the exposure may be monitored by assessing the level of anti-(αGal reactive antibodies in the serum of the animal, evaluating the appearance of rejections of the xenografted organ, and/or quantitating B lymphocytes expressing anti-(αGal idiotypes. Dosages of test agents may be determined by deriving dose-response curves.

Due to the many similarities between human and baboon immune systems [Neubauer et al., *J. Immunogenetics,* 8:433–442, 1981; Garver et al., *Cytogenetics & Cell Genetics,* 27:238–245, 1980; Brodsky et al., *Immunogenetics,* 155:151–166, 1982; Hammer, C., in Hardy, M. A. (ed.), *Xenograft* 25, 115–123 (Elsevier New York, 1989); Stark et al., *Transplantation* 52(6):1072–1078 (1991); Hammer, C., in Cooper, D. K. C., et al. (eds.), *Xenotransplantation,* 429–438 (Springer-Verlag 1991)], and because of the large size of baboons, these animals are convenient experimental model recipients of pig organs. These non-human primates also express anti-pig antibodies, and reject pig organs hyperacutely [Lexer et al., *J. Heart Transplant,* 4:411–418, 1986; Ye, Y., Cooper, D. K. C., in Cooper, D. K. C., et al. (eds.), *Xenotransplantation,* 389–393 (Springer-Verlang 1991); Cooper et al., *J. Heart Transplant,* 7:238–246, 1988; Platt et al., *Transplantation,* 52(2):214–220, 1991]. As human and baboon immunoglobulins are structurally very similar, some of the anti-idiotypic antibodies against human anti-pig antibodies should bind to baboon anti-pig antibodies and inhibit rejection of pig to baboon xenografts. For instance, Geller et al., *Transplantation,* 55:168–172, 1993, have described an idiotype shared between human and baboon anti-pig antibodies.

Applying these assays, the relative anti-(αGal binding activity that a αGal oligosaccharide polymer exhibits against the anti-(αGal antibody profile of the serum of an individual may be determined, and the polymer formulation best suited for neutralizing and/or binding the anti-(αGal profile of an individual can be determined.

Other methods for assaying the extent of xenoreactive antibody neutralization and/or removal will be known to the skilled artisan and are within the scope of the invention.

C. Formulations

Pharmaceutical compositions comprising the subject xenopolymers, or pharmaceutically acceptable derivatives thereof, can be administered to a patient, preferably a human or old world monkey, by itself, or in pharmaceutical compositions where it is mixed with suitable carriers or excipient (s) at doses to ameliorate symptoms associated with xenograft rejection, prolong xenograft survival in a patient or to direct complement-mediated lytic attack of targeted tissue or cell types.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for the form of administration desired.

The pharmaceutical compositions of the invention may be administered using techniques well known to those in the art. Preferably agents are formulated and administered systemically. Techniques for formulation and administration of the compounds of the invention may be found in "Remington's Pharmaceutical Sciences," 18th ed., 1990, Mack Publishing Co., Easton, Pa., latest edition. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like. The preferred routes of administration are by intravenous infusion, intravenous injection, and intramuscular injection. Dosage forms include but are not limited to tablets, troches, dispersions, suspensions, suppositories, solutions, capsules, gels, syrups, slurries, creams, patches, minipumps and the like. Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained in the form of a solid excipient, optionally by grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils,-liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

D. Illustrative Therapeutic Methods

A preferred method of neutralizing anti-($\alpha$Gal antibodies involves the administration of the subject $\alpha$Gal oligosaccharide polymers, or pharmaceutically acceptable derivative (s) thereof, in sufficient quantity to block binding of the circulating antibody to the donor endothelium and thereby prevent anti-($\alpha$Gal antibody directed complement-mediated lytic attack of the transplanted tissue.

It is a primary object of this invention to provide a method and associated compositions for attenuating xenograft rejection or to alleviate trauma caused by anti-($\alpha$Gal antibody directed complement activation by interfering with anti-($\alpha$Gal antibody binding to cell surfaces, in particular donor organ endothelium. Accordingly, the pharmaceutical compositions of the invention may be administered alone, together with, or in seriatim with other therapy regimens for reducing the extent of binding of anti-($\alpha$Gal antibody to donor organ cells or tissue.

In a specific embodiment, the therapeutic method of the invention is carried out as monotherapy, i.e., as the only agent provided for attenuating xenograft rejection.

In another embodiment, administration of the αGal oligosaccharide polymer of the invention is combined with other regimens that may accompany neutralization and/or depletion of anti-(αGal antibodies using the subject αGal oligosaccharides polymers, including, but not limited to, extracorporeal treatment with column immobilized human antianimal idiotypic antibodies (for example, see U.S. Pat. No. 5,560,911), plasmapheresis (in which all antibodies or specifically, one or more antibody types specific for antigenic epitopes on the surface of donor endothelial cells have been removed from the plasma) and perfusion of blood to be administered to the patient through organs, tissue or cells expressing αGal antigens (such as, for example, hearts, kidneys, erythrocytes, and cell lines derived from pig kidney, pig aortic endothelium, mouse endothelium, etc.).

Depletion of circulating anti-(αGal antibody is a temporary solution, which can overcome the HAR crisis. But the antibody-producing B lymphocytes continue to produce antibody, which can pose a danger of longer-term antibody-mediated vascular rejection. These B lymphocytes bear on their membrane surface immunoglobulin with the αGal-binding domain exposed (Geller et al. (1993) *Transplantation* 55:168172). In certain embodiments, the subject polymer is selected for its ability to induce clonal tolerance to the xenoantigen. In such embodiments, the polymer can also be used in a step for neutralizing and/or depleting circulating XNAs. In other embodiments, the subject polymer can be used principally as a tolerogen, and circulating XNAs can be removed by immunoaphoresis or other regimen for antibody removal.

E. Conjoint Therapies

The xenopolymers of the present invention may be administered alone or in combination with other agents useful in attenuating xenograft rejection, including conventional nonspecific immunosuppressive agents, including but not limited to, steroids, cyclosporine, cyclosporine analogs, cyclophosphamide methylprednisone, prednisone, azathioprine, FK-506, 15-deoxyspergualin, and other immunosuppressive agents known in the art. In a further embodiment, the pharmaceutical compositions comprise an antibiotic agent selected from the group consisting of tetracycline, metronidazole, amoxicillin, P lactamases, aminoglycosides,, macrolides, quinolones, fluoroquinolones, cephalosporins, erythromycin, ciprofloxacin, and streptomycin. In an additional embodiment, the pharmaceutical composition comprises an anti-inflammatory. Such anti-inflammatories include, but are not limited to, glucocorticoids and the nonsteroidal anti-inflammatories,aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, c-acetamidocaproic acid, Sadenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the agents given first, followed by the second.

In certain embodiments, the administration of the subject xenopolymers can be part of a treatment regimen which includes total-body irradiation and splenectomy. See, for example, Cooper et al. (1997) *World J Surg* 21:901.

In certain embodiments, the subject therapies include one or more steps of myeloreductive treatment, especially where the xenograft is bone marrow or other hematopoietic stem cell preparations. Such a method may include, e.g., treating the subject, prior to introduction of the donor stem cells, with an cytoreductive agent selected from one or more of alkylating agents (e.g., nitrogen mustards [such as mechloretamine], cyclophosphamide, melphalan and chlorambucil), alkyl sulphonates (e.g., busulphan), nitrosoureas (e.g., carmustine, lomustine, semustine and streptozocine), triazenes (e.g., dacarbazine), antimetabolites (e.g., folic acid analogs such as methotrexate), pyrimidine analogs (e.g. fluorouracil and cytarabine), purine analogs (e.g., fludarabine, idarubicin, cytosine arabinoside, mercaptopurine and thioguanine), vinca alkaloids (e.g., vinblastine, vincristine and vendesine), epipodophyllotoxins (e.g., etoposide and teniposide), antibiotics (e.g., dactinomycin, daunorubicin, doxorubicin, bleomycin, plicamycin and mitomycin), dibromomannitol, deoxyspergualine, dimethyl myleran and thiotepa.

Preferred myeloreductive non-myeloablative agents are alkylating agents, e.g., cyclophosphamide, or fludarabine or similar substances, however, hematopoietic space creating antibodies or drugs, e.g., inhibitors of cell proliferation, e.g., DSG, or an anti-metabolite, e.g. brequinar, or an anti-T cell antibody, e.g., one or both of an anti-CD4 or anti-CD8 antibody can be used as a myeloreductive non-myeloablative agent.

Other methods for inhibiting T cell activity that may be suitable for use in the methods described herein include:

the administration of anti-T cell antibodies, e.g., an ATG preparation, polyclonal or monoclonal antibody directed against CD4, CD8, or CD2 (an anti-CD2 antibody, e.g., the anti-CD2 monoclonal antibody BTI-322 or a humanized version thereof, or an antibody which overlaps or binds the epitope recognized by BTI-322, are particularly useful);

the administration of an agent, e.g., an antibody, which blocks or otherwise inhibits a pathway, e.g., a costimulatory pathway, of T cell activation (agents, e.g., antibodies, which block the CD28-B7 pathway, e.g., a CTLA4-IgG fusion protein, or agents, e.g., an antibody which blocks the CD40-gp39 pathway, e.g., an anti-gp39 antibody, are particularly suited for use in the method), or generally, by the administration of a treatment which down modulates or otherwise inhibits one or more of the T cell receptor, CD4 co-receptor, CD8 co-receptor or other receptor or co-receptor which promotes T cell activation or maturation;

the administration of an IL-12 receptor protein (functional antagonist, U.S. Pat. No. 5,831,007);

the administration of substituted dihydrobenzofurans, spirobenzofuran-2(3H)-cycloalkanes according to U.S. Pat. No. 5,808,109;

the administeration of anti-asialo antisera;

the administration of an immunosuppressive agent, e.g., a macrolide, e.g., cyclosporine, FK506, or rapamycin; and the administration of thymic irradiation, or other treatment which creates thymic space.

In certain embodiments, the myeloreductive treatment includes treating the subject with an immunosuppressant regimen, prior to introduction of the donor stem cells, in an amount sufficient to prevent rejection of the donor stem cells by the host immune system. For example, such immunosuppressant regimens can include, independently for pre- and post-transplantation is both are carried out, a treatment of the subject which inactivates and/or depletes host T-lymphocytes and/or natural killer (NK) cells in the subject. For example, the immunosuppressant regimen includes treatment with T cell-depleting anti-CD4 and/or CDS antibodies, such as anti-thymocyte globulin (ATG), OKT3, LO-CD2a, or Minnesota anti-lymphoblast globulin (MALG). Preferably, the immunosuprressant regimen, both before and after transplantation, includes administration of ATG.

In other embodiments, the immunosuppressant regimen includes treatment with one or more of a macrolide immunosuppressant, azathioprine, steroids (e.g., prednisone, methyl prednisolone), or sub-lethal nonmyeloablative irradiation of lymphocyte-containing tissue.

In certain embodiments, the method may also include inhibiting natural killer cells of the subject preferably prior to introducing the xenograft, e.g., by introducing into the subject an antibody capable of binding to natural killer cells of the subject. One source of anti-NK antibody is anti-human thymocyte polyclonal anti-serum. A second anti-mature T cell antibody can be administered as well, which inhibits T cells as well as NK cells. Anti-T cell antibodies are present, along with anti-NK antibodies, in anti-thymocyte anti-serum. Repeated doses of anti-NK or anti-T cell antibody may be preferable. Monoclonal preparations can be used in the methods of the invention.

In addition to, or as an alternative to treatment protocols for the receipient, the subject method of administering a xenopolymer can be combined with treatment of the donor and/or donor tissue.

For instance, the xenograft can be treated with glycolytic enzymes prior to implantation in order to reduce the presence of the αGal epitope. The αGal epitopes can be enzymatically removed by specific endo- or exo-glycosidases and mannosidases. Such glycolytic enzymes and general methods for their use are well known in the art. Examples of glycosidases and mannosidases suitable for use in this aspect of the invention include α- or β-galactosidase, β-N-acetylhexosaminidase, α- or β-mannosidase, endoglycosidase H or F, and peptide-N-glycosidase F. These enzymes are all commercially available from Oxford Glycosystems (Rosedale, N.Y.), and are typically used according to the manufacturer's instructions.

Antisense RNAs can be used to specifically inhibit gene expression of, e.g., α1–3-GT activity in the donor animal. In another illustrative embodiments, antisense may be used to reduce the human serum reactivity to porcine endothelial cells by antisense-mediated down-regulation of GpIIIa expression (Kearns-Jonker et al. (1997) *Transplantation* 63:588), and tissue from such animals could be used in combinations with, inter alia, the subject xenoploymers.

Another method to reduce the expression of αGal epitopes would be to perform genetic manipulations referred to in the art as "gene disruption" or "gene knockout". Gene knockout is a method of genetic manipulation via homologous recombination. These techniques may allow for the use of specially designed DNA molecules (gene knockout constructions) to achieve targeted inactivation (knockout) of a particular gene upon introduction of the construction into a cell.

In one embodiment, treatment of a xenograft recipient with the subject polymers may be combined with transplantation of an organ or tissue derived from such transgenic "knockout" animals may be described in, e.g., U.S. Pat. No. 5,821,117 entitled "Xenotransplantation Therapies".

In other embodiments, the subject polymers may be used as part of a treatment regimen for recipients of xenogenic grafts from transgenic animals engineered to express: human decay-accelerating factor, such as may be isolated from the animals described by Cozzi et al. (1994) *Transplant Proc* 26:1402; or which express the human complement regulatory protein CD59 and DAF, as taught by Byrne et al. (1996) *Transplant Proc* 1996 Apr; 28 (2):759; human α1,2-fucosyltransferase, as might be generated according to Chen et al. (1998) *Transplantation* 65:832; a combined transgenic animal expressing of α-galactosidase and α1,2-fucosyltransferase, such as might be produced by the methods of Osman et al. (1997) *PNAS* 94:14677; a combined transgenic animal expressing decay-accelerating factor expression and in which the α1,3-Galactosyltransferase gene is knockout (see, e.g, van Denderen et al. (1997) *Transplantation* 64:882;

(iv) Exemplification

The invention now being generally described will be more readily understood by reference to the following examples which are included merely for purposes of illustration of certain aspects and embodiments of the present invention, and are not intended to limit the invention.

EXAMPLE 1

Synthesis of 410E: 4 Arm 10,000 Molecular Weight, Four Amino Groups (αGal(1,3) Gal β1–GlcNAc)$_4$-Polyethylene Glycol (PEG) Using N-(3-Dimethylaminopropyl)-N'-ethylcarbodiimide (EDC) for Coupling In a 15 mL plastic centrifuge tube, 300 mg of 4 arm, 10,000 molecular weight, PEG-(NH$_2$)$_4$ (Shearwater Polymers, Inc., Huntsville, Ala. 35801), 116 mg of EDC (Pierce, Rockford, Ill. 61105) and 53.4 mg of αGal(1,3)Gal β 1–4 GlcNAc (Cytel Corp., San Diego) were dissolved in 3 mL of DI water. The reaction proceeded for one hour after which an additional 116 mg of EDC was added. The reaction proceeded for an additional 3 hours. The reaction mixture was filled into a dialysis tube of molecular weight cut-off of 3,500 and dialyzed five times against 4 liters of DI water. The dialyzed material was freeze-dried to a white powder. A sample of the freeze-dried powder was dissolved in 20 mL of 0.1M sodium borate and transferred to a 50 mL volumetric flask. 100 ul of TNBS (trinitrobenzene sufonic acid) (Pierce, Rockford, Ill. 61105) was added to the volumetric flask, capped and the flask inverted for mixing. Water was added to 50 mL and the solution was mixed by inversion. The sample was incubated for one hour before reading the OD at 421 nm. The amount of free amino groups was calculated by comparing the OD of the sample to a standard curve generated with glycine as standard. Amino group analysis revealed that more than 98% of amino groups were modified.

EXAMPLE 2

Synthesis of 810E: 8 Arm 10,000 Molecular Weight (αGal(1,3)Gal β 1–4 GlcNAc)$_8$ PEG using EDC for Coupling In an Eppendorf tube, 100 mg of 8 arm, 10,000 molecular weight PEG-(NH$_2$)$_8$ (Shearwater Polymers, Inc., Huntsville, Ala. 35801), 80 mg of EDC and 106 mg of αGal(1,3)Gal β 1–4 GlcNAc were dissolved in 1 mL of DI water. The reaction proceeded for one hour after which an additional 80 mg of EDC was added. The reaction proceeded for an additional 3 hours. The reaction mixture was filled into a dialysis tube of molecular weight cut-off 3,500 and dialyzed five times against 4 liters of DI water. The dialyzed material was freeze-dried to a white powder. Amino group analysis revealed that more than 98% of amino groups were modified.

EXAMPLE 3

Synthesis of 820E: 8 Arm 20,000 Molecular Weight (αGal(1,3)Gal β 1–4 GlcNAc)$_8$ PEG using EDC for Coupling In a 250 mL plastic screw bottle, 20 grams of 8 arm 20,000 molecular weight PEG-(NH$_2$)$_8$ (Shearwater Polymers, Inc., Huntsville, Ala. 35801) and 10.6 grams of αGal(1,3)Gal β 1–4 GlcNAc were dissolved in 100 mL of DI water by rotating the bottle head over head. To this solution, 8 g of EDC were added and the reaction proceeded for 1.5 hours under rotation after which an additional 8 g of EDC was added. The reaction proceeded for an additional 3.5 hours. The reaction mixture was filled into dialysis tubes of molecular weight cut-off of 3,500 and dialyzed four times against 20 liters of DI water. The dialyzed material was freeze-dried to a white powder. Amino group analysis revealed that more than 98% of amino groups were modified.

EXAMPLE 4

Synthesis of 410N: 4 Arm 10,000 Molecular Weight (αGal(1,3)Gal β 1–4 GlcNAc)$_4$-PEG using EDC and N-Hydroxysuccinimide (NHS) Coupling In a 15 mL centrifuge tube, 50 mg of 4 arm 10,000 molecular weight PEG-(NH$_2$)$_4$, 500 mg of EDC, 26.5 mg NHS (Pierce, Rockford, Ill. 61105) and 39.5 mg of αGal(1,3)Gal β 1–4 GlcNAc were dissolved in 3.125 mL of 0.1 M MES buffer, pH 5.5. The reaction mixture was rotated head over head for 4.5 hours. The reaction mixture was filled into a dialysis tube of molecular weight cut off 3,500 and dialyzed five times against 4 liters of DI water. The dialyzed material was freeze-dried to a white powder. Amino group analysis revealed that more than 98% of amino groups were modified.

EXAMPLE 5

Synthesis of 410 S: 4 Arm 10,000 Molecular Weight (αGal(1,3)Gal β 1–4 GlcNAc)$_4$-PEG using EDC and N-Hydroxysulfosuccinimide (NHSS) for Coupling In a 500 mL glass beaker with stopper, 12.5 g of 4 arm 10,000 molecular weight PEG-(NH$_2$)$_4$, 31.25 g of EDC, 3.5 g of NHSS (Pierce, Rockford, Ill. 61105) and 7.5 g of αGal(1,3)Gal β 1–4 GlcNAc were dissolved in 250 mL of 0.1 M MES buffer, pH 5.5. The reaction mixture was shaken on an orbital shaker overnight. The reaction mixture was filled into dialysis tubes of molecular weight cut off 3,500 and dialyzed five times against 20 liters of DI water. The dialyzed material was freeze-dried to a yellowish powder. Amino group analysis revealed that more than 98% of amino groups were modified.

EXAMPLE 6

Synthesis of 810S: 8 Arm 10,000 Molecular Weight (αGal(1,3)Gal β 1–4 GlcNAc)$_8$-PEG using EDC and NHSS for Coupling In a 500 mL glass beaker with stopper, 12.5 g of 8 arm 10,000 molecular weight PEG-(NH$_2$)$_8$, 62.5 g of EDC, 7 g of NHSS and 15 g of αGal(1,3)Gal β 1–4 GlcNAc were dissolved in 250 mL of 0.1 M MES buffer, pH 5.5. The reaction mixture was shaken on an orbital shaker overnight. The reaction mixture was filled into dialysis tubes of molecular weight cut off 3,500 and dialyzed five times against 20 liters of DI water. The dialyzed material was freeze-dried to a yellowish powder. Amino group analysis revealed that more than 98% of amino groups were modified.

EXAMPLE 7

Synthesis of 820S: 8 Arm 20,000 Molecular Weight (αGal(1,3)Gal β 31–4 GlcNAc)$_8$-PEG using EDC and NHSS for Coupling In a 500 mL glass beaker with stopper, 12.5 g of 8 arm 20,000 molecular weight PEG-(NH$_2$)$_8$, 31.25 g of EDC, 3.5 g of NHSS and 7.5 g of αGal(1,3αGal β 1–4 GlcNAc were dissolved in 250 mL of 0.1 M MES buffer, pH 5.5. The reaction mixture was shaken on an orbital shaker overnight. The reaction mixture was filled into dialysis tubes of molecular weight cut off 3,500 and dialyzed five times against 20 liters of DI water. The dialyzed material was freeze-dried to a yellowish powder. Amino group analysis revealed that more than 98% of amino groups were modified.

EXAMPLE 8

Synthesis of 410LS: 4 Arm 10,000 Molecular Weight Eight Lys-coupled Amino Groups (αGal(1,3)Gal β 1–4 GlcNAc)$_8$-PEG using EDC and NHSS for Coupling PEG-(NH$_2$)$_8$ was synthesized by covalently linking a lysine residue to each of the amine ends of the 4-arm 10,000 mw PEG. Since a lysine contains 2 amino groups and a carboxy group, the carboxy group was coupled to the amine group of the PEG, thereby doubling the number of amine groups on the PEG.

In a 15 mL centrifuge tube, 50 mg of 4 arm 10,000 molecular weight PEG-(NH$_2$)$_8$, 1000 mg of EDC, 100 mg NHS and 79 mg of αGal(1,3)Gal β 1–4 GlcNAc were dissolved in 3.125 mL of 0.1 M MES buffer, pH 5.5. The reaction mixture was rotated head over head for 4.5 hours. The reaction mixture was filled into a dialysis tube of molecular weight cut off 3,500 and dialyzed five times against 4 liters of DI water. The dialyzed material was freeze-dried to a yellowish powder. Amino group analysis revealed that more than 98% of the amino groups were modified.

EXAMPLE 9

Synthesis of 410L: 4 Arm 10,000 Molecular Weight, Eight Amino Groups (αGal(1,3)Gal β 1–4 GlcNAc)$_8$-PEG using EDC for Coupling In a 15 mL plastic centrifuge tube, 50 mg of 4 arm 10,000 molecular weight PEG-(NH$_2$)$_8$, 230 mg of EDC and 105 mg of αGal(1,3)Gal β 1–4 GlcNAc were dissolved in 3 mL of DI water. The reaction proceeded for one hour after which an additional 230 mg of EDC was added. The reaction proceeded for an additional 3 hours. The reaction mixture was filled into a dialysis tube of molecular weight cut-off of 3,500 and was dialyzed five times against 4 liters of DI water. The dialyzed material was freeze-dried to a white powder. Amino group analysis revealed that more than 98% of the amino groups were modified.

EXAMPLE 10

Synthesis of 410SS: 4 Arm 10,000 Molecular Weight, Four Amino Groups (αGal(1,3)Gal β 1–4 GlcNAc)$_4$-sulfo-PEG using EDC and NHSS for Coupling In a 15 mL centrifuge tube, 50 mg of 4 arm 10,000 molecular weight Sulfo-PEG-(NH$_2$)$_4$, 500 mg of EDC, 50 mg NHS and 39.5 mg of a αGal(1,3)Gal β 1–4 GlcNAc were dissolved in 3.125 mL of 0.1 M MES buffer, pH 5.5. The reaction mixture was rotated head over head for 4.5 hours. The reaction mixture was filled into a dialysis tube of molecular weight cut off 3,500 and dialyzed five times against 4 liters of DI water.

EXAMPLE 11

Synthesis of 410ES: 4 Arm 10,000 Molecular Weight, Four Amino Groups (αGal(1,3)Gal β 1–4 GlcNAc)$_4$-sulfo-PEG using EDC for Coupling In a 15 mL plastic centrifuge tube, 300 mg of 4 arm 10,000 molecular weight Sulfo-PEG-(NH$_2$)$_4$, 116 mg of EDC and 53.4 mg of αGal(1,3)Gal β 1–4 GlcNAc were dissolved in 3 mL of DI water. The reaction proceeded for one hour after which an additional 116 mg of EDC was added. The reaction proceeded for an additional 3 hours. The reaction mixture was filled into a dialysis tube of molecular weight cut-off of 3,500 and was dialyzed five times against 4 liters of DI water. The dialyzed solution was freeze-dried to a white powder. Amino group analysis revealed that more than 98% of the amino groups were modified.

EXAMPLE 12

Synthesis of 610S2: mixed 8 Arm (6 Amino Groups and Two Carboxyl Groups) 10,000 molecular weight (αGal(1,3)Gal β 1–4 GlcNAc)$_6$-(Sulfo-NHS)$_2$-PEG In a 15 mL plastic centrifuge tube, 300 mg αGal(1,3)Gal β 1–4 GlcNAc were incubated with 1000 mg of EDC, 100 mg NHSS in 6 mL of 0.1 M MES buffer, pH 5.5 for two hours. 100 mg of mixed 8 arm (6 amino groups and two carboxyl groups) 10,000 molecular weight PEG were added to the solution and the reaction proceeded for three hours, after which 1000 mg EDC was added and the reaction was rotated head over head overnight. The resulting solution was dialyzed five times against DI water and freeze-dried.

EXAMPLE 13

Chemical Analysis of Synthesized Molecules 410S was sent to an outside laboratory for elementary analysis. The sulfur analysis showed the product contained 2.53% sulfur.

810S was dissolved in three different buffers and the optical density was measured at 270 nm. At a pH of 3, the OD was 1.4, at pH 7 the OD was 1.7, and at pH 10 the OD was 4.8, indicating incorporation of sulfo-beta-alanine units. Also, gel filtration analysis using an Aquagel-OH (Polymer Labs, Amhearst, Mass.) gel filtration column, showed all products synthesized with NHSS, to possess a strong adsorption at 270 nm which was associated with the molecular weight of the modified PEG. This excluded the possibility that the adsorption observed stemmed from contamination of the final product from the NHSS used. Elemental analysis of 810S indicated a sulfur content of 2.34%.

EXAMPLE 14

Inhibition of Xenoreactive Antibody Activity (IC50)

Principle of the assay: A competition ELISA was set up in such a way that Gal-molecules linked to human serum albumin and immobilized onto a microtiter plate and Gal-molecules linked to PEG compete for anti-Gal antibodies in baboon serum. The antibodies binding to the Gal-HSA were visualized using secondary antibodies to these antibodies with appropriate color development agents. The color in the case in which no Gal-PEG was added was defined as 100%. The IC50 was defined, for FIG. 3, as the concentration of Gal-PEG needed to inhibit 50% of the color development when trying to detect antibodies immobilized onto the Gal-HSA plate. For FIG. 24, the IC50 is defined in terms of mass per volume, e.g. mg/mL, of polymer.

Briefly, a 96 well microtiter was coated with 100 ul/well of a 30 ug/mL solution of αGal(1,3)Gal β 1–4 GlcNAc-human serum albumin (Gal-HSA) and incubated for 90 minutes at room temperature. After incubation with Gal-HSA, the plate was blocked with 1% HSA in PBS for 60 minutes.

While the microtiter plate was coated and blocked, samples were prepared as follows: Fifteen different dilution solutions were prepared for 1 plate. The first dilution solution was 1% HSA in PBS. Dilution solutions 3–5 were obtained by preparing a 2.5 mL stock solution of 10 mM αGal(1,3)Gal β 1–4 GlcNAc in 1% HSA/PBS and then serially diluting 1/10 three times. Dilution solutions 6–15 were obtained by preparing a 2.5 mL stock solution of the first concentration of modified PEG and then serially diluting 1/10 nine times in 1% HSA in PBS.

The plate was incubated for 90 minutes at 4° C. The plate was washed five times with PBS containing 0.5% Tween 20 and blot dried.

When assaying for xenoreactive IgM, 100 ul/well of Goat anti-human IgM-biotin antibody, diluted 1/4000 in 1% HSA/PBS, was added.

When assaying for xenoreactive IgG, 100 ul/well of Goat anti-human IgG-biotin antibody, diluted 1/4000 in 1% HSA/PBS, was added.

The biotinylated secondary antibody was incubated for one hour at 4° C. and afterwards the plate was washed five times with PBS containing 0.5% Tween 20 and blot dried. Hereafter, 100 ul/well streptavidin-alkaline phosphatase conjugate was added at a dilution of 1/4000 in 1% HSA/PBS and incubated for 30 minutes at room temperature. The microtiter plate was washed five times with PBS containing 0.5% Tween 20 and blot dried. 150 ul developer per well was added and the plate incubated for 30 minutes at room temperature. The color development was stopped by addition of 40 ul/well of 3 M NaOH. The plate was read in a plate reader at wavelength of 405 nm.

The IC50 data was calculated from the percent inhibition from the dilution of baboon control in 1% HSA/PBS which gave this highest point within the linear range.

% Inhibition=(([OD of BC in HSA]–[OD of BC in αGal(1,3)Gal β 1–4 GlcNAc or PEG-(αGal(1,3)Gal β 1–4 GlcNAc)$_x$])/OD of BC in HSA)*100

Results: As shown in FIG. 24, the molecules made using NHSS achieved 50% inhibition of xenoreactive antibody activity at much lower concentrations than those made using EDC alone. FIG. 24 also provides IC50 values for a variety of different polymeric formulations. In terms of experimental protocol, the only significant difference between the experiements producing the data of FIGS. 3 and 24 was to use a new pipette tip for additions of αGal preparations to the wells of the ELISA plate, which should prevent any inadvertant contamination with higher concentrations of the αGal sample. Furthermore, the values reported in FIG. 24 are in mass per volume, rather than molar. According to FIG. 24, the 810S preparation had an IC50 of $5\times10^{-6}$ mg/mL, compared to the 810E preparation with an IC50 of 0.1 mg/mL. For instance, the 810S molecule achieved 50% inhibition at $1\times10^{-5}$ M, compared to the 801E molecule which required $1\times10^{-1}$ M for the same effect.

EXAMPLE 15

Enzyme-linked Immunospot (ELISPOT) Assays

To each well of the first 10 columns of a sterile hydrazine modified polystyrene 96-well plate (Coming Costar, Cambridge, Mass.), 100 μL per well of a solution containing 3.2 mg/mL αGal(1,3)Gal β 1–4 GlcNAc, 3.1 mg/mL EDC and 2.4 mg/mL NHS were added in a darkened cold room and the reaction proceeded for four hours. After careful washing with sterile $H_2O$, the plates were completely covered with plastic strips and stored at 4° C. until use. Plates were blocked with sterile 400 ul/well of PBS/1% HSA for 2 hours at 37° C. Peripheral blood mononuclear cells were isolated by Ficoll-Hypaque (specific gravity, 1.077 g/mL; Pharmacia Fine Chemicals, Piscatawy, N.J.) density gradients at 400 g for 30 min. at 22° C. Low density mononuclear cells at the interfaces were harvested, washed twice by centrifugation (400 g for 10 min.) and resuspended in serum-free complete culture medium consisting of RPMI 1640 (GIBCO, Grand Island, N.Y.) supplemented with 1% HSA, 2 mM L-glutamine, and 100 U/mL penicillin/100 ug/mL streptomycin (GIBCO, Grand Island, N.Y.). Manual hemacytometer cell counts and viability determinations were performed using trypan blue exclusion dye. Thereafter, serial dilutions of PBMNCs (starting at $5\times10^5$ cells) in 100 ul of serum-free complete culture medium were added to each well and incubated for 18–24 hours at 37° C. in 5% $CO_2$. After washing 8 times using PBS/0.1% Tween-20, the plates were incubated with biotinylated isotype specific goat anti-human Abs (biotin goat anti-human IgM Cat#62-7540; biotin goat anti-human IgG (H&L) Cat# 62-7140, Zymed, San Francisco, Calif.)(1:1000) at 37° C. for 4 hours. After washing, streptavidin conjugated alkaline phosphatase (Cat# 43-4322, Zymed, San Francisco, Calif.) (1:1000) was added for 30 min. at 37° C. Finally, after washing an additional 8 times with PBS/0.1% Tween-20, 5-Bromo-4-chloro-3indolyl-phosphate (Cat# B-8503, Sigma, St. Louis, Mo.) dissolved in 1% low-melt sea-plaque agarose (FMC Bioproducts, Cat#50101) was added as gel substrate to each well. Plates were incubated overnight in the dark at room temperature and single Ab-secreting, spot forming cells (ASC) were visualized, analyzed and counted under low magnification using an inverted phase microscope. Data represents total isotype specific anti-gal Ab-secreting cells/$10^6$PBMNCs, calculated from serially diluted cell samples.

The short-term in vitro effects of TPC on peripheral blood-derived ASCs:

short-term in vitro effects of TPC on peripheral blood-derived ASCs were assessed by incubating (2 hours at 37° C., with rotation at 6 rpm) heparinized peripheral blood from a normal donor in the presence or absence of 50 ug/mL TPC (410S). After 2 hours, mononuclear cells from both the untreated and the TPC treated blood samples were obtained and assayed for ASCs. TPC alone appeared to have no effect on total cell yield and viability or on the number of detectable ASCs (data not shown). These findings indicate that under these in vitro culture conditions, TPC is not apparently cytotoxic to any particular peripheral blood mononuclear cell population (T cells, B cells and monocytes/macrophages) and has no direct inhibitory or stimulatory effect on anti-Gal ASC.

Effect of TPC on T cell-independent anti-Gal B cell activation:

Purified CD19+ B cells were obtained by positive selection with the use of anti-CD19+ immunomagnetic beads (Pan-B (CD19); Dynal, Lake Success, N.Y.). The B cell population obtained was >95% reactive with the anti-CD20 mAb (CD20-PE, clone L27; Becton Dickinson, San Jose Calif.). Purified CD19+ B cells ($1\times10^5$/well) were cultured with formalinized Staphylococcus aureus cells (SAC, Cowan strain, Calbiochem) (1:10,000) plus IL-2 (50 ng/mL), IL-4 (50 ng/mL) (R&D Systems, Minneapolis, Minn.) and anti-CD40 (1 ug/mL, Cat#33070D; Pharmingen, San Diego, Calif.), in 96-well round bottom culture plates (Corning) in 0.2 mL of RPMI 140 medium supplemented with 10% human AB serum (anti-Gal depleted), 2 mM L-glutamine, 25 mM Hepes, and 100 U/mL penicillin/100 ug/mL streptomycin (GIBCO, Grand Island, N.Y.) at 37° C. in a humidified atmosphere with 5% $CO_2$ for 5 days. To examine the effects of TPC on xenoreactive ASC, B cells were pretreated with TPC (410S; 1 mg/mL) for 30 min. at 37° C. and then added to the cultures after extensive washing. In some experiments, 50 ug/mL of TPC (410S) was added directly to the cultures at initiation and daily thereafter. Following the 5 day culture period, cells were washed extensively, counted, viability determined and the number of ASC determined using the anti-Gal ELISPOT assay. In comparison to nonTPC treated cultures, TPC appeared to have no effect on total cell yield and viability or on the number of detectable ASCs (data not shown).

EXAMPLE 16

Effect of TPC on Xenoreactive Antibody Levels in Cynomolgous Monkeys

TPC molecule 410S was prepared as described in Example 5. 410S or PEG control was administered to cynomolgous monkeys in doses of either 50 mg or 250 mg every 3 days for 2 weeks. Blood was drawn for serum before and after each administration. During the subsequent 2 week period, blood was drawn each Monday and Friday. Serum samples were analyzed for xenoreactive IgG (X IgG) and xenoreactive IgM (X IgM).

Figure 4:
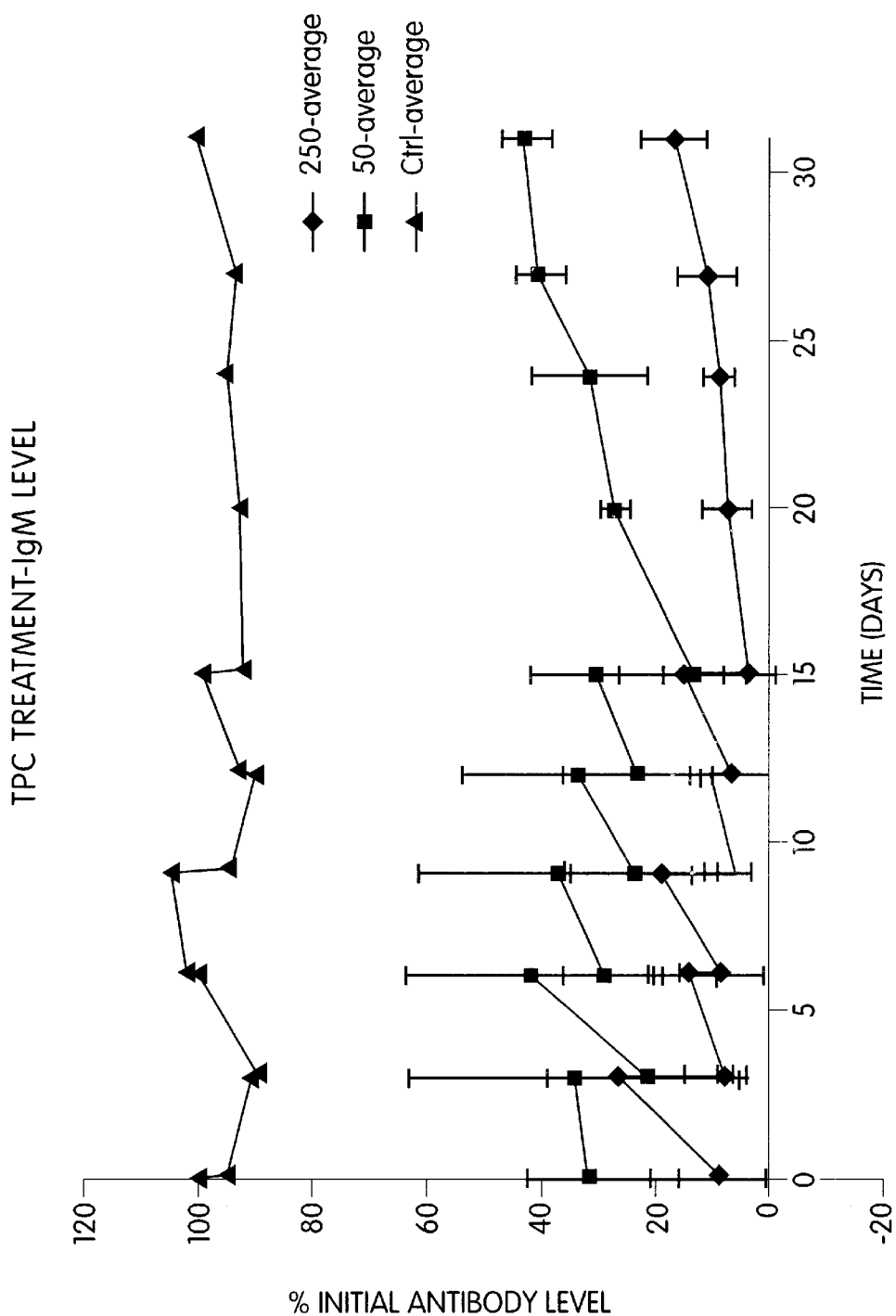
FIG. 4 shows the effect of TPC (410S) administration on anti-Gal IgM levels in cynomologous monkeys.
Figure 5:
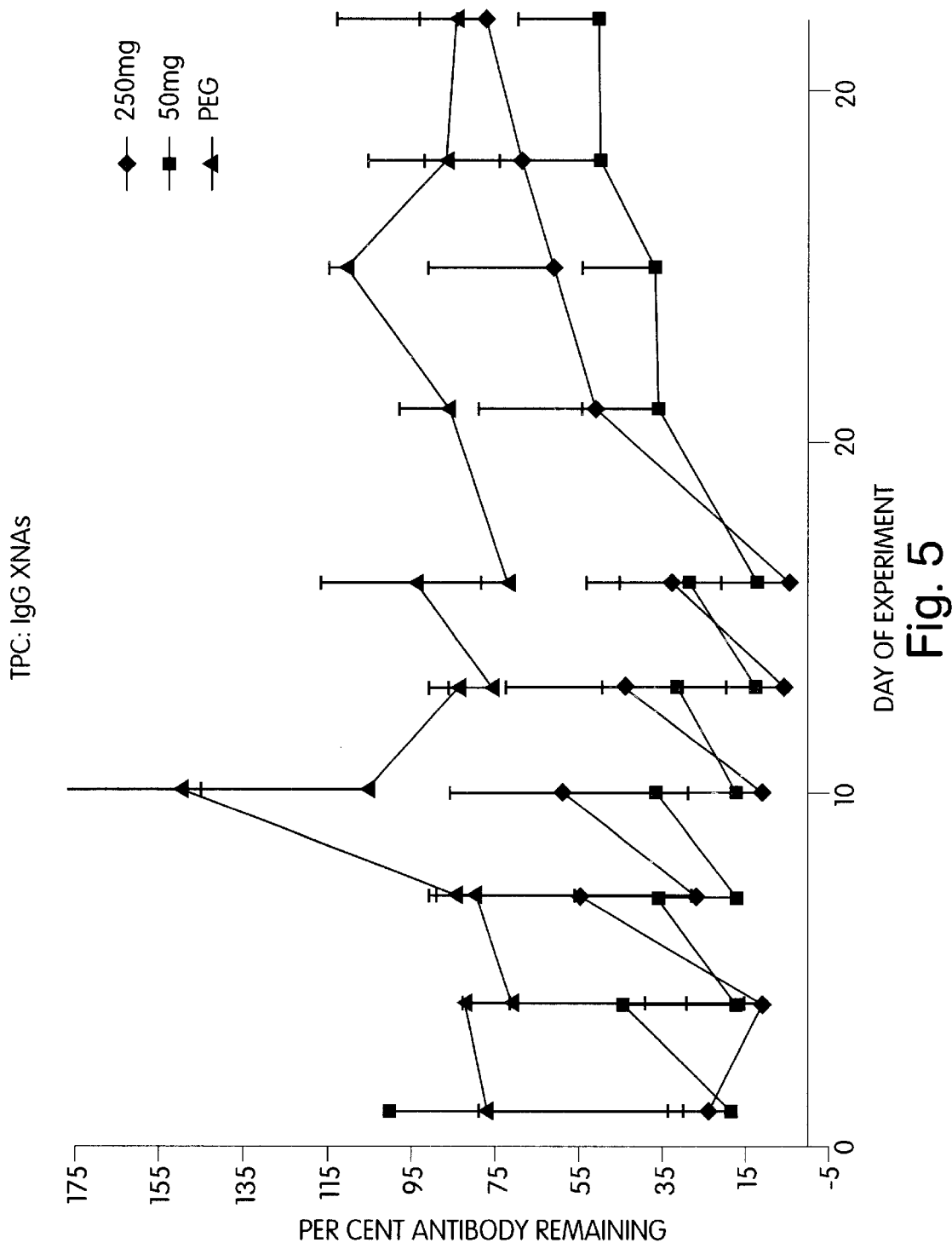
FIG. 5 shows the effect of TPC (410S) administration on anti-Gal IgG levels in cynomologous monkeys.
Figure 6:
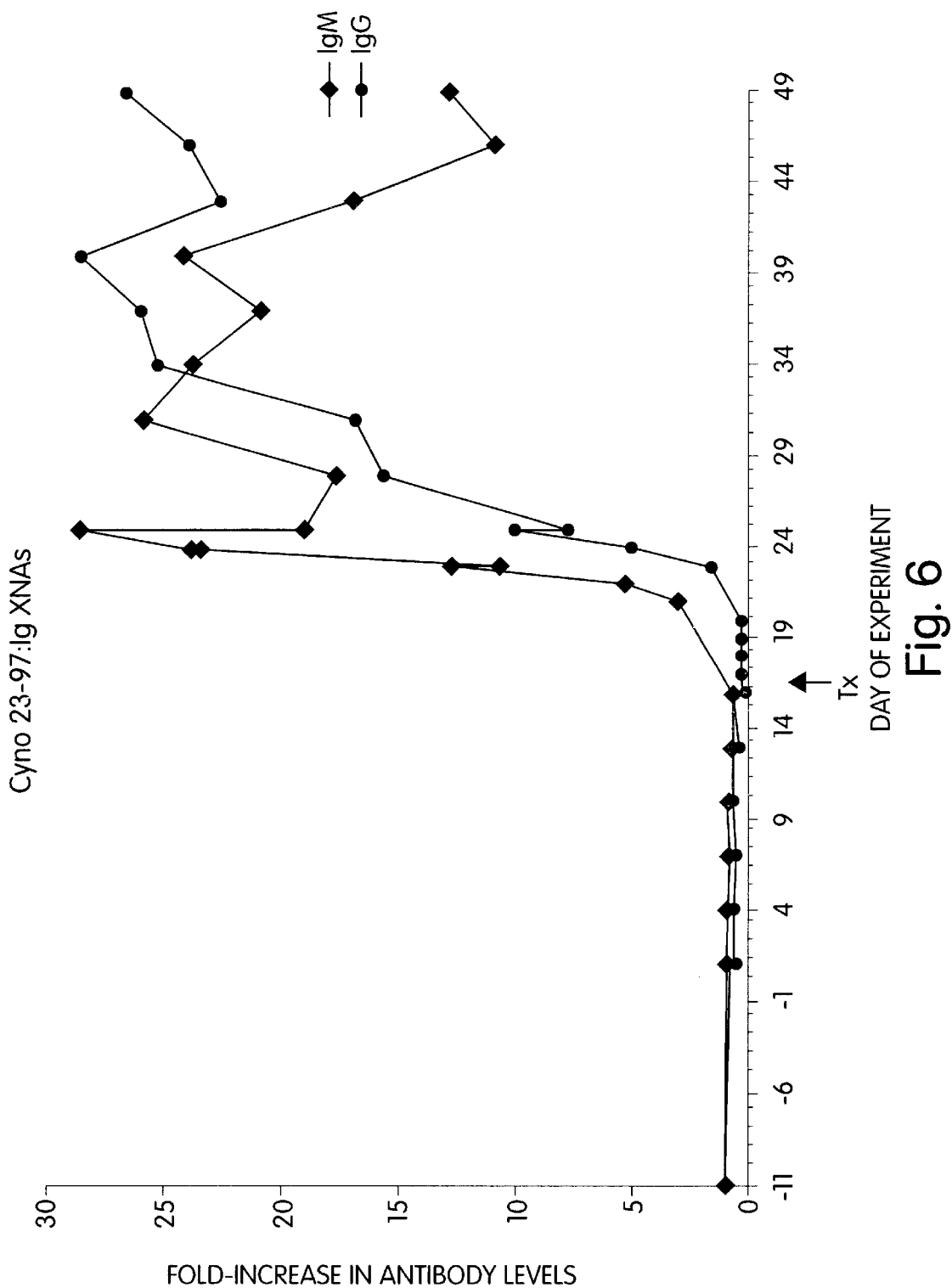
FIG. 6 shows xenoreactive antibody levels in a cynomologous monkey that received control vehicle instead of TPC (410S). "Tx" indicates day of heterotopic heart transplant.
Figure 7:
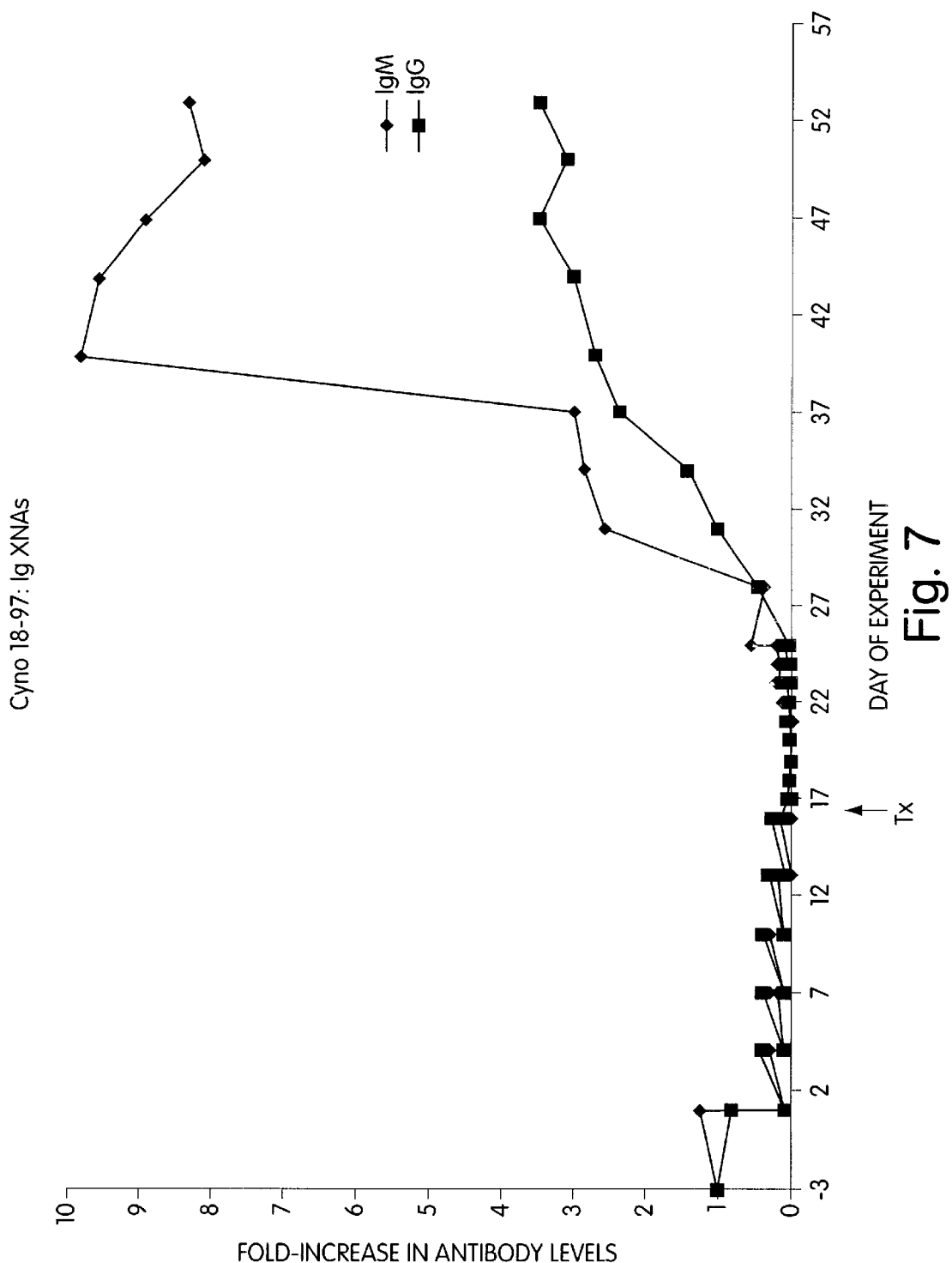
FIG. 7 shows suppression of xenoreactive antibody levels in a cynomologous monkey that received 250 mg TPC (410S) by infusion according to the schedule described in Example 17. "Tx" indicates day of heterotopic heart transplant.
Figure 8:
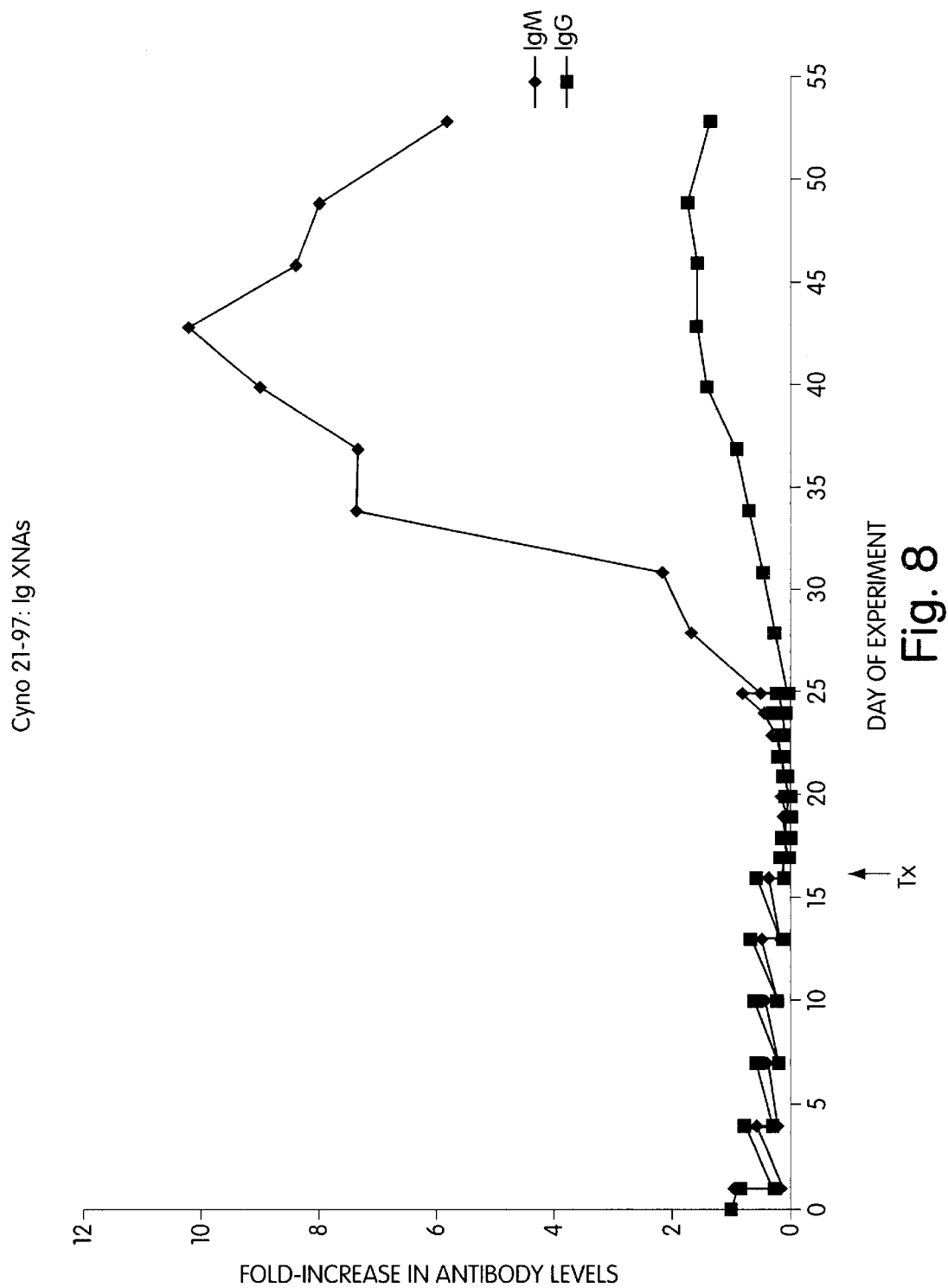
FIG. 8 likewise shows suppression of xenoreactive antibody levels in a second monkey treated as described in Example 17.
Figure 9:
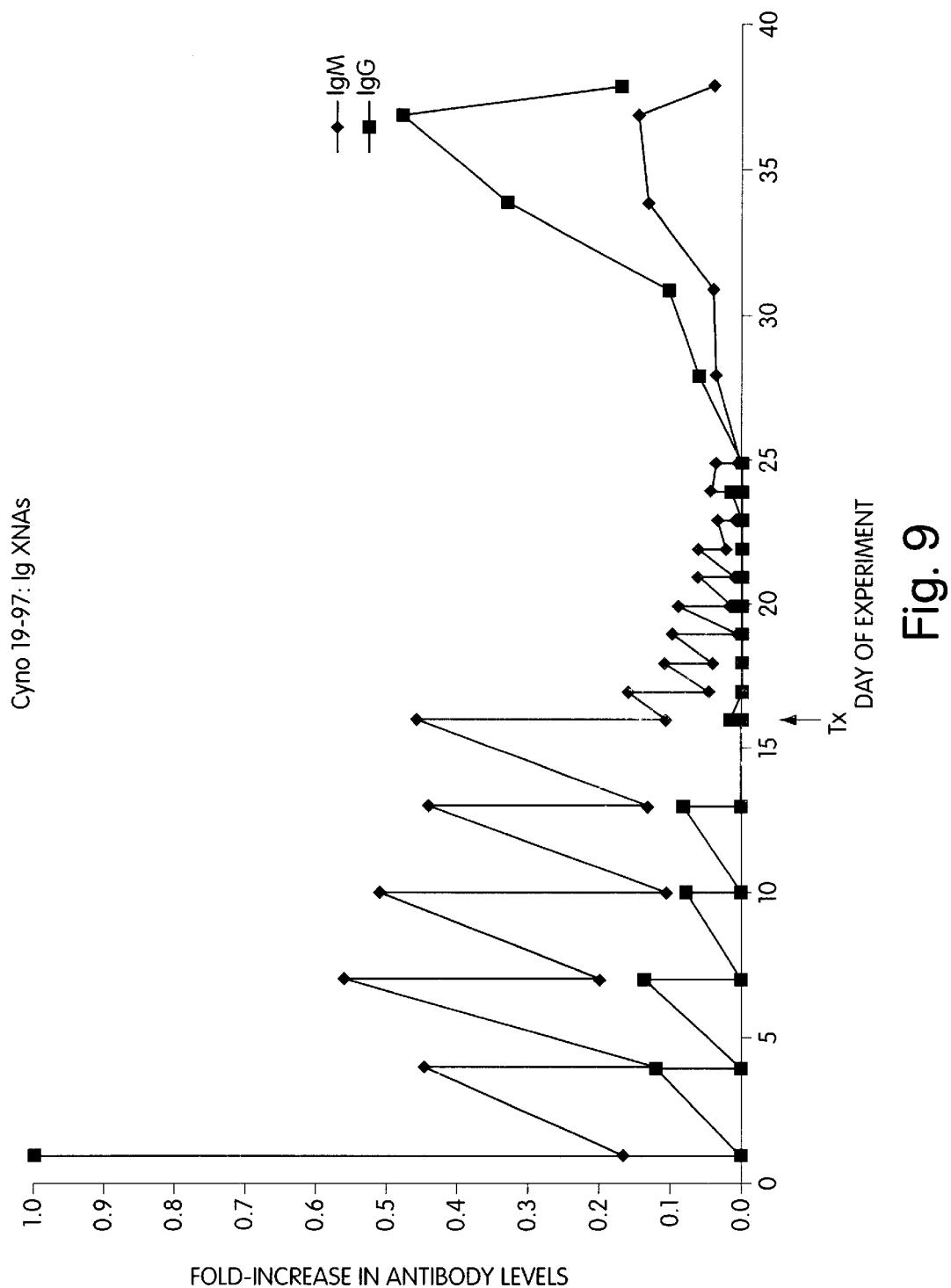
FIG. 9 likewise shows suppression of xenoreactive antibody levels in a third monkey treated as described in Example 17.

Results are shown for IgM in FIG. 4 and for IgG in FIG. 5. In the case of anti-Gal IgM levels, both the 50 mg and the 250 mg doses dramatically reduced the level compared to control animals treated with the blocked PEG. After 6 TPC treatments the IgM level in the 250 mg dose was approximately 5% of the initial level and the IgM level in the 50 mg dose was approximately 15% of the initial level. This low level of anti-Gal IgM was maintained even after dosing with TPC had stopped. Indeed, at 15 days post-treatment the level in the 250 mg animals was averaging 15% of the predosing level. In the 50 mg animals the level was aproximately 40% of the initial level. These data strongly suggest that TPC can deplete IgM levels and that this depletion has a long lasting effect. Similar data were seen with the anti-Gal IgG levels although the effct was not as dramatic and there was not as evident a dose-responsive effect. The reasons for this are not clear although it is important to recognize that the most important antibodies in terms of hyperacute rejection are those of the IgM class.

EXAMPLE 17

TPC Treatment with Discordant Xenotransplant in Cynomolgous Monkeys

The TPC molecule 410S was prepared as described above in Example 5. Three monkeys received 250 mg TPC (# 19–97, 18–97, 21–97), and two monkeys received 250 mg control vehicle (#28–97, 23–97) every 3 days for 2 weeks (total 6 doses/animal) via IV infusion. 250 mg/5mL per vial was supplied as sterile solution to be injected into 50 mL sterile physiological saline in an IV bag and administered IV at a rate of approximately 2–3 mLs/min. Prior to administration and 15–60 minutes after administration was complete, 1–3 mLs of blood was drawn for serum from each monkey at a site distant from the site of administration. On the day of the 6th dose, each monkey underwent a heterotopic heart transplant following drug infusion. A heart from a transgenic pig which expresses human CD59 and human CD55 was placed in the abdominal position as described (Byrne, et al., 1997, *Transplantation* 63:149–155) and remained in place up to 6 hours before being explanted.

Following the transplant and explant, the monkeys continued infusion of either TPC or control vehicle, as above, once per day for 9 days. Blood was drawn for serum analysis before and after each administration. The monkeys were monitored for at least 15 days after cessation of TPC administration, and blood was drawn 2 times per week for serum analysis. One monkey died 2 days post-transplant.

Results are shown in FIGS. 6 to 9.

The control animal (Cyno 23–97, see FIG. 6) experienced a 28-fold increase in IgG XNA levels, and a 25-fold increase in IgM XNA levels post-transplant. Most likely, this was due to stimulation by the pig heart tissue of B cells which produce IgM anti-Gal antibodies to differentiate into IGM-XNA producing plasma cells, and due to stimulation of B cells which produce IgM anti-Gal antibodies to class switch to become IgG XNA-producing B cells and then to differentiate into IgG XNA-producing plasma cells. In contrast, the monkeys which received TPC maintained low levels of xenoreactive antibodies during the 9 days of TPC administration following explant of the pig heart. Following cessation of TPC, XNA levels rose, but not as dramatically as in the non-TPC-treated control.

EXAMPLE 18

In vivo Effects of TPC Administration on Circulating Anti-Gal ASC

Figure 10:
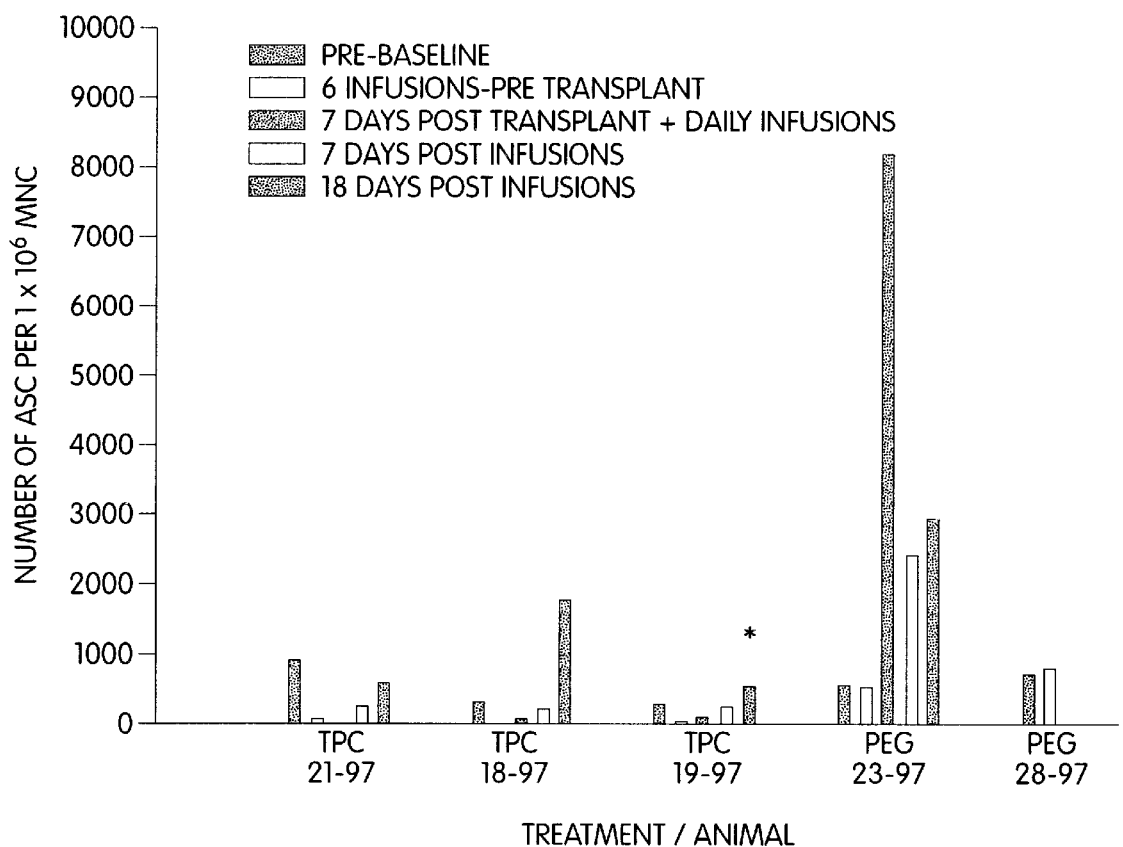
FIG. 10 shows the inhibition of anti-Gal IgM secreting B cells achieved with an exemplary composition of the invention. TPC=410S
Figure 11:
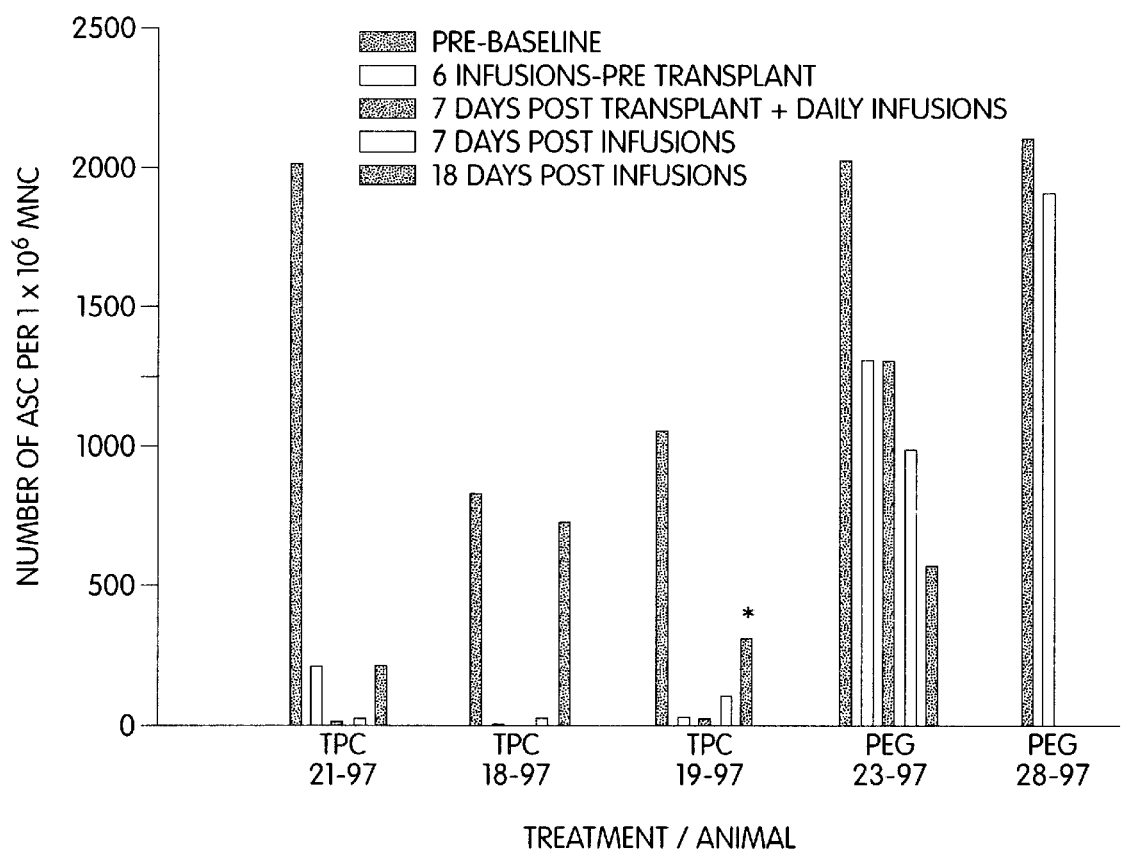
FIG. 11 shows the inhibition of anti-Gal IgG secreting B cells by TPC (410S).

To investigate the in vivo response of circulating anti-Gal ASC to TPC administration, we measured the number of ASC per $10^6$ peripheral blood mononuclear cells isolated from cynomologous monkeys treated with either TPC (410S) or blocked-PEG as control. Blocked PEG is a 4-arm, 10,000 MW PEG-amine that was reacted with acetic anhydride in order to block the amine-groups of the PEG. Briefly, heparinized peripheral blood samples (2–3 mL) from TPC and PEG treated monkeys were obtained prior to experimentation, after 6 dosages of TPC, 7 days following porcine heart transplantation with daily infusions, 7 days post infusion termination, and 18 days post infusion. Results are shown in FIGS. 10–11. Mononuclear cells were isolated via Ficoll-Hypaque gradient centrifugation and assayed for anti-Gal IgM and IgG ASC using the ELISPOT assay as described in Example 15. Circulating anti-Gal ASC (IgM and IgG) numbers were inhibited 70–99% following 6 dosages of TPC over 18 days; whereas PEG treatment resulted in a modest (9–35%) decrease in IgM ASC with no significant changes in the number of IgG ASC (FIGS. 2&3). At day 7 post transplantation (porcine transgenic heart), circulating IgM and IgG ASC levels decreased 98.5–100% and 70–99.7%, respectively in monkeys treated daily with TPC. In contrast, the number of IgG ASC in the PEG treated animal increased 14.9-fold with no detectable change in the number of IgM ASC. Seven days after the termination of TPC treatment, 14 days post transplantation, circulating IgG and IgM ASC were 27–84% and 1.3–9.8% of baseline values, respectively. In the PEG treated monkey, IgG ASC were 4.4 above baseline and IgM ASC levels reduced 51%. IgG ASC values from TPC treated monkeys returned to near normal baseline values at 18 days post TPC termination, however, while the number of IgG ASC in the PEG treated monkey remained elevated (5.3-fold over baseline). Taken together, these findings suggest that TPC is highly effective in depleting anti-Gal ASC from the circulation during and for several weeks post treatment.

EXAMPLE 19

Effect of TPC on Xenoreactive Antibody Level in Baboons

The TPC molecule 410S was synthesized as described in Example 5 above. Baboons were first immunoaphoresed using α-Gal-columns in order to remove circulating αGal antibodies, and to set a basis for comparison of the ability of TPC to remove αGal antibodies from the circulation.

Baboon subjects were housed and cared for under the federal guidelines for research institutions where experiments involving animals are conducted. These guidelines are published as National Institutes of Health (NIH) Publication #86-23 entitled *The Guide for Care and Use of Laboratory Animals*.

The procedures for treating and transplanting the baboons are described in Shu S. Lin et al., *Transplant Immunol.* 5:212–218, 1997. Descriptions of methods for making α-Gal-columns are contained in U.S. Pat. Nos. 5,695,759 and 5,651,968, which are herein incorporated by reference. Briefly, each baboon subject was prepared for plasma treatment by induction of anesthesia with ketamine HCl and pentamine, and anesthesia was then maintained during all procedures under inhalation and Forane™ gas. The subject's bloodstream was asceptically connected by intravenous puncture to a plasmapheresis machine which separated the plasma from the cells and platelets. The plasma was asceptically conducted to an α-Gal column; effluent from the column was pumped and remixed on-line with the cells and platelets, and reinfused to the subject. This procedure was carried out continuously for 2–3 plasma volumes. The blood flow rate of 75–100 cc/min (with a plasma flow rate of 35–50 cc/min), was well tolerated by the subject. The entire column procedure lasted 1–1.5 hours.

Figure 12:
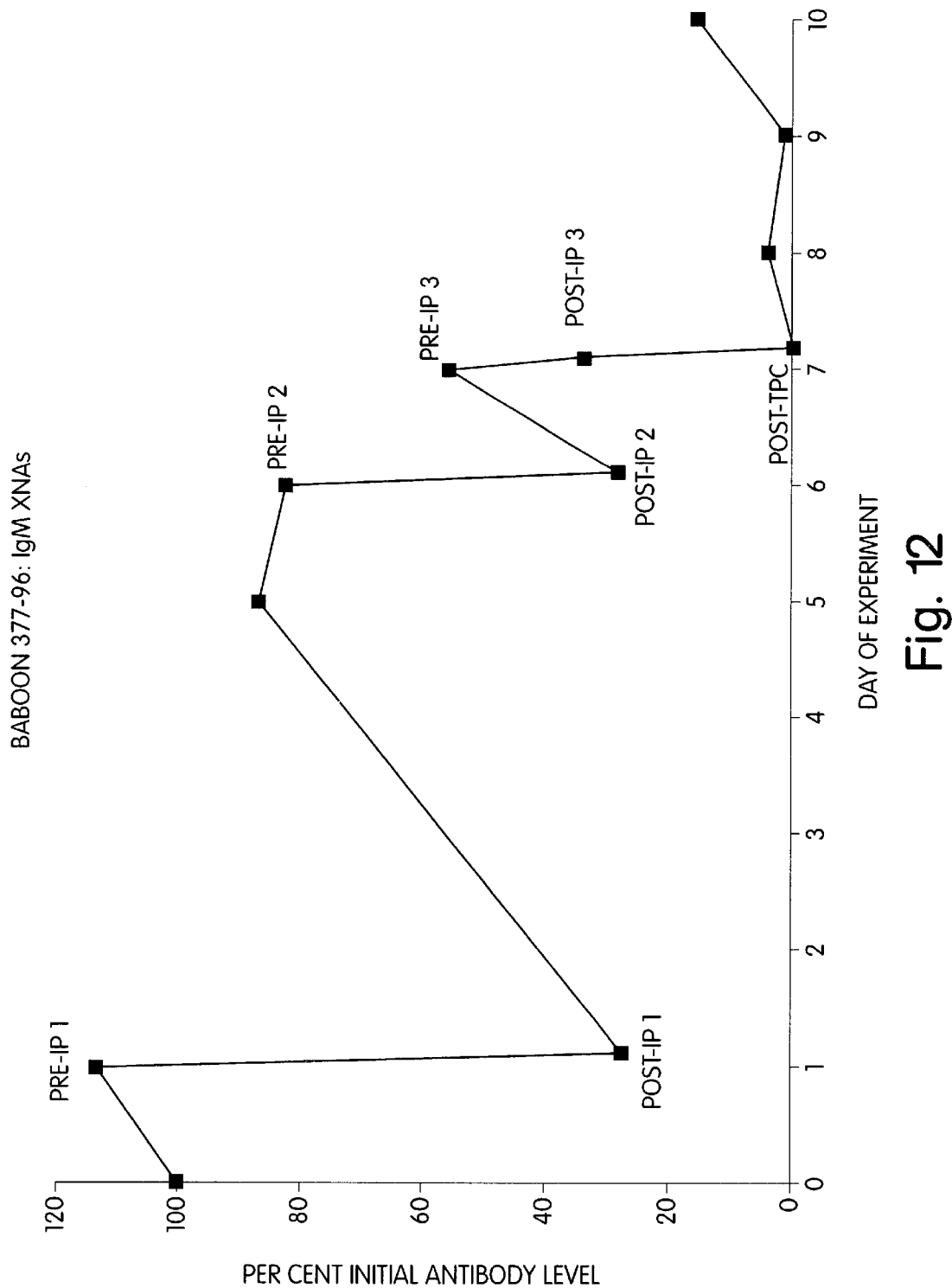
FIG. 12 shows suppression of xenoreactive IgM levels in a baboon treated with TPC (410S) as described in Example 19.
Figure 13:
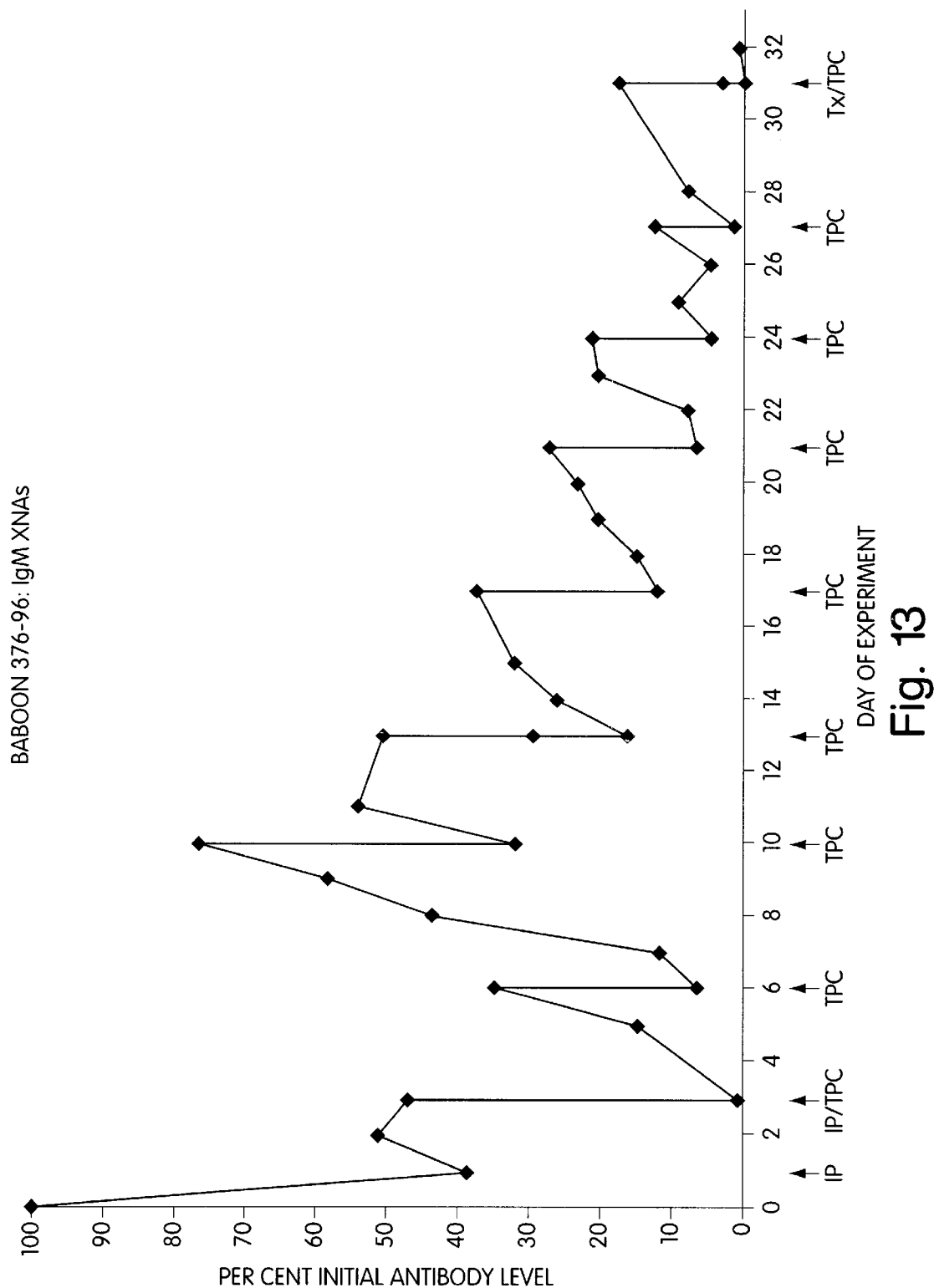
FIG. 13 likewise shows suppression of xenoreactive IgM levels in a second baboon treated with TPC (410S) as described in Example 19.

250 mg of TPC (410 S, as described in Example 5 above) was administered as noted in FIGS. 12 and 13.

Figure 14:
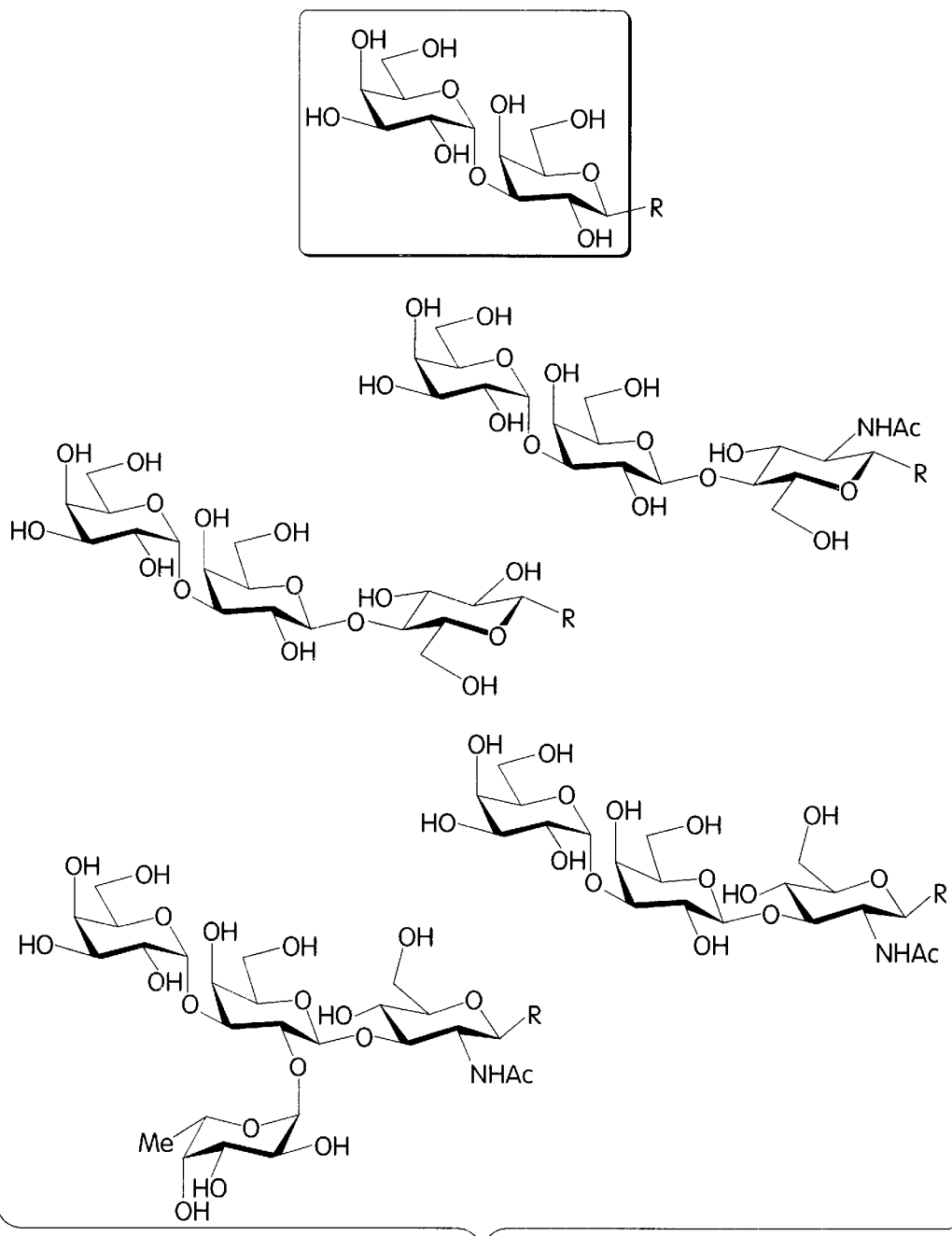
FIGS. 14–23 depict selected oligosaccharide moieties.

Results:

Baboon 377-96 (FIG. 14)

Immunoapheresis #1 removed 75% of IgM αGal antibodies from the circulation. Five days later, IgM XNAs rebounded to about 80% of pretreatment levels. A second immunoapheresis procedure brought circulating IgM XNAs to 25% of pretreatment levels. One day later, XNAs rebounded to about 55% of original levels. A third immunoapheresis brought XNA levels to 30%.baseline values, and a subsequent infusion of 250 mg TPC post-immunoapheresis resulted in undetectable levels of IgM XNAs. Three days later IgM XNA levels had rebounded to about 15% pretreatment levels. The animal developed an infection at the catheter site and the experiment was terminated. This data suggested that TPC was at least as efficient, and perhaps more efficient at reducing circulating IGM XNA levels compared to immunoapheresis.

Figure 15:
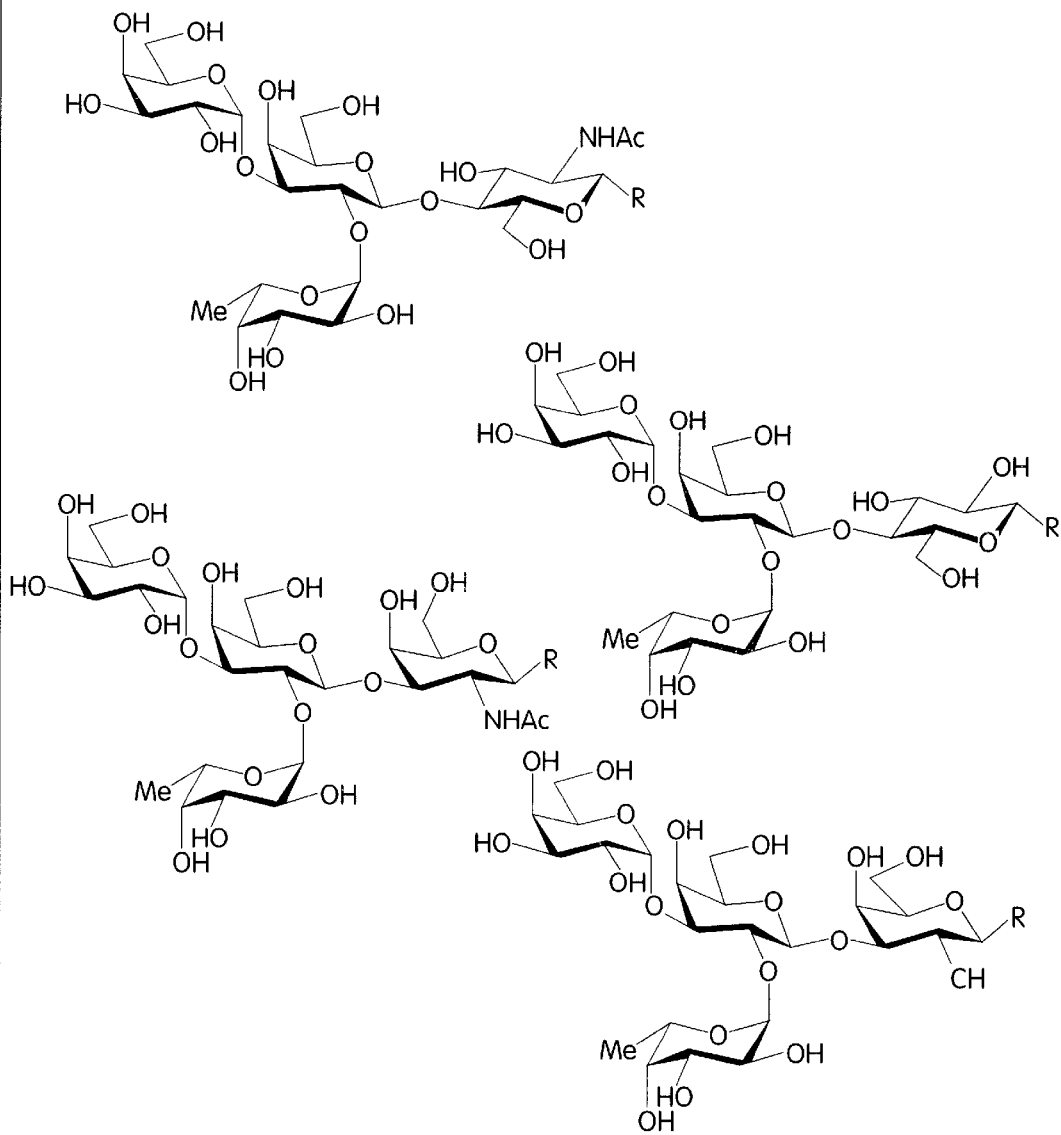
Figure 16:
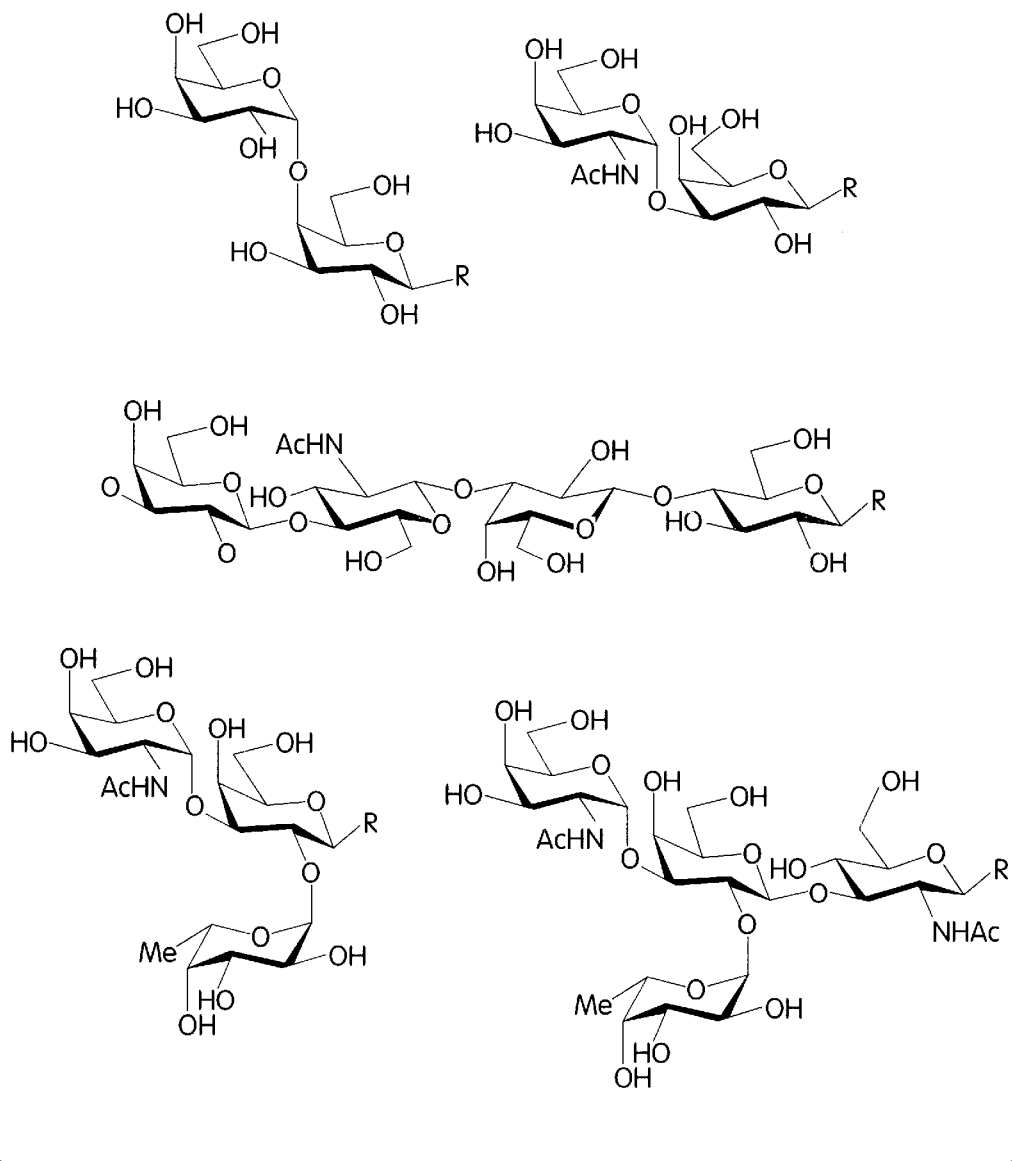
Figure 17:
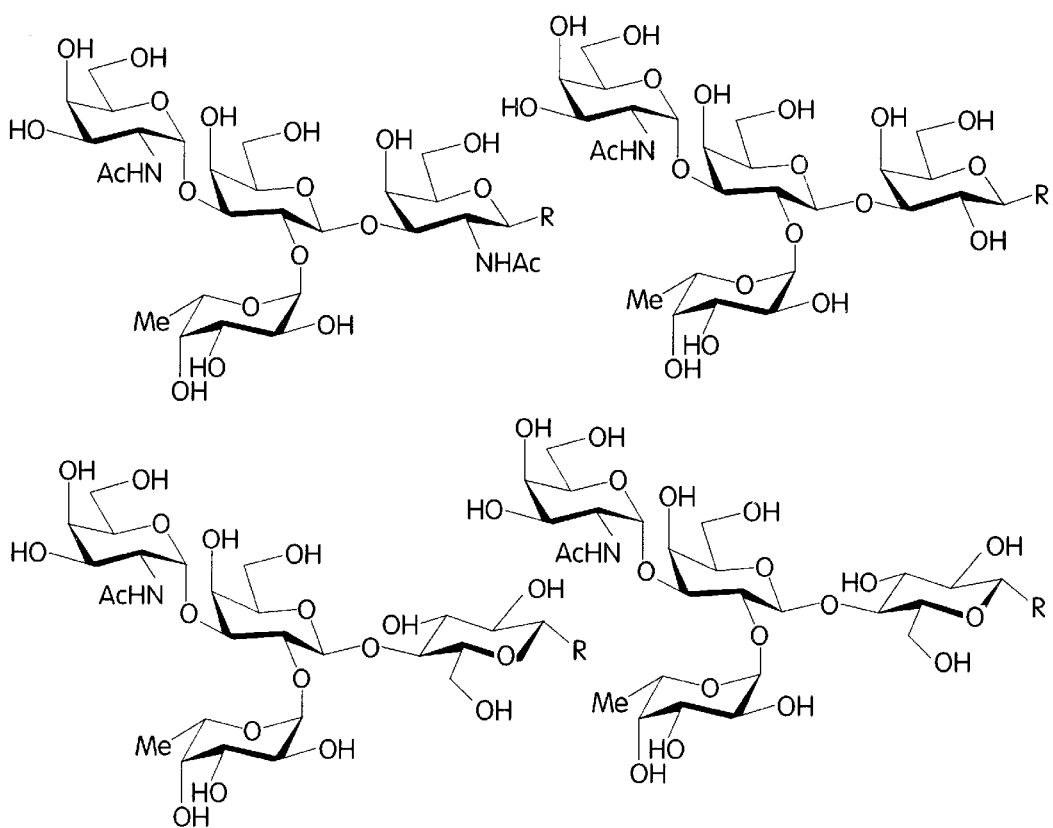
Figure 18:
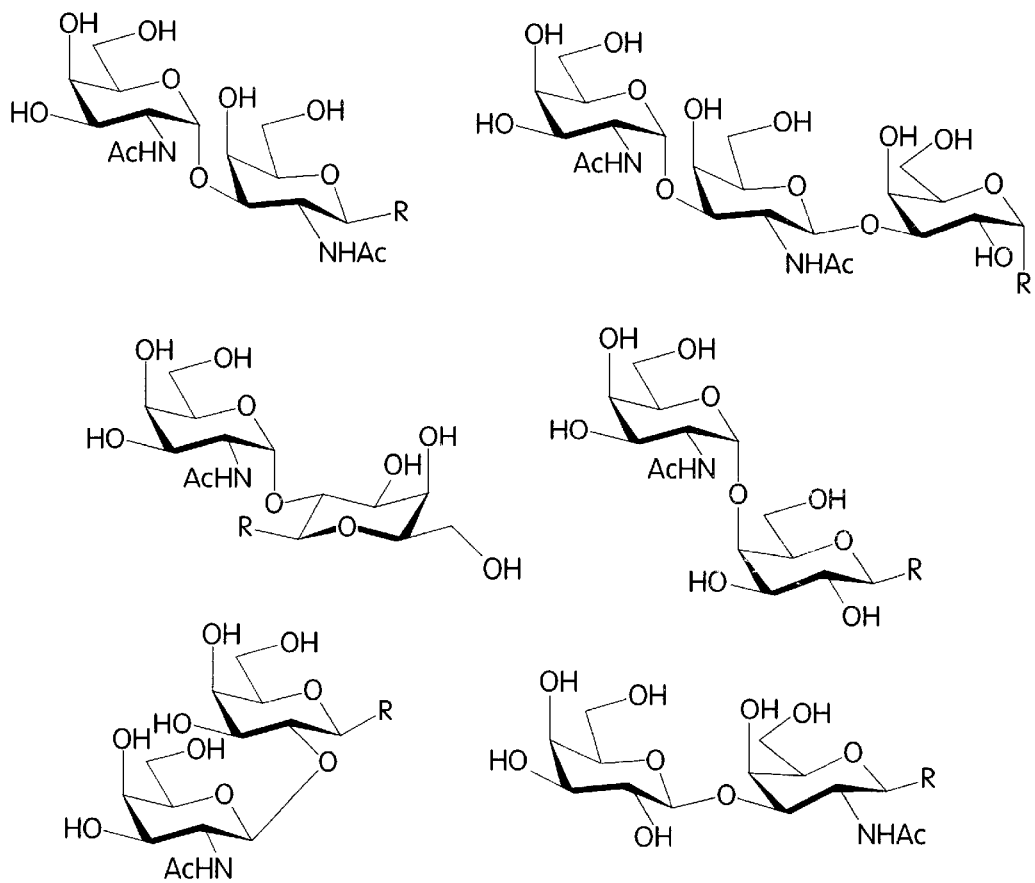
Figure 19:
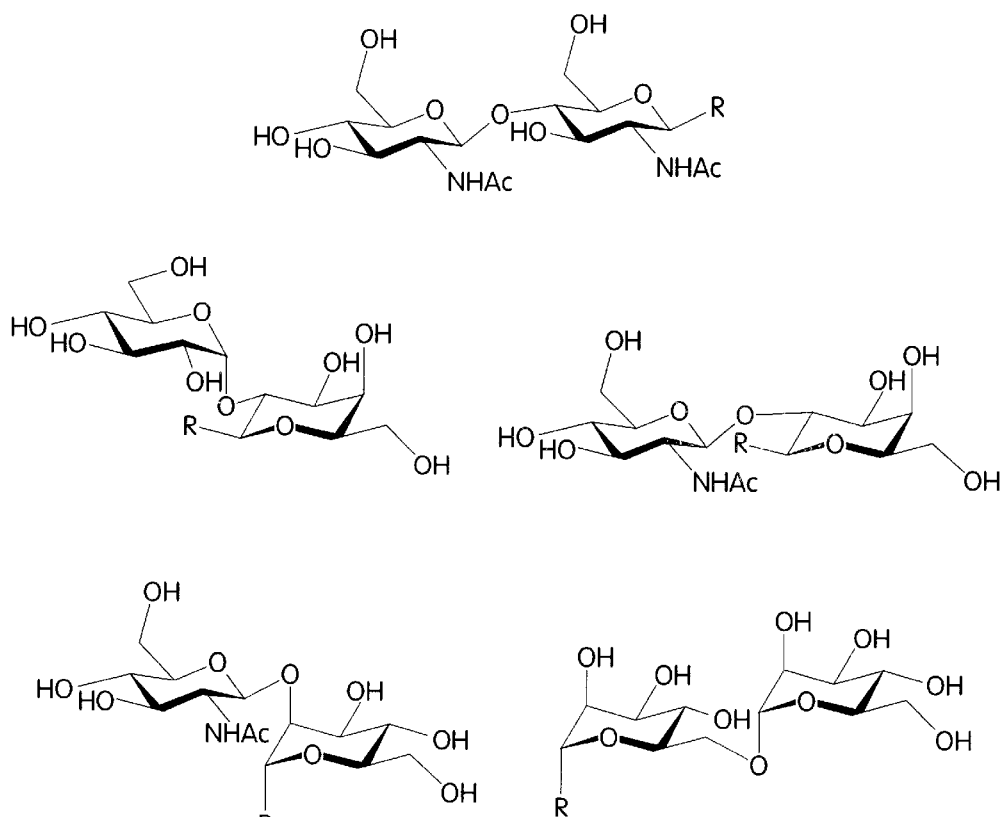
Figure 20:
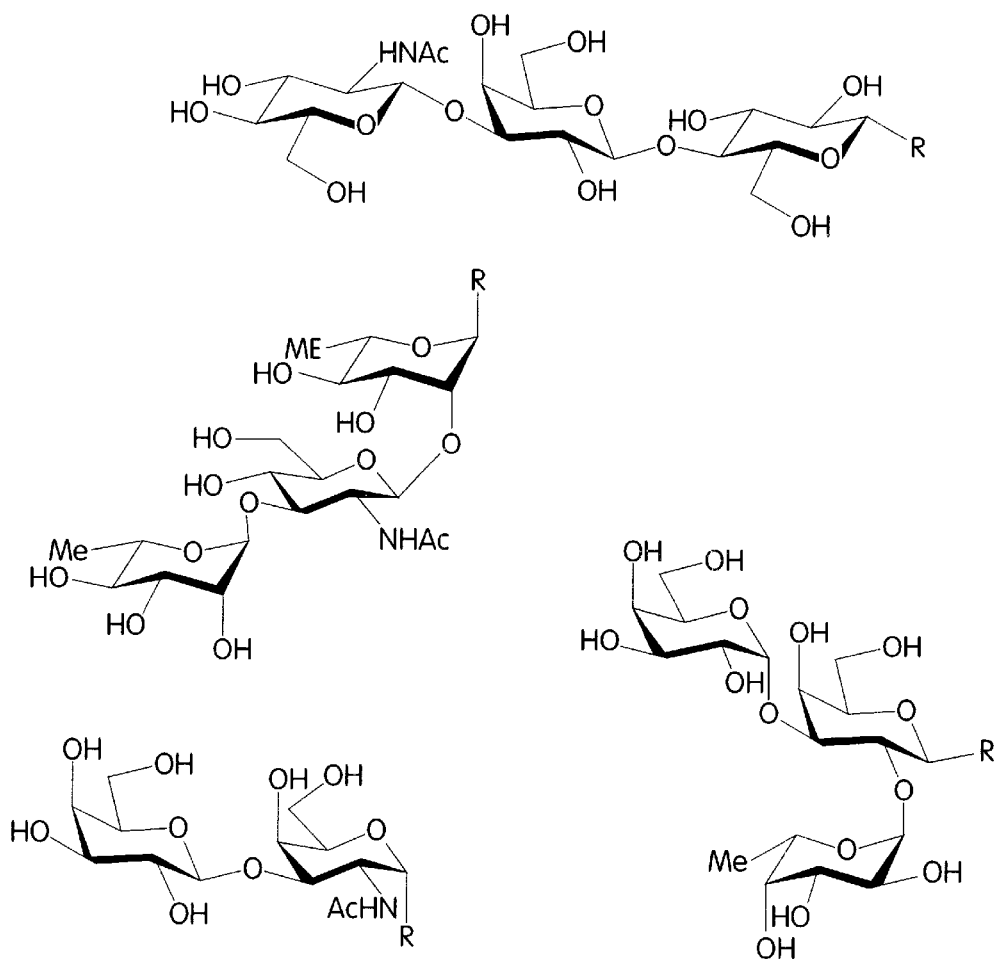
Figure 21:
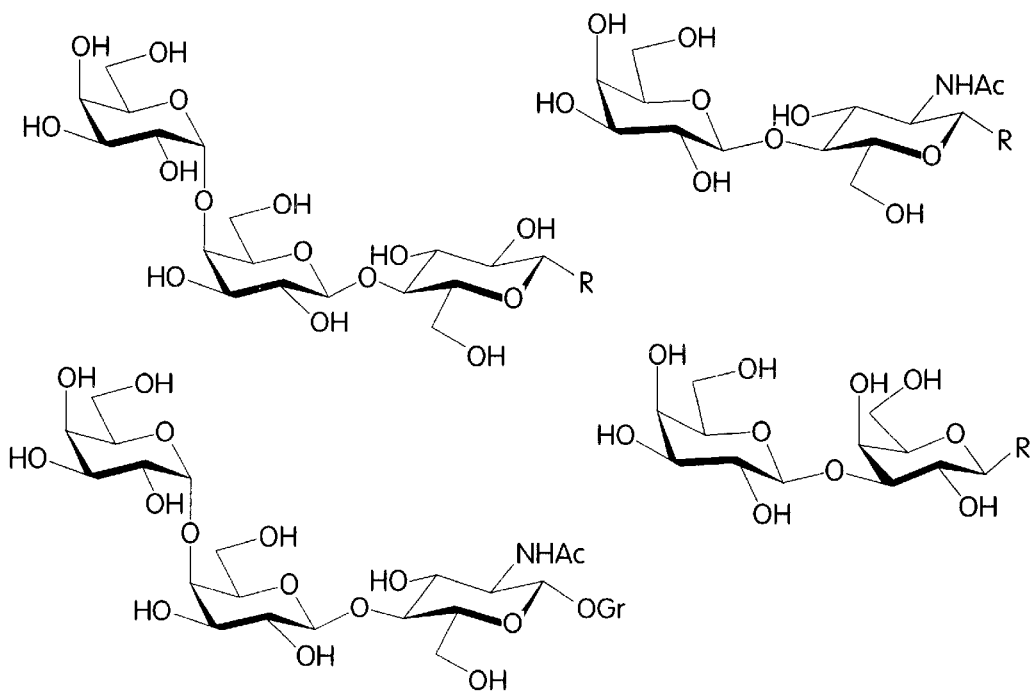
Figure 22:
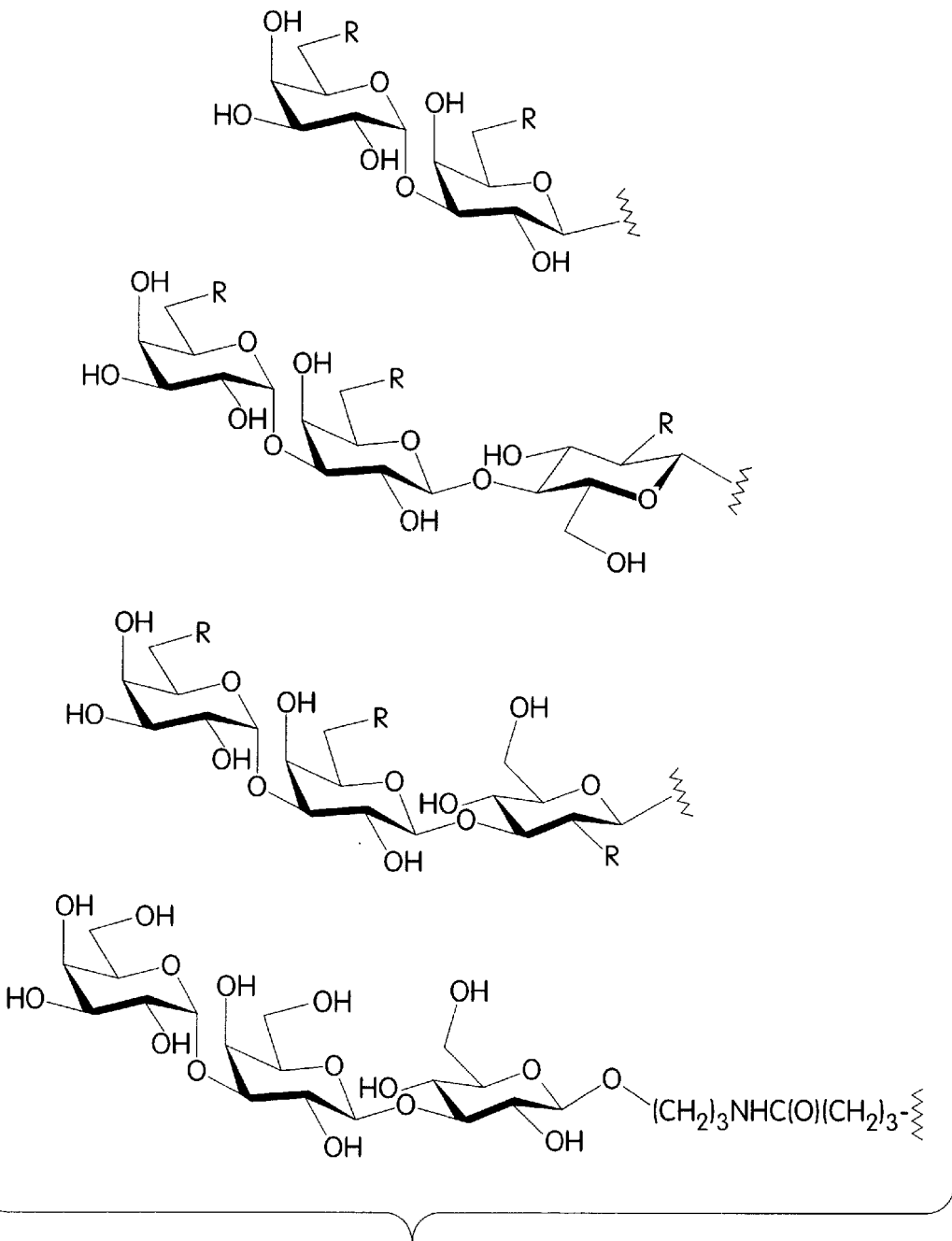
Figure 23:
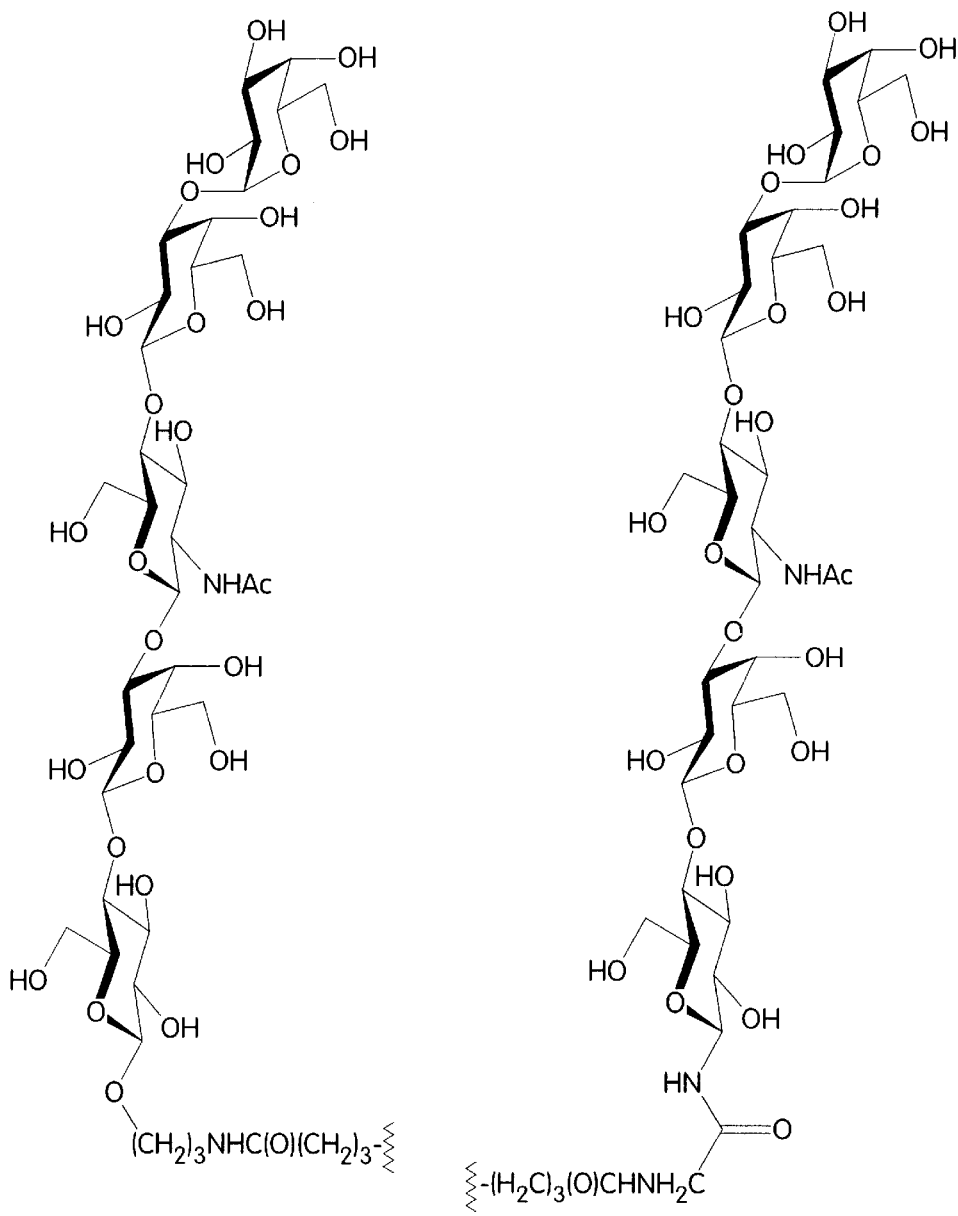

Baboon 376-96 (FIG. 15)

Immunoapheresis #1 reduced circulating IgM XNA levels to 40% of pretreatment levels. Two days later, a rebound to about 50% of pretreatment levels was observed, and after a second immunoapheresis plus administration of 250 mg TPC, circulating IgM xXNA levels were undetectable. Three days later, a rebound in IgM XNA to 35% pretreatment levels occurred, and administration of 250 mg TPC brought these levels to about 5%. Six subsequent administrations of 250 mg TPC every 3 or 4 days brought circulating levels of IgM XNA lower each time, and a less dramatic rebound effect was noted. On day 31, a kidney from a transgenic pig expressing human CD59, human CD46 and human DAF was transplanted into the baboon, and a bilateral nephrectomy was performed on the baboon native kidneys. Thus, the baboon was dependent upon the porcine kidneys for physiological function. The transplanted kidney exhibited primary nonfunction and the baboon was euthanized on post-op day 4. Pathology analysis of the explanted pig kidney revealed no evidence of hyperacute rejection.

EXAMPLE 20

Large Scale One-Pot Preparation Using NHSS

In a one liter glass beaker 25 grams of 8 arm PEG-NH$_2$, MW 10,000, 30 grams of Trisaccharide Free Acid and 14 grams of NHSS are dissolved by addition of 500 ml of 0.1 M MES buffer, pH 5.5. When all components are dissolved, 125 grams of EDC are added to the solution. The solution is stirred in a level 2 hood at ambient temperature for a minimum of 12 hours.

The diafiltration apparatus is set up and sterilized according to the manufacturer's instructions. The diafiltration system is drained and rinsed with sterile water until the pH of both the permeate and retentate streams are between pH 5.5 to 7.0. A minimum of 5 buffer exchanges is performed against sterile saline. The carboy connection is clamped off and the air filter line is opened. The diafiltered solution is concentrated to a third of the original volume. The volume is brought up to 750 mL sterile saline and sterile filtered through a 0.21μ filter and stored at 4° C.

EXAMPLE 21

Activity of Product as a Function of NHSS Concentration in the One-Pot Synthesis In five 15 mL centrifuge tubes, 250 mg PEG-(NH$_2$)$_8$ with a molecular weight of 20,000, 150 mg of GalGalGlcNAc, 625 mg EDC and 90 mg, 70 mg, 50 mg, 30 mg and 10 mg NHSS were dissolved in 5 mL of 50 mM MES buffer, pH 5.5, respectively, and the reactions carried out overnight. The respective solutions were dialyzed against DI water with four exchanges and lyophilized. The approximate IC$_{50}$'s were measured as described above and are listed below.

| NHSS [mg] | IC50 [mg/mL] |
|---|---|
| 10 | $5 \times 10^{-3}$ mg/mL |
| 30 | $1 \times 10^{-3}$ mg/mL |
| 50 | $5 \times 10^{-5}$ mg/mL |
| 70 | $5 \times 10^{-6}$ mg/mL |
| 90 | $2 \times 10^{-6}$ mg/mL |

EXAMPLE 22

Activity of Sugar Concentration in the One-Pot Synthesis

In five 15 mL centrifuge tubes, 250 mg PEG-(NH$_2$)$_8$ with a molecular weight of 20,000, 625 mg EDC, 70 mg NHSS, and 210 mg, 150 mg, 125 mg, 100 mg and 75 mg of GalGalGlcNAc were dissolved in 5 mL of 50 mM MES buffer, pH 5.5, respectively, and the reactions carried out overnight. The respective solutions were dialyzed against DI water with four exchanges and lyophilized. The approximate IC$_{50}$s were measured as described above and are listed below.

| Sugar [mg] | IC$_{50}$ [mg/mL] |
|---|---|
| 210 | $5 \times 10^{-6}$ mg/mL |
| 150 | $5 \times 10^{-6}$ mg/mL |
| 125 | $4 \times 10^{-5}$ mg/mL |
| 100 | $8 \times 10^{-4}$ mg/mL |
| 75 | $1 \times 10^{-3}$ mg/mL |

EXAMPLE 23

Activity of Product as a Function of pH in the One-Pot Synthesis

In six 15 mL centrifuge tubes, 250 mg PEG-(NH$_2$)$_8$ with a molecular weight of 20,000, 625 mg EDC, 70mg NHSS, and 150 mg of GalGalGlcNAc were dissolved in 5 mL of 50 mM MES buffer, pH 5, 5.5 and 6, and 0.1 M MOPS buffer pH 7 and 7.5, respectively, and additionally in DI water. The reactions were carried out overnight. The respective solutions were dialyzed against DI water with four exchanges and lyophilized. The approximately IC$_{50}$'s were measured as described above and are listed below.

| pH | IC50 [mg/mL] |
|---|---|
| 5 | $5 \times 10^{-6}$ mg/mL |
| 5.5 | $5 \times 10^{-6}$ mg/mL |
| 6 | $5 \times 10^{-6}$ mg/mL |
| 7 | $9 \times 10^{-4}$ mg/mL |
| 7.5 | $6 \times 10^{-3}$ mg/mL |
| DI water | $1 \times 10^{-5}$ mg/mL |

EXAMPLE 24

Activity of Product as a Function of EDC Concentration in the One-Pot Synthesis

In seven 15 mL centrifuge tubes, 250 mg PEG-(NH$_2$)$_8$ with a molecular weight of 20,000, 70 mg NHSS, 150 mg of GalGalGlcNAc and 100 mg, 200 mg, 300 mg, 400 mg, 500 mg, 625 mg and 800 mg EDC, were dissolved in 5 mL of 50 mM MES buffer, pH 5.5, respectively. The reactions were carried out overnight. The respective solutions were dialyzed against DI water with four exchanges and lyophilized. The approximate $IC_{50}$'s were measured as described above and are listed below.

| EDC [mg] | IC50 [mg/mL] |
|---|---|
| 100 | $9 \times 10^{-6}$ mg/mL |
| 200 | $9 \times 10^{-6}$ mg/mL |
| 300 | $7 \times 10^{-6}$ mg/mL |
| 400 | $5 \times 10^{-6}$ mg/mL |
| 500 | $5 \times 10^{-6}$ mg/mL |
| 625 | $5 \times 10^{-6}$ mg/mL |
| 800 | $5 \times 10^{-6}$ mg/mL |

EXAMPLE 25

Activity of Product as a Function of the Temperature of the One-Pot Synthesis

In three 50 mL centrifuge tubes, 500 mg PEG-$(NH_2)_8$ with a molecular weight of 20,000, 300 mg of GalGalGlcNAc, 1250 mg EDC and 140 mg NHSS were dissolved in 10 mL of 100 mM MES buffer, pH 5.5. The reactions were carried out overnight at 4° C., room temperature and 37° C. The respective solutions were dialyzed against DI water with four exchanges and lyophilized. The approximate $IC_{50}$s were measured as described above and are listed below.

| Temperature | IC50 [mg/mL] |
|---|---|
| 4° C. | $2 \times 10^{-6}$ mg/mL |
| RT | $5 \times 10^{-6}$ mg/mL |
| 37° C. | $5 \times 10^{-4}$ mg/mL |

EXAMPLE 26

Activity of Product as a Function of pH in the Two-Pot Synthesis

In six 15 mL centrifuge tubes, 250 mg 820E, 625 mg EDC and 70 mg NHSS were dissolved in 5 mL of 50 mM MES buffer, pH 5, 5.5, 6 and 6.5, and 0.1 M MOPS buffer pH 7 and 7.5, respectively. The reactions were carried out overnight. The respective solutions were dialyzed against DI water with four exchanges and lyophilized. The approximate $IC_{50}$s were measured as described above and are listed below.

| pH | IC50 [mg/mL] |
|---|---|
| 5 | $5 \times 10^{-5}$ mg/mL |
| 5.5 | $5 \times 10^{-5}$ mg/mL |
| 6 | $8 \times 10^{-5}$ mg/mL |
| 6.5 | $5 \times 10^{-4}$ mg/mL |
| 7 | $5 \times 10^{-4}$ mg/mL |
| 7.5 | $8 \times 10^{-3}$ mg/mL |

EXAMPLE 27

Activity of Product as a Function of EDC Concentration in the Two-Pot Synthesis

In three 15 mL centrifuge tubes, 250 mg 820E, 70 mg NHSS, 100 mg, 200 mg and 375 mg EDC, were dissolved in 5 mL of 50 mM MES buffer, pH 5.5, respectively. The reactions were carried out overnight. The respective solutions were dialyzed against DI water with four exchanges and lyophilized. The approximate $IC_{50}$s were measured as described above and are listed below.

| EDC [mg] | IC50 [mg/mL] |
|---|---|
| 100 | $8 \times 10^{-3}$ mg/mL |
| 200 | $4 \times 10^{-4}$ mg/mL |
| 375 | $8 \times 10^{-4}$ mg/mL |

EXAMPLE 28

Activity of Product as a Function of 820E Concentration in the Two-Pot Synthesis In three 15 mL centrifuge tubes, 70 mg NHSS, 625 mg EDC and 250 mg, 200 mg and 125 mg 820E were dissolved in 5 mL of 50 mM MES buffer, pH 5.5, respectively. The reactions were carried out overnight. The respective solutions were dialyzed against DI water with four exchanges and lyophilized. The approximate $IC_{50}$'s were measured as described above and are listed below.

| 820E [mg/mL] | IC50 [mg/mL] |
|---|---|
| 25 | $8 \times 10^{-3}$ mg/mL |
| 40 | $4 \times 10^{-5}$ mg/mL |
| 50 | $5 \times 10^{-5}$ mg/mL |

EXAMPLE 29

Reaction Kinetics of the One-Pot Synthesis

In order to follow the formation of 810S, one gram of 8 arm PEG-$NH_2$, MW 10,000, 5 grams of EDC, 0.56 grams of NHSS and 1.2 grams of the trisaccharide free acid were dissolved in 20 mL of 0.1 M MES buffer, pH 5.5. 2 mL samples were taken at 5 minutes, 30 minutes, one hour, 2 hours, 2.5 hours, three hours, four hours, five hours and overnight. The reaction was stopped by addition of 1 M Tris, pH 8.5. The respective solutions were dialyzed against DI water with four exchanges and lyophilized. The approximate $IC_{50}$s were measured as described above and are listed below.

| Time [min] | IC50 [mg/mL] |
|---|---|
| 5 | $2 \times 10^{-2}$ mg/mL |
| 30 | $3 \times 10^{-3}$ mg/mL |
| 60 | $6 \times 10^{-4}$ mg/mL |
| 120 | $8 \times 10^{-5}$ mg/mL |
| 150 | $6 \times 10^{-5}$ mg/mL |
| 180 | $5 \times 10^{-5}$ mg/mL |
| 240 | $3 \times 10^{-5}$ mg/mL |
| 300 | $2 \times 10^{-5}$ mg/mL |
| 960 | $5 \times 10^{-6}$ mg/mL |

EXAMPLE 30

Activity of Various Fractions of 810S 810S was fractionated by diafiltration through successively higher molecular weight cut-off membranes. 50 grams of 810S (lot#808003) was first diafiltered 6 times against sterile water to remove salt through a nominally 3,000 MW cut-off membrane. The retentate was then diafiltered six times against sterile water successively through nominally 30,000 MW, 100,000 MW, 300,000 MW and 500,000 MW cut-off membranes. The permeates and the final retentate were lyophilized. The dry powders were weighed and a mass balance established as listed below. The approximate $IC_{50}$s were measured as described above and are listed below.

| Fraction | IC50 [mg/mL] | Mass Balance [%] |
| --- | --- | --- |
| Original 810S | $5 \times 10^{-6}$ mg/mL | 100 |
| 3K > X < 30K permeate | $8 \times 10^{-3}$ mg/mL | 1.1 |
| 30K > X < 100K permeate | $6 \times 10^{-4}$ mg/mL | 16.7 |
| 100K > X < 300K permeate | $4 \times 10^{-4}$ mg/mL | 37.2 |
| 300K > X < 500K permeate | $7 \times 10^{-7}$ mg/mL | 10 |
| >500K retentate | $7 \times 10^{-7}$ mg/mL | 35 |

EXAMPLE 31

Synthesis and Activity of a Composition Comprising a Dendridic Polyamine Bearing Sixteen Amines 200 mg of a dendritic polyamidoamine with 16 amines, onto each end is coupled a PEG-amine of molecular weight 2000 was dissolved in 0.1 MES buffer, pH 5.5, and 250 mg GalGalGlcNAc was added and the pH readjusted to pH 5.5. 500 mg EDC was added and the reaction was rotated head over head overnight. The solution was dialyzed three times against 4 liters of DI water and lyophilized. An $IC_{50}$ Elisa as described above was performed and the approximate IC50 was determined to be 1 mg/mL.

EXAMPLE 32

Synthesis and Activity of a Composition Comprising a Dendridic Polyamine Bearing Thirty-two Amines 200 mg of a dendritic polyamidoamine with 32 amines, onto each end is coupled a PEG-amine of molecular weight 2000 was dissolved in 0.1 MES buffer, pH 5.5, and 250 mg GalGalGlcNAc was added and the pH readjusted to pH 5.5. 500 mg EDC was added and the reaction was rotated head over head overnight. The solution was dialyzed three times against 4 liters of DI water and lyophilized. An $IC_{50}$ Elisa as described above was performed and the approximate IC50 was determined to be 1 mg/mL.

EXAMPLE 33

Synthesis and Activity of a Composition Comprising a Dextran-Amine ($M_r$ ~10,000)

200 mg of a 10,000 molecular weight dextran-amine (Molecular Probes, Oreg.) was dissolved in 0.1 MES buffer, pH 5.5, and 250 mg GalGalGlcNAc was added and the pH readjusted to pH 5.5. 500 mg EDC was added and the reaction was rotated head over head overnight. The solution was dialyzed three times against 4 liters of DI water and lyophilized. An $IC_{50}$ Elisa as described above was performed and the approximate IC50 was determined to be $10^{-3}$ mg/mL.

EXAMPLE 34

Synthesis and Activity of a Composition Comprising a Dextran-Amine ($M_r$ ~40,000)

200 mg of a 40,000 molecular weight dextran-amine (Molecular Probes, Oreg.) was dissolved in 0.1 MES buffer, pH 5.5, and 250 mg GalGalGlcNAc was added and the pH readjusted to pH 5.5. 500 mg EDC was added and the reaction was rotated head over head overnight. The solution was dialyzed three times against 4 liters of DI water and lyophilized. An $IC_{50}$ Elisa as described above was performed and the approximate IC50 as determined to be $5 \times 10^{-6}$ mg/mL.

EXAMPLE 35

Synthesis and Activity of a Composition Comprising a Dextran-Amine ($M_r$ ~70,000)

200 mg of a 70,000 molecular weight dextran-amine (Molecular Probes) was dissolved in 0.1 MES buffer, pH 5.5, and 250 mg GalGalGlcNAc was added and the pH readjusted to pH 5.5. 500 mg EDC was added and the reaction was rotated head over head overnight. The solution was dialyzed three times against 4 liters of DI water and lyophilized. An $IC_{50}$ Elisa as described above was performed and the approximate IC50 was determined to be $10^{-5}$ mg/mL.

EXAMPLE 36

Synthesis and Activity of a Composition Comprising a Poly(lysine)-Amine ($M_r$ ~30,000)

200 mg of a 30,000 molecular weight poly-lysine (Sigma) was dissolved in 0.1 MES buffer, pH 5.5, and 500 mg GalGalGlcNAc was added and the pH readjusted to pH 5.5. 1400 mg EDC was added and the reaction was rotated head over head overnight. The solution was dialyzed four times against 4 liters of DI water and lyophilized. An $IC_{50}$ Elisa as described above was performed and the approximate IC50 was determined to be $10^{-5}$ mg/mL.

EXAMPLE 37

Synthesis of 810S: 8 Arm 10,000 Molecular Weight ($\alpha$Gal(1,3)Gal $\beta$ 1–4 GlcNAc)$_8$-PEG using EDC and NHSS for Coupling 62.5 g of EDC, 7 g of NHSS and 15 g of $\alpha$Gal(1,3)Gal $\beta$ 1–4 GlcNAc were dissolved in 50 mL of 0.1 M MES buffer, pH 5.5. The resulting solution was then transferred into a 500 mL glass beaker with stopper, in which 12.5 g of 8 arm 10,000 molecular weight PEG-$(NH_2)_8$ was dissolved in 100 mL of 0.1 M MES buffer, pH 5.5. The solution was brought up to 250 mL by addition of 0.1 M MES buffer, pH 5.5. The reaction mixture was shaken on an orbital shaker overnight. The reaction mixture was filled into dialysis tubes of molecular weight cut off 3,500 and dialyzed five times against 20 liters of DI water. The dialyzed material was freeze-dried to a yellowish powder. Amino group analysis revealed that more than 98% of amino groups were modified.

EXAMPLE 38

Comparison of 810S with Immunoapheresis

A series of experiments were initiated to directly compare the effects of 810S vs. immunoapheresis on circulating $\alpha$-Gal antibodies and peripheral $\alpha$-Gal antibody secreting cells (ASCs) in baboons.

A. Experimental Design

A total of 6 baboons were used. Three baboons (designated 51–98, 48–98 and 47–98) underwent immunoapheresis (IP) using $\alpha$-Gal columns, with plasma from 3 blood volumes being passed over the columns every 3 days for a total of 6 treatments. Three other baboons (designated 46–98, 52–98, 50–98) received IV infusions of 810S at 50 mg/kg every 3 days for a total of 6 treatments. No immunosuppression or exposure to pig organs was included in the protocol.

In both groups, serum samples and blood were collected to measure α-Gal antibody levels and ASCs during the treatment period and during a follow-up period out to approximately 150–180 days.

B. Results

Each IP treatment removed circulating IgM and IgG XNAs to 10–20% of initial levels, with a rebound of 50% of initial levels occurring in between each treatment. This is slightly different from what is usually observed, although our experience is with animals under immunosuppression. Typically, after plasma from 3 blood volumes passes over an α-Gal column, XNAs are undetectable in the post-treatment serum. A rebound of XNAs to 20–60% of the initial levels is usually observed after the 1st treatment, and this rebound effect generally diminishes with each IP treatment.

Figure 31:
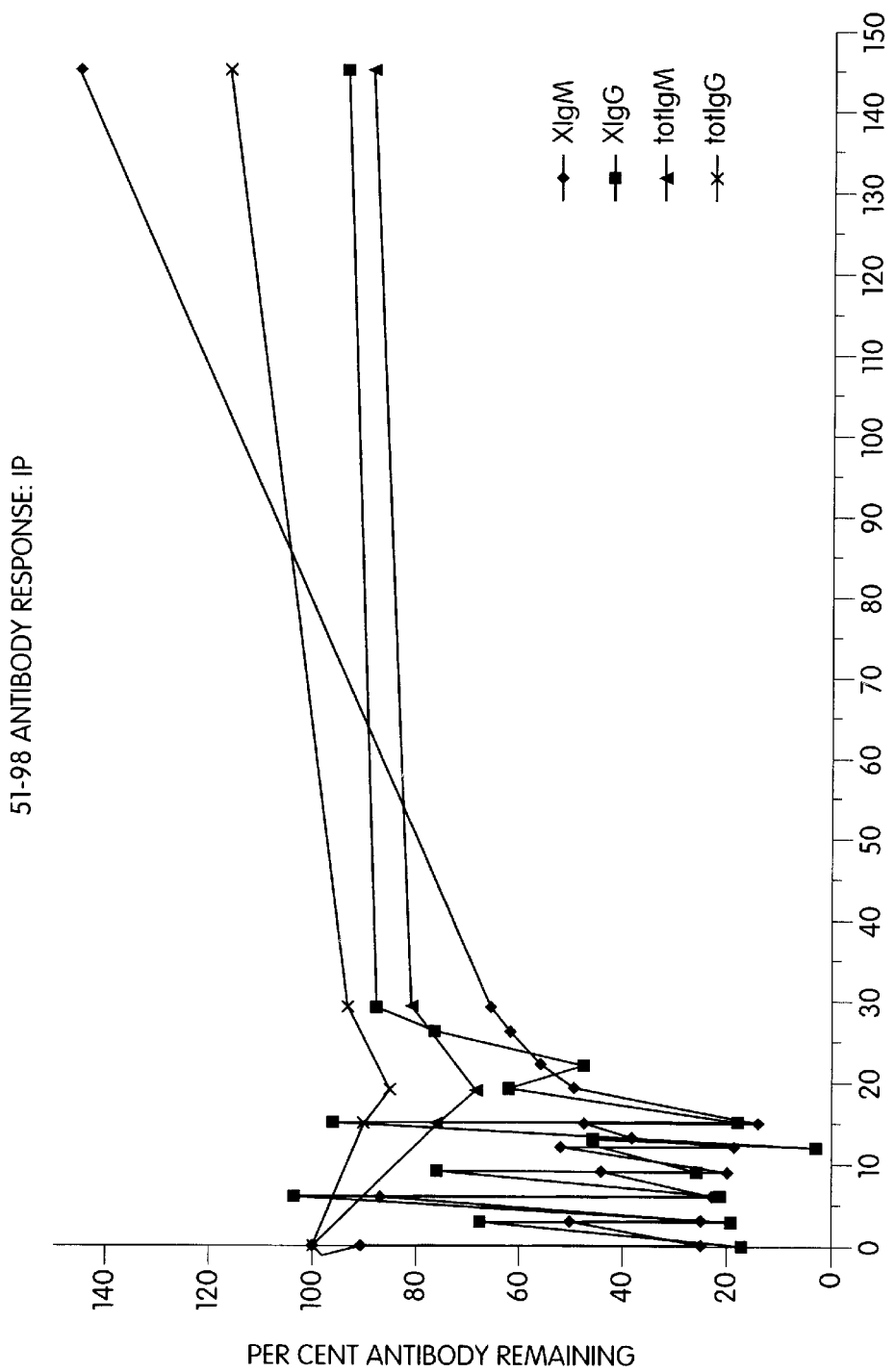
FIG. 31 is a graph of baboon 51–98 antibody response to IP. Baboon 51–98 underwent a total of 6 immunoapheresis treatments using α-gal columns every 3 days. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.
Figure 32:
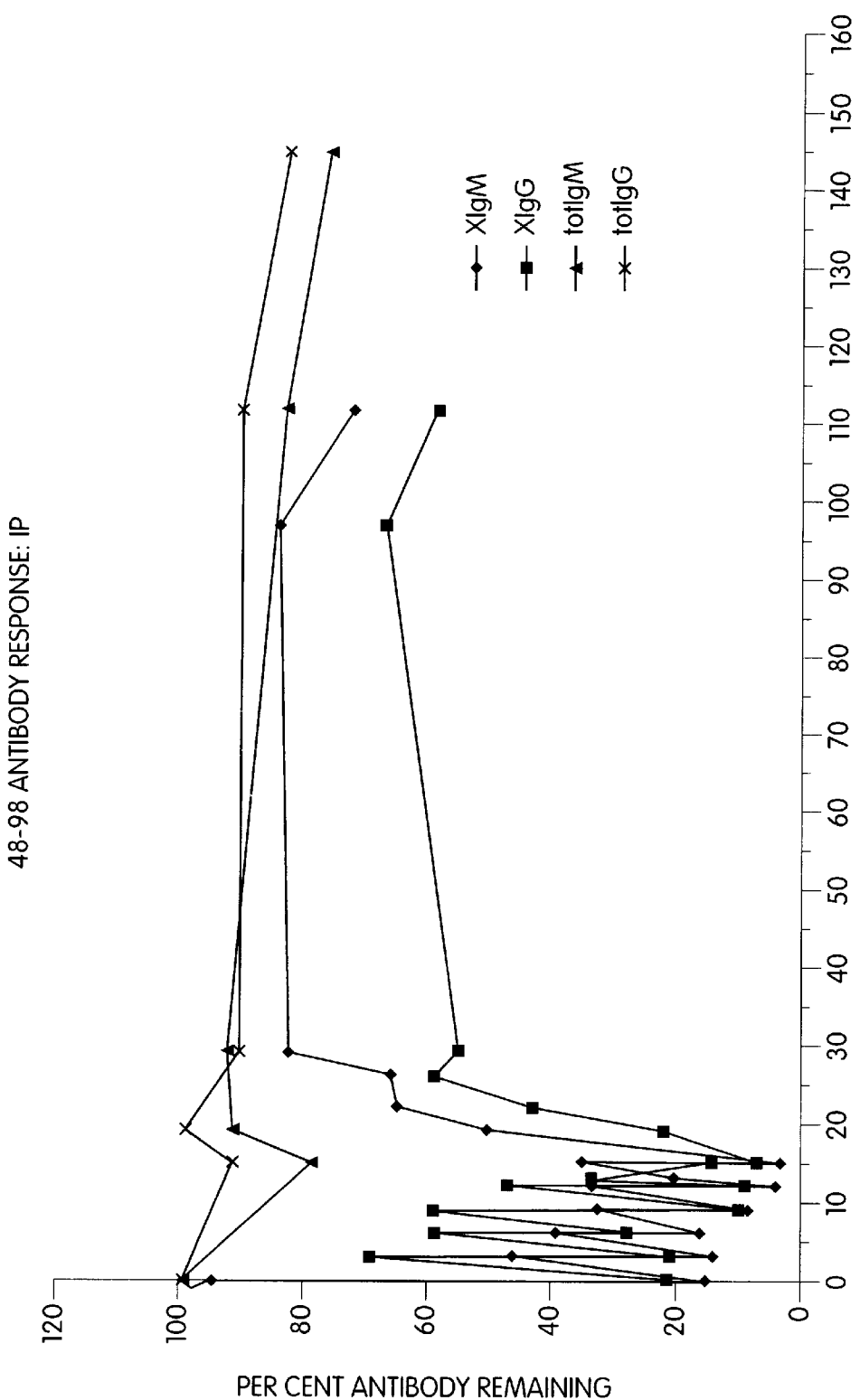
FIG. 32 is a graph of baboon 48–98 antibody response to IP. Baboon 48–98 underwent a total of 6 immunoapheresis treatments using α-gal columns every 3 days. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.
Figure 33:
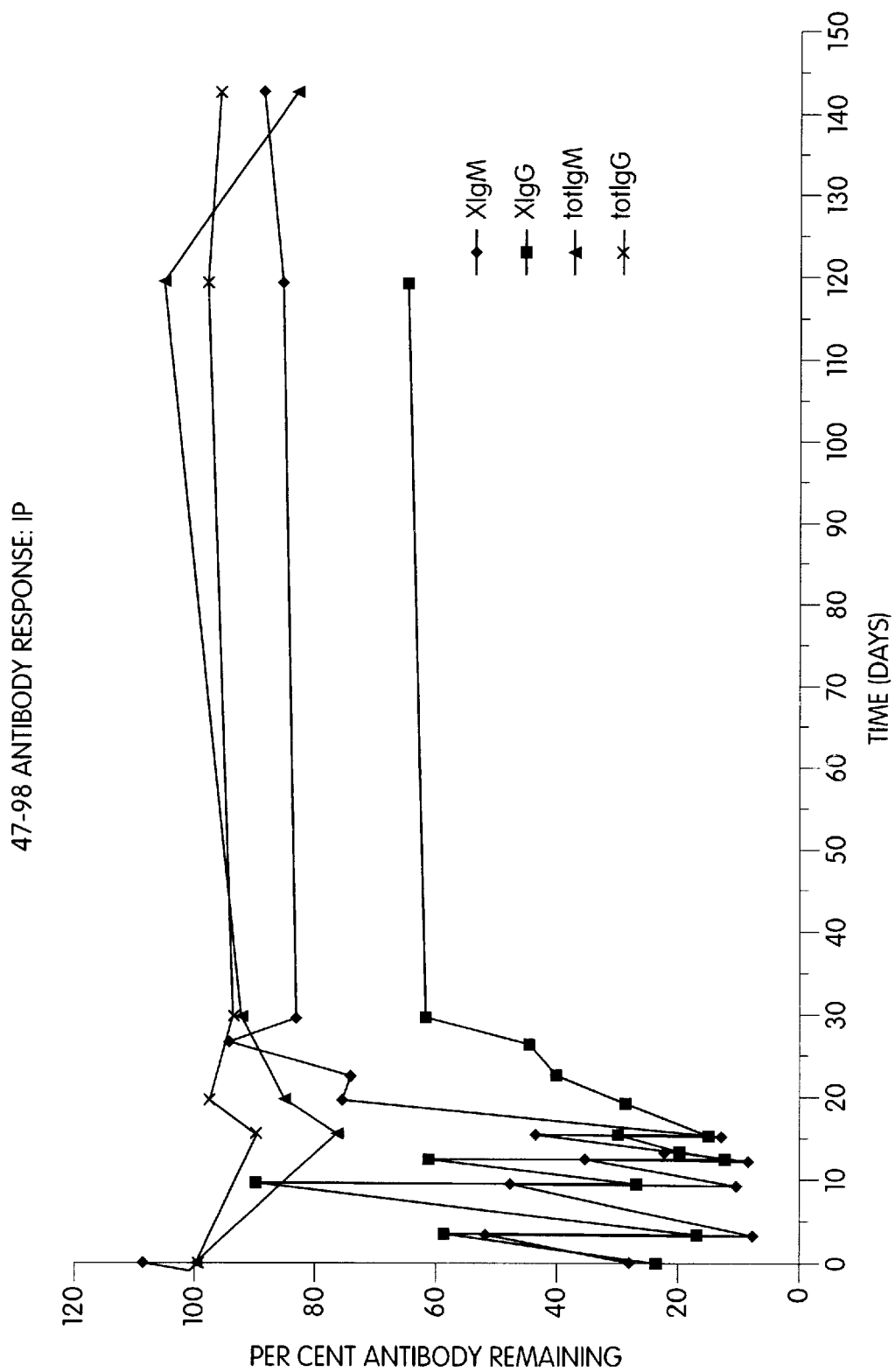
FIG. 33 is a graph of baboon 47–98 antibody response to IP. Baboon 47–98 underwent a total of 6 immunoapheresis treatments using α-gal columns every 3 days. Serum was analyzed for IgM and IgG antibodies directed against the α-gal epitope (XIgM or XIgG), as well as for total IgM (TotIgM) or total IgG (TotIgG) by ELISA. The per cent antibody remaining was calculated using baseline values as 100%.

Immediately after the final IP treatment, IgG and IgM XNA levels were at 7–17% and 3–15% of initial baseline levels, respectively. See FIGS. 26 and 31–33. Two weeks after the end of IP treatment (day 30), circulating IgG XNA levels for 2 of the baboons were at approximately 60% of initial levels and remained relatively constant out to day 145, while in the 3rd animal the XNAs had returned to approx. 90% initial levels by day 30 and reached about 1.5× baseline levels by day 145. See FIGS. 27 and 31–33. Total IgM and IgG levels in all 3 animals remained relatively constant throughout the experiment. See FIGS. 31–33.

After the 1st treatment with 810S, circulating IgG and IgM XNA levels in all 3 baboons dropped to between 1–13% of initial levels. See FIGS. 26 and 28–30. After the final 810S treatment, IgG XNA levels were 1–9% of baseline values, and IgM XNA levels were 1–3% of baseline values. See FIGS. 27–30 . By day 30, IgG XNA levels had reached 20–33% of baseline values, and IgM XNA levels were 8–18% of baseline values. See FIGS. 26 and 27.

Figure 34:
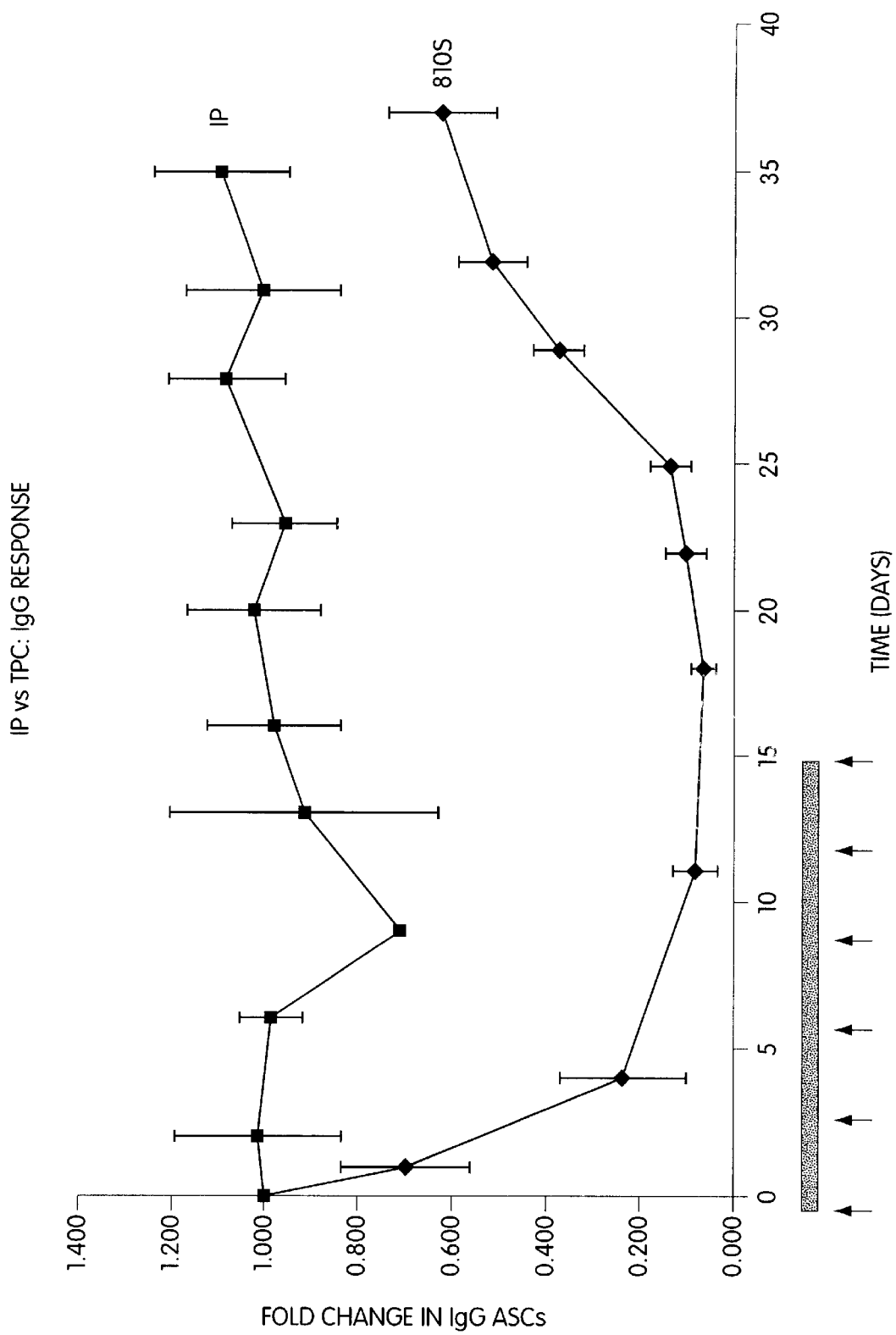
FIG. 34 compares the IgG response between IP and TPC (810) treated baboons. Baboons were either treated with 810S (50 mg/kg) every 3 days for a total of 6 treatments, or underwent a total of 6 immunoapheresis treatments using α-gal columns every 3 days. Peripheral blood mononuclear cells were collected and analyzed for the number of cells secreting IgG antibodies directed against α-gal using an ELISPOT analysis. The fold-change in antibody secreting cells (ASCs) was calculated by normalizing to baseline values. Values are represented as the mean from 3 baboons per group.
Figure 35:
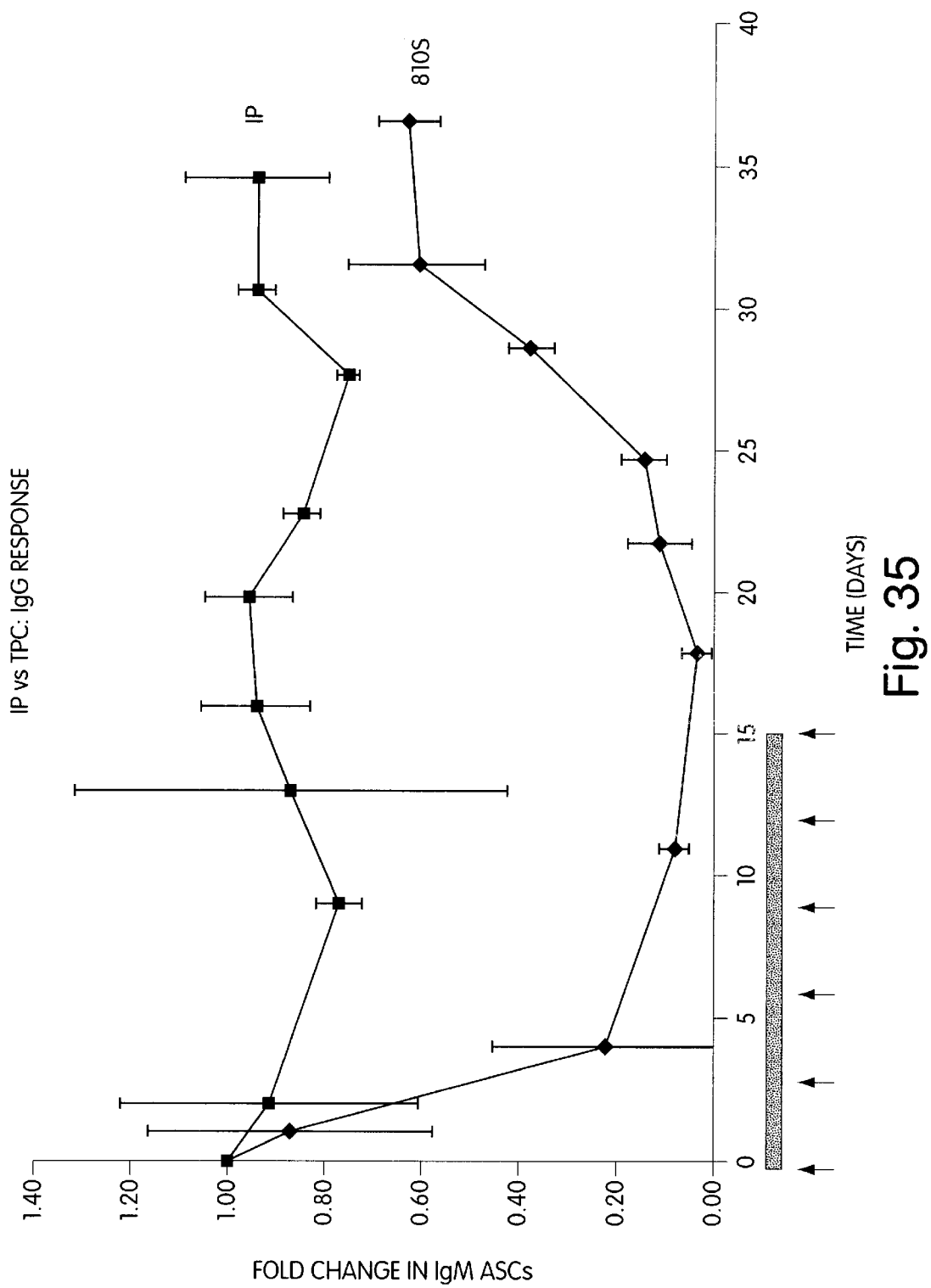
FIG. 35 compares the IgM response between IP and TPC (810) treated baboons. Baboons were either treated with 810S (50 mg/kg) every 3 days for a total of 6 treatments, or underwent a total of 6 immunoapheresis treatments using α-gal columns every 3 days. Peripheral blood mononuclear cells were collected and analyzed for the number of cells secreting IgM antibodies directed against α-gal using an ELISPOT analysis. The fold-change in antibody secreting cells (ASCs) was calculated by normalizing to baseline values. Values are represented as the mean from 3 baboons per group.

FIGS. 34 and 35 show the average fold-change in IgG and IgM response, respectively, for each of the IP and 810S treated animals.

To investigate whether 810S was still in baboon serum by day 30, serum was mixed with human serum and analyzed by ELISA for competition with human XNA binding to GAL-HSA. Results indicated day 30 baboon serum does not compete with human XNA binding to GAL, and therefore demonstrates that 810S is not still in circulation.

On day 184, IgG XNA levels in 2 810S-treated baboons were still at 30–38% of baseline values, whereas in one baboon IgG XNA levels had returned to baseline. The IgM XNA levels in this 3rd baboon reached 60% of baseline levels by day 184, while IgM XNA levels in the other 2 baboons reached 24–39% of baseline values. Total IgM and IgG levels in all 3 animals remained relatively constant throughout the experiment.

Baboon blood was also analyzed periodically for IgG and IgM XNA ASCs. As expected, IP had minimal effect on ASCs. By the second experiment with 810S IgM and IgG ASC levels were reduced to 20–40% of initial levels, by the fourth treatment, IgM and IgG ASCs were at about 10% initial levels, and after the sixth treatment they were approximately 3–6% of starting levels. On day 30, 2 weeks after 810S treatment was terminated, IgM and IgG ASC levels had returned to about 38% of initial levels, and 1 week later they were at about 62% of initial levels.

C. Summary

Analysis of XNA levels in baboons treated with IP indicates a reduction in XNA levels after each treatment, with rebounds observed in between treatments, and a gradual return of antibody when treatment is stopped. IgG XNA levels in 2 animals only returned to about 60% of initial values, which is unusual compared to what is typically observed. IgG XNAs in the 3rd animal, and IgM XNAs in all 3 animals did return to baseline values, with on animal overshooting this level slightly. In comparison, XNA levels are immediately reduced upon infusion of 810S, and the levels remain depressed during the entire course of the treatment. In 810S-treated baboons, XNAs show a much slower return after 810S treatment is discontinued compared to baboons treated with IP. Compare IP and 810S plots on FIGS. 34 and 35.

Analysis of circulating IgM and IgG ASCs demonstrates, as expected, no effect when animals undergo IP. However, an effect on the levels of these cells due to 810S infusion was clearly observed. ASC levels dropped soon after initiation of 810S treatment, and three weeks after 810S was discontinued, ASCs had not yet returned to initial levels.

IP physically removes circulating antibodies, and their return to the circulation is expected due to re-synthesis. While the mode of action of 810S is less clear, it is apparent from in vitro ELISA experiments that 810S can bind XNAs and prevent them from binding αGal epitopes. The sustained reduction on XNA levels several weeks after 810S treatment is discontinued, and the downregulation of αGal ASCs, implies that 810S has an immunoregulatory function, e.g., is tolerogenic, as well.

(v) Incorporation by Reference

All of the above-cited references and publications are hereby incorporated by reference.

(vi) Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A composition useful for reducing plasma levels of anti-(αGal(1,3)Gal) antibodies in a primate subject, said composition comprising:

a plurality of non-immunogenic polymers, wherein each of said non-immunogenic polymers comprises a plurality of αGal(1,3)Gal moieties covalently linked to said non-immunogenic polymer; and a plurality of cross-links between adjacent non-immunogenic polymers, wherein said cross-links are covalent tethers, derived from N-hydroxysulfosuccinimide, between a hydroxy group of an αGal(1,3)Gal moiety on a first non-immunogenic polymer and a hydroxy group of an αGal(1,3)Gal moiety on a second non-immunogenic polymer.

2. The composition of claim 1, wherein said polymer is a poly(amino)polyethylene glycol.

3. The composition of claim 1, wherein the non-cross-linked, pendant αGal(1,3)Gal moieties are represented by the formula:

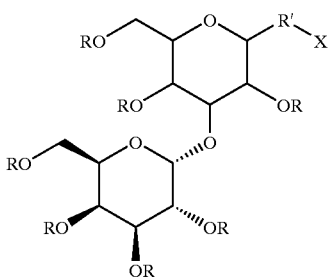

wherein:

R, independently for each occurrence, represents H, C$_1$–C$_6$ alkyl, acyl, benzyl, diphenylmethyl, triphenylmethyl, trialkylsilyl, dialkyl(aryl)silyl, alkyl(diaryl)silyl, or triarylsilyl;

R' is absent or represents an oligosaccharide of 1–8 saccharide residues; and

X represents a bond or linker moiety linking the oligosaccharide moiety to the polymer.

4. The composition of claim 1, wherein the αGal(1,3)Gal moiety is selected from the group consisting of αGal(1,3)βGal moieties; αGal(1,3)βGal(1–4)βGlcNAc moieties; and αGal(1,3)βGal(1,4)βGlc moieties.

5. The composition of claim 1, wherein the αGal(1,3)Gal moiety is a di-, tri-, tetra- or penta-saccharide.

6. The composition of claim 1, wherein the polymer includes multiple polymer scaffold units crosslinked therebetween.

7. The composition of claim 6, wherein the polymer scaffold units are crosslinked by a reagent derived from N-hydroxysulfosuccinimide.

* * * * *